US010280255B2

(12) United States Patent
Beckham et al.

(10) Patent No.: US 10,280,255 B2
(45) Date of Patent: May 7, 2019

(54) RENEWABLE RESINS AND UNSATURATED POLYESTERS AND METHODS OF MAKING THE SAME

(71) Applicants: Alliance for Sustainable Energy, LLC, Golden, CO (US); Colorado School of Mines, Golden, CO (US)

(72) Inventors: Gregg Tyler Beckham, Golden, CO (US); Derek R. Vardon, Golden, CO (US); Nicholas Rorrer, Golden, CO (US); John R. Dorgan, Golden, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 46 days.

(21) Appl. No.: 15/496,293

(22) Filed: Apr. 25, 2017

(65) Prior Publication Data

US 2017/0306085 A1    Oct. 26, 2017

Related U.S. Application Data

(60) Provisional application No. 62/450,620, filed on Jan. 26, 2017, provisional application No. 62/327,518, filed on Apr. 26, 2016.

(51) Int. Cl.
| | | |
|---|---|---|
| *C08G 63/52* | (2006.01) | |
| *C08J 3/24* | (2006.01) | |
| *C08K 5/00* | (2006.01) | |
| *C08L 25/06* | (2006.01) | |
| *C08L 31/06* | (2006.01) | |
| *G01N 25/48* | (2006.01) | |
| *G01R 33/46* | (2006.01) | |

(52) U.S. Cl.
CPC ............... *C08G 63/52* (2013.01); *C08J 3/24* (2013.01); *C08K 5/0025* (2013.01); *C08L 25/06* (2013.01); *C08L 31/06* (2013.01); *G01N 25/4866* (2013.01); *G01R 33/4633* (2013.01)

(58) Field of Classification Search
CPC .................................................. C08G 63/52
See application file for complete search history.

(56) References Cited

U.S. PATENT DOCUMENTS

| | | | |
|---|---|---|---|
| 2,012,267 A | 8/1935 | Corothers | |
| 3,644,284 A | 2/1972 | Cassar et al. | |
| 3,839,171 A | 10/1974 | Akamatsu et al. | |
| 3,842,142 A | 10/1974 | Harpold et al. | |
| 4,101,326 A * | 7/1978 | Barkey ................ | C08G 63/52 |
| | | | 430/285.1 |
| 4,258,143 A | 3/1981 | Dombroski et al. | |
| 4,771,101 A | 9/1988 | Pruett et al. | |
| 5,173,541 A | 12/1992 | Chen, Sr. et al. | |
| 8,415,496 B2 | 4/2013 | Frost et al. | |
| 2010/0240841 A1 | 9/2010 | Shimura et al. | |
| 2013/0023608 A1 | 1/2013 | Kellett et al. | |
| 2013/0202825 A1 | 8/2013 | Ambrose et al. | |
| 2016/0075820 A1 | 3/2016 | Narine et al. | |
| 2016/0083754 A1 | 3/2016 | Medoff et al. | |

FOREIGN PATENT DOCUMENTS

| | | |
|---|---|---|
| GB | 1194893 | 6/1970 |
| WO | WO 2014/054940 A2 | 4/2014 |

OTHER PUBLICATIONS

Azim et al., "Candida antarctica Lipase B-Catalyzed Synthesis of Poly(butylene succinate): Shorter Chain Building Blocks Also Work", Biomacromolecules, 2006, vol. 7, pp. 3093-3097.
Farmer et al., "Synthesis of Unsaturated Polyester Resins from Various Bio-Derived Platform Molecules", International Journal of Molecular Sciences, 2015, vol. 16, pp. 14912-14932.
International Search Report and Written Opinion for International Application No. PCT/US17/29337, dated Jul. 10, 2017, pp. 1-9.

* cited by examiner

*Primary Examiner* — Kuo Liang Peng
(74) *Attorney, Agent, or Firm* — Michael A. McIntyre

(57) ABSTRACT

An aspect of the present disclosure is a bioderived polymer that includes a first repeat unit that includes where n is an integer between 1 and 1000, and $R^1$ is a first hydrocarbon group.

24 Claims, 31 Drawing Sheets

A)

B)

A)

B)

RENEWABLE RESINS AND UNSATURATED POLYESTERS AND METHODS OF MAKING THE SAME

CROSS-REFERENCE TO RELATED APPLICATIONS

This application claims the benefit of U.S. Provisional Application Nos. 62/327,518 and 62/450,620 filed Apr. 26, 2016 and Jan. 26, 2017, respectively, the contents of which are incorporated herein by reference in their entirety.

CONTRACTUAL ORIGIN

The United States Government has rights in this disclosure under Contract No. DE-AC36-08GO28308 between the United States Department of Energy and the Alliance for Sustainable Energy, LLC, the Manager and Operator of the National Renewable Energy Laboratory.

BACKGROUND

Lignocellulosic biomass is an ideal renewable feedstock for producing a wide variety of monomers and polymers. In an integrated biorefinery, similar to a petroleum refinery, coproduction of monomers for polymer materials along with biofuels can improve profitability. Lignocellulosic biomass can be deconstructed into carbohydrate and lignin fractions and transformed into fuel, chemicals, and material building block substitutes. To do so, upgrading processes that incorporate direct biological, chemo-catalytic, or hybrid technologies are needed. Importantly, the high oxygen content of biomass (~35-45%) also makes it ideal for targeting oxygen-rich platform molecules such as polyester precursors with high atom efficiency when compared to petroleum to which oxygen must be added.

cis,cis-muconic acid is a promising renewable platform molecule that can be accessed from both sugars and lignin and be readily converted to both terephthalic acid and adipic acid, which can further be used to produce poly(ethylene terephthate) (PET) or Nylon 6,6, respectively. In the case of terephthalic acid, cis,cis-muconic acid is isomerized to trans,trans-muconic acid and subsequently reacted with ethylene and dehydrated, while adipic acid can be produced directly from the hydrogenation of muconic acid. While the use of muconic acid as a precursor to direct replacement monomers is being thoroughly explored, exploitation of its olefinic nature for utilization as a functional replacement in polymers has received less attention to date. As the use of muconic acid without further chemical processing has potential for economic and environmental advantages, there is a substantial incentive to explore utilization of muconic acid.

SUMMARY

An aspect of the present disclosure is a polymer that includes a first repeat unit that includes

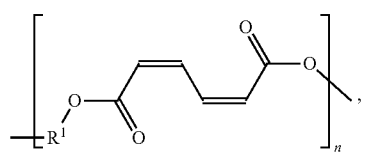

where n is an integer between 1 and 1000, and $R^1$ is a first hydrocarbon group.

In some embodiment of the present disclosure, the first hydrocarbon group may include at least one of a first linear alkane and/or a first branched alkane. In some embodiment of the present disclosure, the first hydrocarbon group may include the first linear alkane having a length between a C1 alkane and a C10 alkane inclusively. In some embodiment of the present disclosure, the first linear alkane may be a C4 alkane.

In some embodiment of the present disclosure, the polymer may further include a second repeat unit that includes

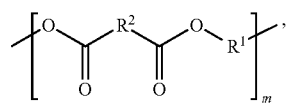

where m may be an integer between 1 and 100, and $R^2$ may be a second hydrocarbon group. In some embodiment of the present disclosure, the second hydrocarbon group may include a second linear alkane having a length between a C1 alkane and a C10 alkane inclusively. In some embodiment of the present disclosure, the second linear alkane may be a C4 alkane. In some embodiment of the present disclosure, at least a portion of the first repeat unit and at least a portion of the second repeat unit may form a structure that includes

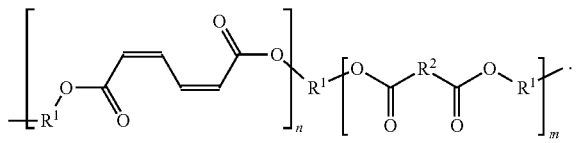

In some embodiment of the present disclosure, the polymer may further include a first terminal end and a second terminal end, where the first terminal end may be a hydroxyl group and/or a carboxylic acid group, the second terminal end may be a hydroxyl group and/or a carboxylic acid group, and the structure may be positioned between the first terminal end and the second terminal end. In some embodiment of the present disclosure, a molar amount of the first repeat unit incorporated into the polymer may be between 2.0 mol % and 100 mol %.

In some embodiment of the present disclosure, the polymer may have a melting point between 30° C. and 260° C. In some embodiment of the present disclosure, the polymer may have no melting point. In some embodiment of the present disclosure, the polymer may have a glass transition temperature between −100° C. and 75° C. In some embodiment of the present disclosure, the polymer may have a weight average molecular weight between $1 \times 10^3$ and $1 \times 10^6$. In some embodiment of the present disclosure, at least a portion of the carbon of the first repeat unit may be bio-derived. In some embodiment of the present disclosure, the portion of bioderived carbon may be determined to be bioderived according to ASTM D866.

An aspect of the present disclosure is a resin that includes

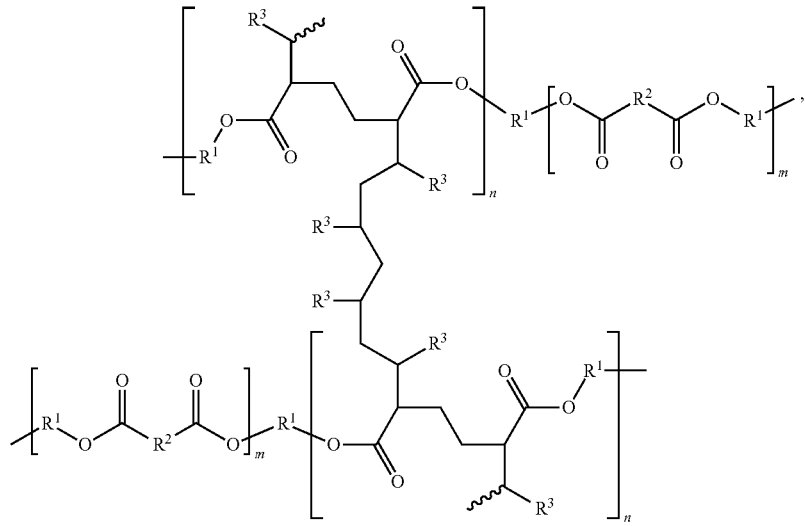

where n is an integer between 1 and 1000, $R^1$ is a first hydrocarbon group, m is an integer between 1 and 100, $R^2$ is a second hydrocarbon group, and $R^3$ is a third hydrocarbon group.

An aspect of the present disclosure is a method that includes a first reacting of a first polymer that includes

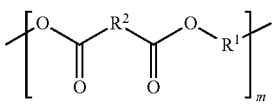

with muconic acid to form a second polymer that includes

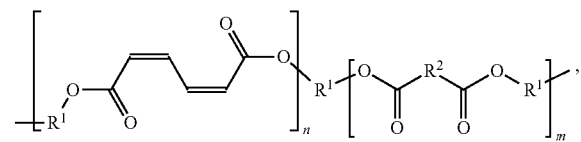

where m is an integer between 1 and 100, n is an integer between 1 and 1000, $R^1$ is a first hydrocarbon group, and $R^2$ is a second hydrocarbon group.

In some embodiments of the present disclosure, the muconic acid may be bioderived. In some embodiments of the present disclosure, the method may further include mixing benzoate with a strain of *Pseudomonas Putida*, where the *Pseudomonas Putida* metabolizes the benzoate to produce the muconic acid. In some embodiments of the present disclosure, the first polymer may include

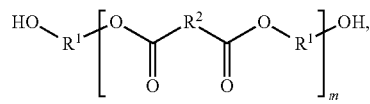

and the first reacting may include transesterification of the first polymer with the muconic acid to further produce $R^1OH$. In some embodiments of the present disclosure, the first reacting may further include a starting polymer that may include

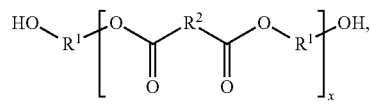

x may be an integer between 1 and 1000 and x may be less than m, and the starting polymer may react by condensation to produce the first polymer and water. In some embodiments of the present disclosure, the first reacting may further include a diol and dicarboxylic acid, and the diol and the dicarboxylic acid may react by condensation to produce the starting polymer. In some embodiments of the present disclosure, at least one of the diol and/or the dicarboxylic acid may be bioderived. In some embodiments of the present disclosure, the method may further include a second reacting of the second polymer with a crosslinker that may include a vinyl-terminated hydrocarbon to form a resin.

In some embodiments of the present disclosure, the resin may include

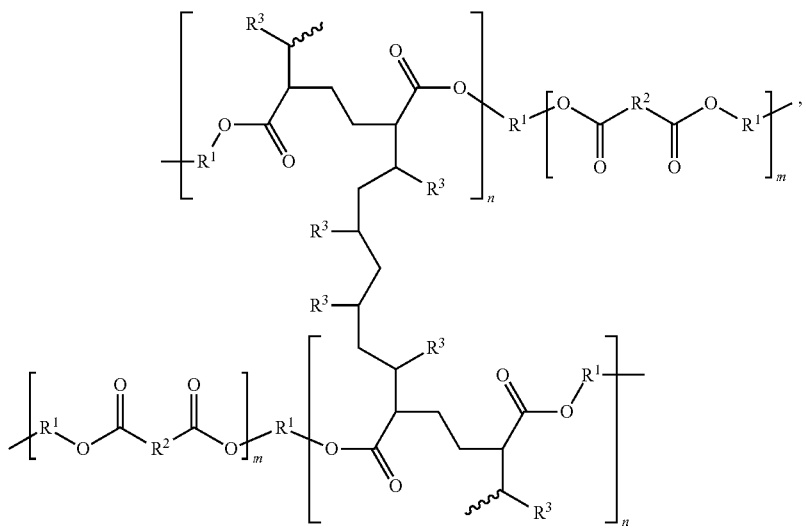

where $R^3$ may be a benzene ring.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 6 also illustrates (Panel B) molecular weights for the homopolymers and copolymers as a function of muconic acid loading, according to some embodiments of the present disclosure.

FIG. 7 also illustrates (Panel B) Differential Scanning calorimetry (DSC) scans for the multiple poly(butylene succinate-co-muconate) copolymers at a scan rate of 50° C./min. The inset in Panel B shows the melting temperature depression that was present in the PBSM and the shift in the glass transition temperature that occurred with increasing incorporation.

REFERENCE NUMBERS

Figure 1:
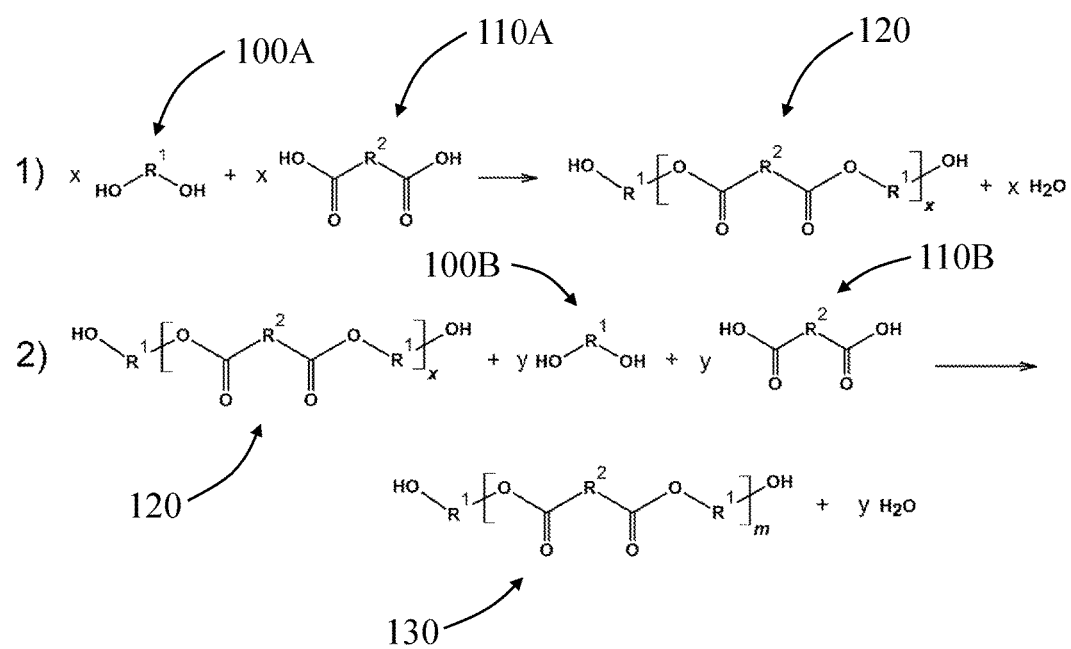
FIG. 1 illustrates reactions for converting a diol and a dicarboxylic acid to saturated polymers, according to some embodiments of the present disclosure.

100 . . . diol
110 . . . dicarboxylic acid
120 . . . starting polymer
130 . . . first polymer
140 . . . muconic acid
150 . . . second polymer
160 . . . alcohol
170 . . . crosslinker
180 . . . resin
190 . . . crosslinking chain
195 . . . polymer chain
400 . . . method
410 . . . initial reacting
420 . . . first reacting
430 . . . second reacting
440 . . . crosslinking

DETAILED DESCRIPTION

The present disclosure relates to saturated polymers, unsaturated polymers, resins, and composites. In some embodiments of the present disclosure, the starting materials for producing the saturated polymers, unsaturated polymers, resins, and composites may be bioderived. Reaction 1) of FIG. 1 illustrates a starting polymer 120 produced by reacting at least one diol 100A with a dicarboxylic acid 110A. In some embodiments of the present disclosure, a hydroxyl group of the diol 100A may react with a hydroxyl group of the dicarboxylic acid 110A by a condensation reaction, resulting in the formation of a carbon-oxygen-carbon linkage and water. A diol 100A may include any suitable hydrocarbon group, $R^1$, where the hydrocarbon group is positioned between a first hydroxyl group and a second hydroxyl group. The hydrocarbon group, $R^1$, may be at least one of a saturated hydrocarbon group and/or an unsaturated hydrocarbon group. For example, $R^1$ may be a straight chained hydrocarbon and/or branched hydrocarbon, with examples include any hydrocarbon group having a length between one carbon atom (C1) and twenty-four carbon atoms (C24), inclusively. An unsaturated hydrocarbon group, $R^1$, may include any suitable alkene group and/or aromatic group. In some embodiments of the present invention, the diol 100A may include any suitable functional group attached to the hydrocarbon group, $R^1$, for example, a branched group (i.e. alinke carbon), ketone, ether, alkenes, halogens, carboxylic acids, or secondary and tertiary alcohols. Examples of a diol 100A where $R^1$ is a linear alkane group include of 1,2-ethanediol, 1,3-propanediol, 1,2-propanediol, 1,4-butanediol, and/or 1,5-pentanediol. A dicarboxylic acid 110A may include any suitable hydrocarbon group, $R^2$, where the hydrocarbon group is positioned between a first carboxyl group and a second carboxyl group. The hydrocarbon group, $R^2$, may be at least one of a saturated hydrocarbon group and/or an unsaturated hydrocarbon group. For example, $R^2$ may be a straight chained hydrocarbon and/or branched hydrocarbon, with examples including any hydrocarbon group having a length between one carbon atom (C1) and twenty-four carbon atoms (C24) inclusively. An unsaturated hydrocarbon group, $R^2$, hydrocarbon group may include any suitable alkene group and/or aromatic group. In some embodiments of the present invention, the dicarboxylic acid 110A may have any suitable functional group attached to the unsaturated hydrocarbon group, $R^2$, for example, a branched group (e.g. a linked carbon), ketone, ether, alkenes, halogens, carboxylic acids, or secondary and tertiary alcohols. Examples of a dicarboxylic acid 110A where $R^2$ is a linear alkane group include oxalic acid, adipic acid, malonic acid, succinic acid, and/or glutaric acid. Other examples of dicarboxylic acids include terephthalic acid, isoterephthalic acid, cyclohexanedioc acid, and 4-cyclohexene 1,3-dicarboxylic acid.

Reaction 1) produces a starting polymer 120 by condensation reactions between two the hydroxyl group of at least one dicarboxylic acid 110A the hydroxyl group of at least one diol 100A. The resultant starting polymer 120 may be a substantially linear polymer terminating at a first end with a first hydroxyl group and at a second end with a second hydroxyl group, with the first hydrocarbon group, $R^1$, from the diol 100, and the second hydrocarbon group, $R^2$, from the dicarboxylic acid positioned between the first hydroxyl group and the second hydroxyl group. Thus, the starting polymer 120 may contain a first repeat unit that includes the second hydrocarbon group, $R^2$, positioned between a first ester group and a second ester group with both C=O groups of the ester groups covalently bound directly to the second hydrocarbon group, $R^2$. Referring again to Reaction 1) of FIG. 1, the first repeat unit terminates on one side (the left side as shown in Reaction 1) with the —O— group of the first ester group and on the remaining side (the right side as shown in Reaction 1) with the first hydrocarbon group, $R^1$, covalently bound to the —O— group of the first ester group as —O—$R^1$—. Thus, the first repeat unit may be designated as AB such that the starting polymer 120 may be viewed as —[AB]$_x$— where A is

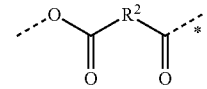

and

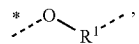

B is where the asterisk indicates the bond (a carbon-carbon bond) connecting A and B. For example, for the case where x is equal to 4, the starting polymer 120 may be represented as —ABABABAB—, or —[AB]$_4$—. In some embodiments of the present disclosure, the starting polymer 120 may terminate with at least one hydroxyl group and/or one HO—$R^1$— group. Again, for the case where x is equal to 4 and the starting polymer 120 is endcapped with hydroxyl groups, the starting polymer may be represented by HO—$R^1$ABABABAB-OH or HO—$R^1$[AB]$_4$-OH. The number of first repeat units incorporated into the starting polymer 120 is represented by x and may be between 1 and 100.

The starting polymer 120 may be characterized by at least a melting point, a glass transition temperature, and a molecular weight. In some embodiments of the present disclosure, the starting polymer 120 may have a melting point between 30° C. and 260° C. In some embodiments of the present disclosure, the starting polymer 120 may have a glass transition temperature between −100° C. and 75° C. In some embodiments of the present disclosure, the starting polymer 120 may have a weight average molecular weight between $1 \times 10^3$ and $1 \times 10^6$. In some embodiments of the present disclosure, the starting polymer 120 may be characterized by a polydispersity index between 1.8 and 2.2. In some embodiments of the present disclosure, the starting polymer 120 may be substantially crystalline, substantially amorphous, and/or a combination of both. For the example, where the starting polymer 120 is substantially amorphous, the starting polymer 120 may have no melting point temperature. Reaction 1) may be performed at a temperature between 60 and 300° C. in the presence or absence of a catalyst, for anytime between 4 minutes and four days, and with or without a solvent under pressure or subject to vacuum.

Referring again to FIG. 1, Reaction 2) shows that the starting polymer 120 may be extended by the reaction of additional diol 100B and additional dicarboxylic acid 110B to produce a longer chain first polymer 130. Reaction 2) may occur in parallel with Reaction 1), or Reaction 2) may occur in sequence, later in time, after Reaction 1). The diol 100B in Reaction 2) may be the same diol 100A used in Reaction 1), and/or it may be a different diol. The dicarboxylic acid 110B used in Reaction 2) may be the same dicarboxylic acid 110A used in Reaction 1), and/or it may be a different diol. Reaction 2) results in the growth of the starting polymer 120 such that the first polymer 130 is longer than the starting polymer 120. Referring to Reaction 2) in FIG. 1, m is an integer that is typically greater than the integer x. In some embodiments of the present disclosure, a first starting polymer 120 may react with a second starting polymer (not shown) by condensation reaction such that the two polymer molecules are joined to form the first polymer 130 and a water molecule. Thus, it should be clear to one of ordinary skill in the art that Reaction 1) and Reaction 2) may result in a mixture of unsaturated polymers endcapped with hydroxyl groups and/or carboxylic acid groups, such that the mixture may continue to react (e.g. by condensation) resulting in longer polymers over time, and resulting in larger weight average molecular weights. For example, for the case where m is equal to 5, the first polymer 130 may be represented as —ABABABABAM—, or —[AB]$_5$—. In some embodiments of the present disclosure, the first polymer 130 may terminate with at least one hydroxyl group and/or one HO—R$^1$— group. Again, for the case where m is equal to 5 and the first polymer 130 is endcapped with hydroxyl groups, the first polymer 130 may be represented by HO—R$^1$ABABABABAB-OH or HO—R$^1$[AB]$_5$-OH. The number of first repeat units incorporated into the first polymer 130 is represented by m and may be between 1 and 1000.

The first polymer 130 may also be characterized by at least a melting point, a glass transition temperature, and a molecular weight. In some embodiments of the present disclosure, the first polymer 130 may have a melting point between 30° C. and 260° C. In some embodiments of the present disclosure, the first polymer 130 may have a glass transition temperature between −100° C. and 75° C. In some embodiments of the present disclosure, the first polymer 130 may have a weight average molecular weight between $1 \times 10^3$ and $1 \times 10^6$. In some embodiments of the present disclosure, the first polymer 130 may be characterized by a polydispersity index between 1.8 and 2.2. In some embodiments of the present disclosure, the first polymer 130 may be substantially crystalline, substantially amorphous, and/or a combination of both. For the example, where the first polymer 130 is substantially amorphous, the first polymer 130 may have no melting point temperature. Reaction 2) may be performed at a temperature between 60 and 300° C. in the presence or absence of a catalyst, for anytime between 4 minutes and four days, and with or without a solvent under pressure or subject to vacuum.

Figure 2:
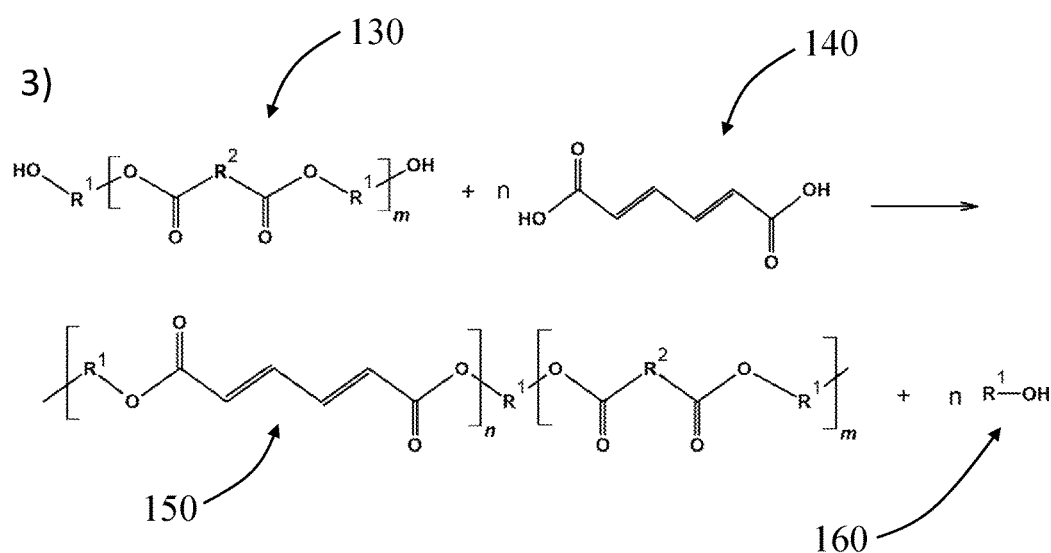
FIG. 2 illustrates a reaction for converting a saturated polymer to an unsaturated polymer by reacting the saturated polymer with muconic acid, according to some embodiments of the present disclosure.

FIG. 2 illustrates Reaction 3), which shows that the first polymer 130 may be reacted with muconic acid 140 to form a second polymer 150. Any isomeric form of muconic acid 140 may be used in Reaction 3), including at least one of cis,cis-muconic acid, cis,trans-muconic acid, and/or trans,trans-muconic acid. The second polymer 150 contains a second repeat unit

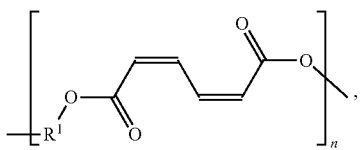

where n is an integer between 1 and 1000. The solid lines intersecting the brackets represent covalent bonds to a neighboring atom (not shown). Similarly, the lines intersecting the brackets in the representation of the second polymer 150 shown in FIG. 2 represent covalent bonds to a neighboring atom (not shown). The second repeat unit may be represented by C. Thus, in some embodiments, for the example of when x is equal to 4 and the second polymer 150 is endcapped with hydroxyl groups, the second polymer 150 may be visualized as HO-CABABABAB-OH. In some embodiments of the present disclosure, the second polymer 150 may be visualized as HO—C$_n$AB$_m$-OH, where n is an integer between 1 and 1000 and m is an integer between 1 and 1000. As shown in FIG. 2, the second polymer 150 is unsaturated; e.g. contains double bonds provided by the muconic acid. The second polymer 150 may also be characterized by at least a melting point, a glass transition temperature, and a molecular weight. In some embodiments of the present disclosure, the second polymer 150 may have a melting point between 30° C. and 260° C. In some embodiments of the present disclosure, the second polymer 150 may have a glass transition temperature between −100° C. and 75° C. In some embodiments of the present disclosure, the second polymer 150 may have a weight average molecular weight between $1 \times 10^3$ and $1 \times 10^6$. In some embodiments of the present disclosure, the second polymer 150 may be characterized by a polydispersity index between 1.8 and 2.2. In some embodiments of the present disclosure, the second polymer 150 may be substantially crystalline, substantially amorphous, and/or a combination of both. For the example, where the second polymer 150 is substantially amorphous, the second polymer 150 may have no melting point temperature. Reaction 3) may be performed at a temperature between 60 and 300° C. in the presence or absence of a catalyst, for anytime between 4 minutes and four days, and with or without a solvent under pressure or subject to vacuum.

Figure 3:
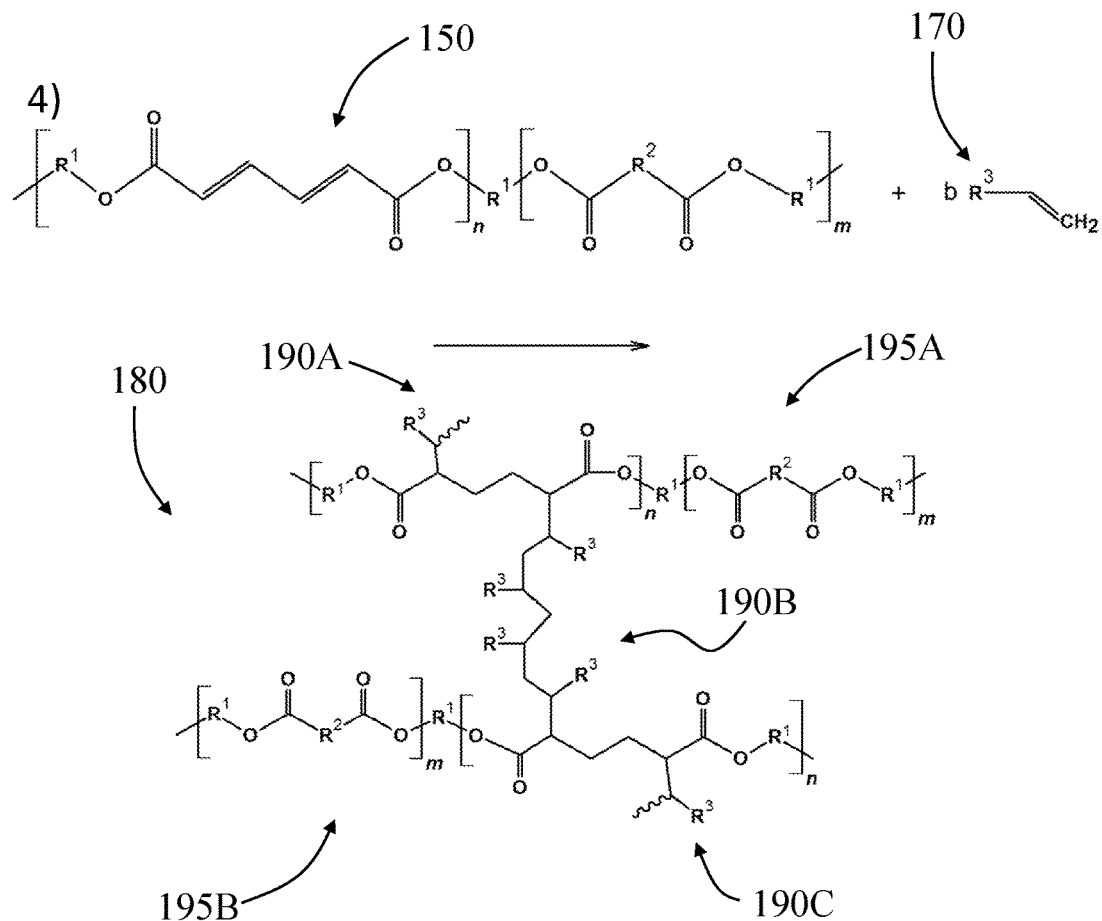
FIG. 3 illustrates a reaction for converting an unsaturated polymer to a resin by reacting the unsaturated polymer with a crosslinker, according to some embodiments of the present disclosure.

FIG. 3 illustrates Reaction 4), which shows an example of how the second polymer 150 may be reacted with a crosslinker 170 to produce a resin 180. The resin 180 is constructed of multiple polymer chains 195 covalently bound together by multiple crosslinking chains 190. One crosslinking chain 190B links a first polymer chain 195A to a second polymer chain 195B. Two crosslinking chains, 190A and 190C, link additional neighboring polymer chains 195 that are not shown in FIG. 3. The crosslinker 170 is shown as a hydrocarbon group, $R^3$, having a vinyl group. Thus, one or more crosslinkers 170 may react with the double-bonds in the second polymer 150 to form crosslinking chains that covalently attach two or more second polymers 150 to create the resin 180. Other examples of suitable crosslinkers 170 include styrene, methacrylic acid, acrylic acid, methyl methacrylate, divinyl benzene, and electron withdrawing groups that undergo Michael Addition (e.g. some alcohols). Reaction 4) may include at least one of a reaction initiator (either free radical, cationic, anionic, such as AIBN, hydrogen peroxide, potassium peroxide) and/or a cross-linking agent (e.g. divinyl benzene or derivatives of ethylene glycol di(methyl) acrylate). In some embodiments of the present disclosure, Reaction 4) may be performed to produce a composite material (not shown) using at least one particulate filler. Examples of fillers include carbon, boron, glass, high tenacity polymers, ceramics, metals, wood flour, sawdust, other plant or biologically sourced fillers, and combinations thereof. Other filler examples include powdered marble, quartz, other stone materials, and combinations thereof. Other composite materials (not shown) may be produced by combining Reaction 4) with mineral fibers and/or organic fibers to produce fiber matts, and/or fabrics containing the resin 180. Examples of suitable fibers include fibers manufactured from at least one of carbon, boron, glass, high tenacity polymers, metals, ceramics, plant fibers, and/or other biologically based fibers. For the example of a fiberglass composite containing about 68 wt % fiberglass and about 32 wt % resin, the fiberglass composite may have a shear modulus between about 20 GPa and about 70 GPa, a glass transition temperature between about 85° C. and about 95° C., and a decomposition temperature between about 350° C. and about 450° C.

The resin can be characterized by its structural properties (i.e. molecular weight distribution, interaction parameters, phase separation), rheological properties (i.e. viscosity, shear, storage, or loss modulus) mechanical properties (i.e. stress at break, strain at break, youngs modulus, elongation, fracture mechanisms) and its thermal properties (i.e. glass transition temperature, melting temperature, decomposition temperature, heat deflection temperature. The resin can be cross-linked with or without initiator, under elevated temperatures up to 400° C., auto catalytically, or with radiation such as UV.

In some embodiments of the present disclosure, the raw materials used to produce at least one of the starting polymer 120, the first polymer 130, and/or the second polymer 150 may be bioderived. For example, at least one of the diol 100, the dicarboxylic acid 110, and/or the muconic acid 140 may be bioderived. In some embodiments of the present invention, at least one of the diol 100, the dicarboxylic acid 110, and/or the muconic acid 140 may be produced by at least one microorganism metabolizing a substrate. For example, muconic acid 140 may be produced by a strain of *Pseudomonas Putida* metabolizing benzoate.

Whether or not a reactant or product described herein is "bioderived" may be determined by analytical methods. Using radio carbon and isotope ratio mass spectrometry analysis, the bio-based content of materials can be determined. ASTM International, formally known as the American Society for Testing and Materials, has established a standard method for assessing the biobased content of carbon-containing materials. The ASTM method is designated ASTM-D6866. The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pNMC value obtained correlates directly to the amount of biomass material present in the sample. Thus, ASTM-D866 may be used to validate that the compositions described herein are and/or are not derived from renewable sources.

Figure 4:
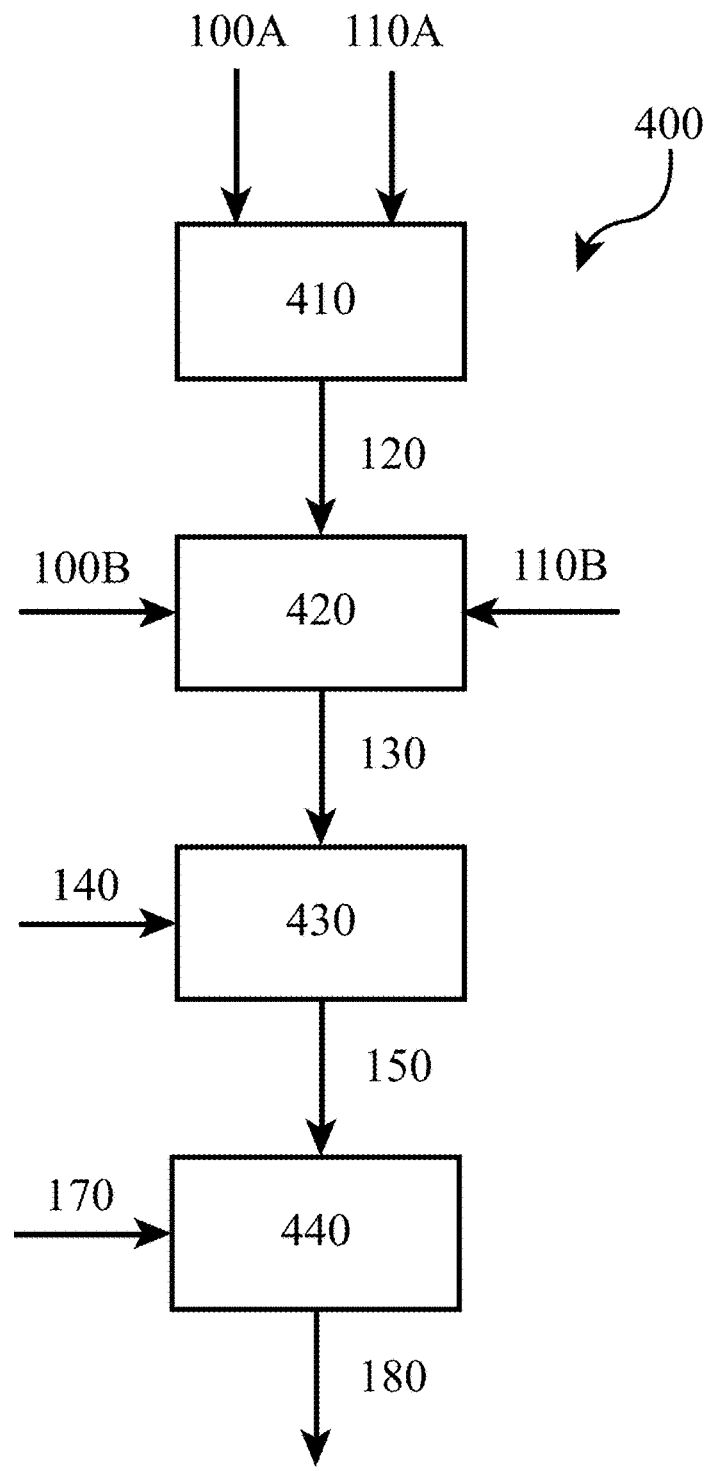
FIG. 4 illustrates a method for converting a diol, a dicarboxylic acid, and muconic acid to saturated polymers, unsaturated polymers, and resins, according to some embodiments of the present disclosure.

FIG. 4 illustrates a method 400 for producing polymers and/or resins from the diol 100, the dicarboxylic acid 110, and muconic acid 140 as described above. The method 400 may begin with an initial reacting 410 step that includes reacting a diol 100A and a dicarboxylic acid 110A to form the starting polymer 120 as described above. The starting polymer 120 may then be passed to a first reacting 420 step, where at least one additional diol 100B and/or additional dicarboxylic acid 110B are reacted with the starting polymer 120, resulting in chain growth and the formation of the first polymer 130 as described above. The first polymer 130 may then be fed to a second reacting step 430 where the first polymer 130 may be reacted with muconic acid 140 to produce the second polymer 150 as described above. In some embodiments of the present disclosure, at least one of the initial reacting 410, the first reacting 420, and/or the second reacting 430 may all be performed substantially simultaneously in the same reaction vessel. In some embodiments of the present disclosure, at least two of the initial reacting 410, the first reacting 420, and/or the second reacting 430 may be performed substantially sequentially time in the same reaction vessel and/or in different reaction vessels. Finally, the method 400 may include a crosslinking 440 step, where the second polymer 150 is mixed with a crosslinker 170 to produce the resin 180 as described above. Reactions for the preparation of the polymers and/or the resin may be conducted under flow in a plug flow reactor, via reactive extrusion, in a continuous stirred reactor, or in a batch reactor.

The present disclosure relates to muconic acid for the production of plastics incorporating unsaturated polyester (copolymer) resins, which are versatile materials used in a wide variety of applications with a thriving and growing global market. Copolymer resins form durable structures and coatings when cross-linked with a reactive crosslinker, most commonly styrene. copolymers resins are often combined with fiberglass or mineral fillers. When combined with fiberglass or carbon fiber, they are referred to as fiber-reinforced plastics (FRP). FRP composites are strong, lightweight and durable and are widely used in the construction and transportation industries. Copolymer resins with mineral fillers are used to make cultured marble and solid surface countertops, gel coats, automotive repair putty and filler, and a host of other items. It is common to adjust material formulations for specific end use applications of FRPs. Molecularly tunable resins are highly desirable; for example the ability to adjust thermal properties like the glass transition, melting, and degradation temperatures is considered advantageous. Copolymer global markets are forecast to reach USD 10.48 billion in 2019.

The present disclosure details the use of bio-derived muconic acid in combination with other bio-derivable monomers to synthesize linear biopolymers suited for use as resins that can be used copolymer resin applications and/or other applications. Demonstrating the synthesis of these new materials opens the pathway for functional replacement of high-valued petroleum derived materials. Such replacement is expected to both improve the sustainability metrics of the materials themselves and to improve biorefinery economics to enable biofuel production. In the present study, a family of copolymers (also referred to herein as a "second polymer") is produced by incorporating muconic acid into four different succinate based homopolymers (also referred to herein as a "first polymer" and/or a "starting polymer"). The properties of these copolymers differ from their corresponding homopolymers. A low molecular weight copolymer poly(butylene succinate-co-muconate) (PBSM) is synthesized, combined with styrene, infused into a long glass fiber mat, and crosslinked to create a prototypical fiberglass panel. Overall, the present study conclusively demonstrates the value-added nature of bio-derived muconic acid in producing novel unsaturated copolymers.

In this work, cis,cis-muconic acid was selected for the production of unsaturated resins due to its ability to be biologically derived and the double bonds in its structure. cis,cis-muconic acid can be produced via the oxygen-dependent 1,2-cleavage of catechol, a central intermediate in degradation of aromatic compounds in many aromatic catabolic microbes. Muconic acid can be accessed from both sugars or lignin-derived aromatic compounds. Currently, muconic acid is not industrially produced at large-scale, but it is a promising platform chemical because of its facile conversion, through hydrogenation, to adipic acid. Depending on the target application, muconic acid can be subject to myriad catalytic transformations, allowing for the production of value added monomers. Because muconic acid possesses terminal carboxylic acids, it is a strong candidate for direct polymerization and implementation in UPE-like resins. The initial homopolymer suite for muconic incorporation was selected because the structural units can be derived from molecules that can also be produced utilizing biochemical pathways. As such, it is anticipated that the family of polymers, both homopolymers and/or copolymers, represented in this study could potentially be fully available from biorenewable resources.

PBS is a potentially promising homopolymer structure for the inclusion of varying levels of muconic acid to produce useful copolymers. PBS is commercially available from bio-renewable resources. Succinic acid is produced biologically and transformed to butanediol through the catalytic conversion of succinic acid. Additionally, butanediol can be produced biologically at very high titers. Furthermore, PBS has the most robust thermal profile of the homopolymers studied—it has a low $T_g$ but a high $T_m$. This combination is useful in materials requiring ductility, toughness, and some thermal resistance.

Figure 5:
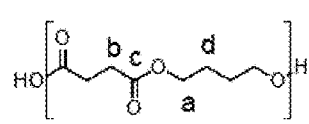
FIG. 5 illustrates $^{13}C$ NMR results of a poly(butylene succinate) (PBS) homopolymer (Panel A) and for a muconic acid containing copolymer, poly(butylene succinate-co-muconate) (PBSM) PBSM-25% (Panel B), according to some embodiments of the present disclosure. The incorporation of the double bond is present in the range from 120 to 160 ppm.
Figure 5:
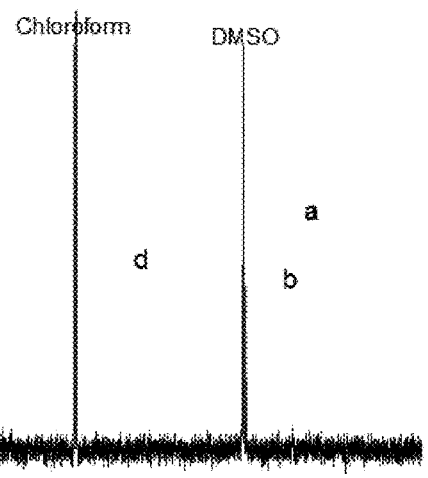
Figure 5:
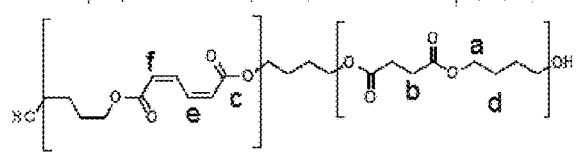
Figure 5:
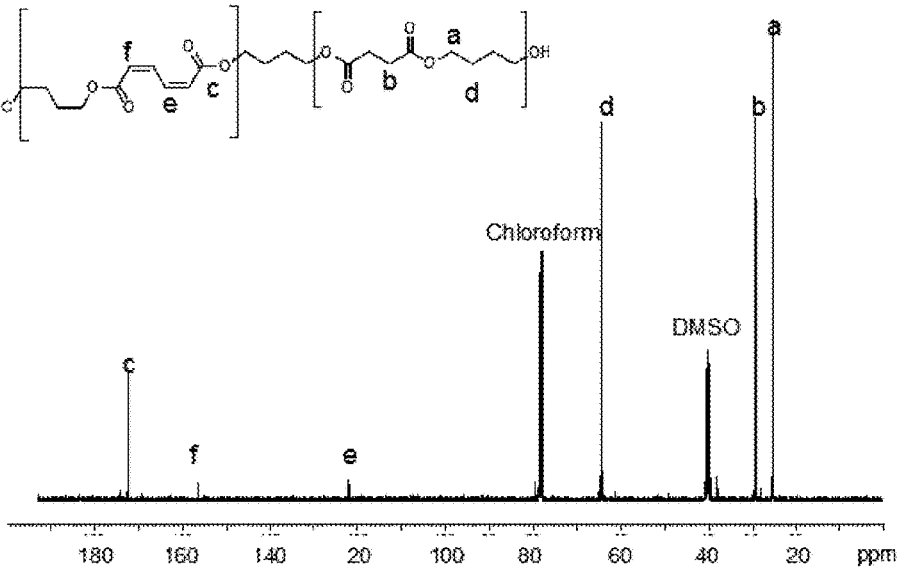

To investigate the effect of muconic acid incorporation on copolymer properties, a series of homopolymers were first synthesized and characterized. Poly(butylene succinate) (PBS), poly(ethylene succinate) (PES), poly(propylene succinate) (PPS), and poly(hexylene succinate) (PHS) homopolymers were synthesized via catalyzed condensation polymerization. Scheme 1 illustrates the condensation with transesterification polymerization reaction in the presence of titanium butoxide V as a catalyst. Initially, an excess of a diol was reacted with a dicarboxylic acid to form oligomers. Subsequently, a transesterification catalyst was introduced to form higher molecular weight polymers. Homopolymer structures were confirmed using one-dimensional $^1$H and $^{13}$C NMR. The molecular weight distribution was determined by GPC. A representative NMR spectrum for a PBS homopolymer produced is provided in FIG. 5, Panel A).

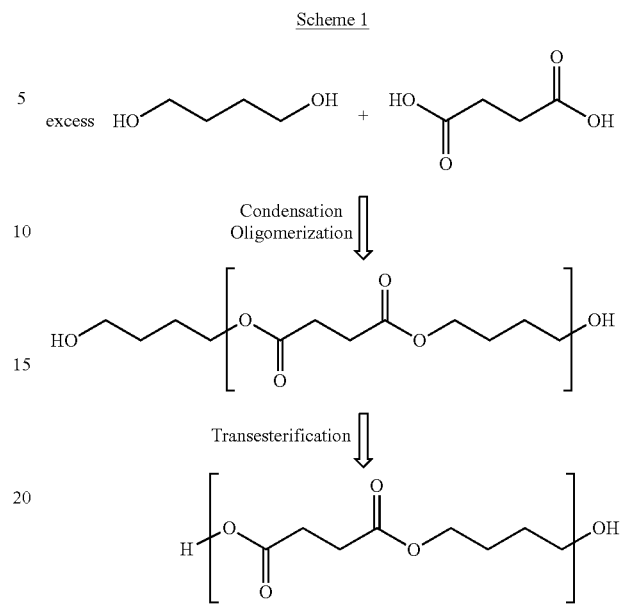

Scheme 1

Thermal properties for all synthesized homopolymers were determined using differential scanning calorimetry (DSC) and thermal gravimetric analysis (TGA) under nitrogen. The glass transition temperature, $T_g$, the melting temperature, $T_m$, and the $T_{D,50}$, the temperature at which 50% mass loss occurs, were measured for each homopolymer. Both thermal and molecular weight data for the homopolymers are summarized in Table 1 below. The PBS homopolymer was the most robust homopolymer based on its favorable thermal properties ($T_g \sim -40°$ C., $T_m = 120°$ C., $T_{D,50} = 425°$ C.). In contrast to PBS, the other homopolymers exhibited melting temperatures lower than 100° C., usually around 60° C. However, all homopolymers exhibited glass transition temperatures below $-10°$ C. and degradation temperatures above 400° C. The higher molecular weight of the poly(butylene succinate) is indicative of the higher reactivity between the two monomers. All of the polymers exhibited a similar enthalpy of fusion indicating that they possess similar degrees of crystallinity.

TABLE 1

Homopolymer thermal and molecular weight properties. Thermal properties determined by DSC and TGA and absolute molecular weight determined via GPC with light scattering detection.

| | $T_m$ (° C.) | $T_g$ (° C.) | $T_{D,50}$ (° C.) | $\Delta H_f$ (J/g) | $M_w$ | PDI |
|---|---|---|---|---|---|---|
| Poly(ethylene succinate) | 105 | −13 | 445 | 36.7 | $4.7*10^4$ | 1.9 +/− 0.1 |
| Poly(propylene succinate) | 48 | −34 | 415 | 43.1 | $6.1*10^4$ | 1.9 +/− 0.1 |
| Poly(butylene succinate) | 130 | −31 | 425 | 64.1 | $1.95*10^5$ | 2.0 +/− 0.1 |
| Poly(hexylene succinate) | 58 | −40 | 430 | 52.7 | $8.7*10^4$ | 2.0 +/− 0.1 |

Muconic acid was incorporated into all of the homopolymers described above to form unsaturated copolymers. To do so, cis,cis-muconic acid was added to the reaction mixture at an initial loading of 10 mol % of the total carboxylic groups. NMR spectra confirmed the incorporation, albeit at a reduced level compared to that charged to the reactor. Due to the superior thermal properties and emerging commercial significance of PBS homopolymers, muconic acid was also added to the PBS homopolymer reaction mixtures at 1, 5 and 25 mol % of the initial acid groups to form a series of copolymers that exhibited varying amounts of unsaturation. The copolymers formed were poly(butylene succinate-co-muconate), abbreviated as PBSM-XX %, where XX denotes the initial reactor charge. The NMR spectra confirm the presence of double bonds in the copolymer backbones. A representative spectrum is presented in FIG. 5, Panel B for the 25% muconic acid loaded material; peaks "e" and "f" correspond to the two distinct double bonds, which are not present in the initial PBS homopolymer. After synthesis, all polymers were dissolved and re-precipitated to remove the unreacted monomers. Accordingly, the NMR spectra are conclusive evidence of muconic acid incorporation into the PBS starting material. In all cases, quantitative analysis by peak integration demonstrates that the final level of incorporation is lower than the initial muconic acid charge to the reactor. Finally, NMR indicates that the muconic structural unit of the copolymer maintains the cis,cis configuration; there is no evidence of thermally induced isomerization.

Figure 6:
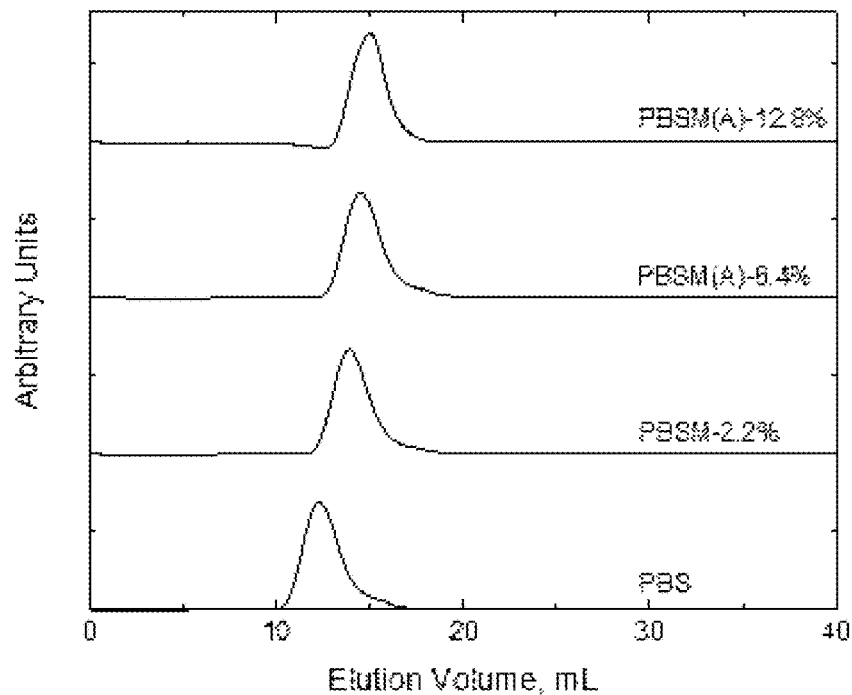
FIG. 6 illustrates (Panel A) GPC chromatographs of the poly(butylene succinate-co-muconate) copolymers compared with the homopolymer, according to some embodiments of the present disclosure. Traces reveal a decreasing molecular weight with muconic acid incorporation but a single peak indicates that only one polymer was present (lower molecular weights elute at longer times).
Figure 6:
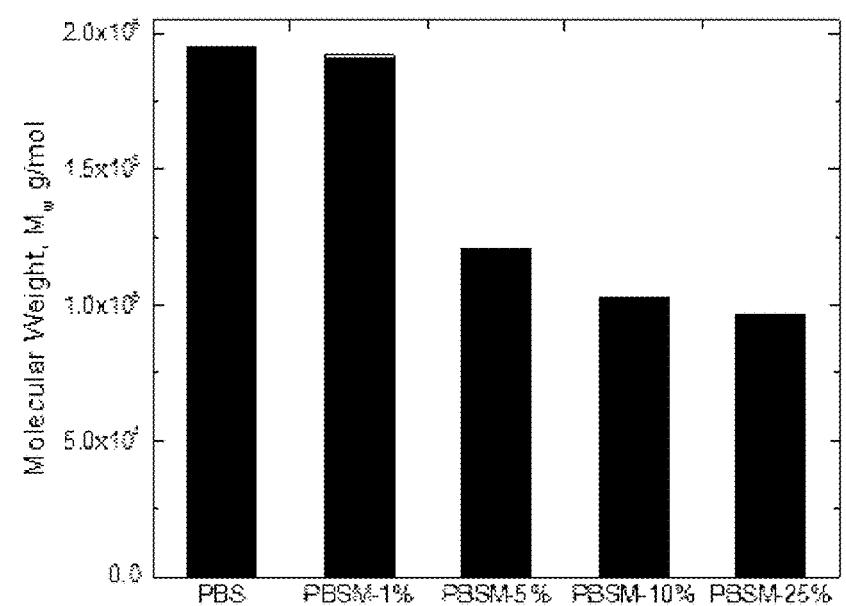
Figure 7:
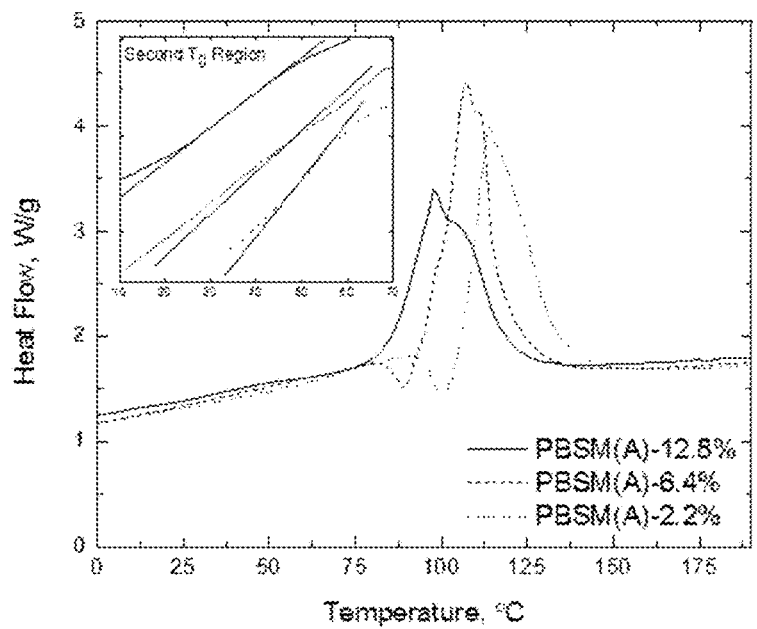
FIG. 7 illustrates (Panel A) Differential Scanning calorimetry scan at an elevated heating rate of 50° C./min for the poly(butylene succinate) homopolymer and poly(butylene succinate-co-muconate) copolymer at 25% loading, according to some embodiments of the present disclosure. The elevated ramp rate was used to elucidate the two glass transition temperatures present in the copolymer, as indicated by the dotted black lines.
Figure 7:
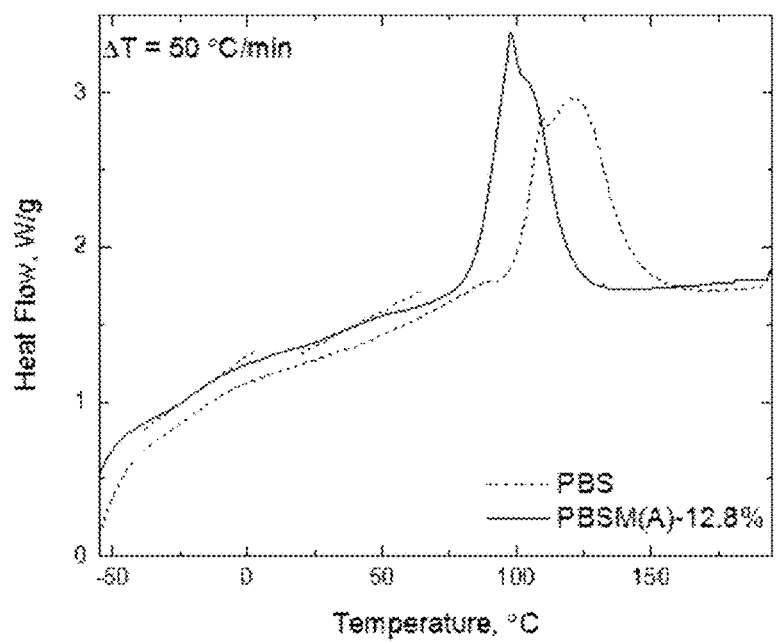

GPC chromatograms for the PBSM copolymers are presented in FIG. 6, Panel A. The results clearly show decreasing total molecular weight in the resultant copolymers with increasing muconic acid charge in the reactor. Muconic acid incorporation leads to copolymers with thermal properties that were distinct from the corresponding homopolymers. As an example of these changes, FIG. 7, Panel A shows the DSC trace for the second heating of PBS and PBSM-25%. These data show an emergence of a second $T_g$—this phenomenon is present at all levels of muconic acid incorporation into the starting PBS homopolymer. The strength of this $T_g$ and its location of emergence depend on the amount of muconic acid incorporated into the final copolymer. This effect is further demonstrated by the decreasing $T_m$ with increasing muconic acid content shown in FIG. 7, Panel B. This melting point depression phenomena is reminiscent of eutectic-like behavior. The lower glass transition temperatures increased as the number of muconic acid groups in the copolymer increased. This increase can be rationalized along the lines of well-known structure property relationships: namely, the muconic unit inhibits bond rotation in the polymer backbone and is expected to retard segmental motion, thus increasing $T_g$. At the same time, the structural dissimilarity of the muconic group and its random placement disrupts crystalline packing leading to less perfect crystals and therefore decreased $T_m$.

Figure 8:
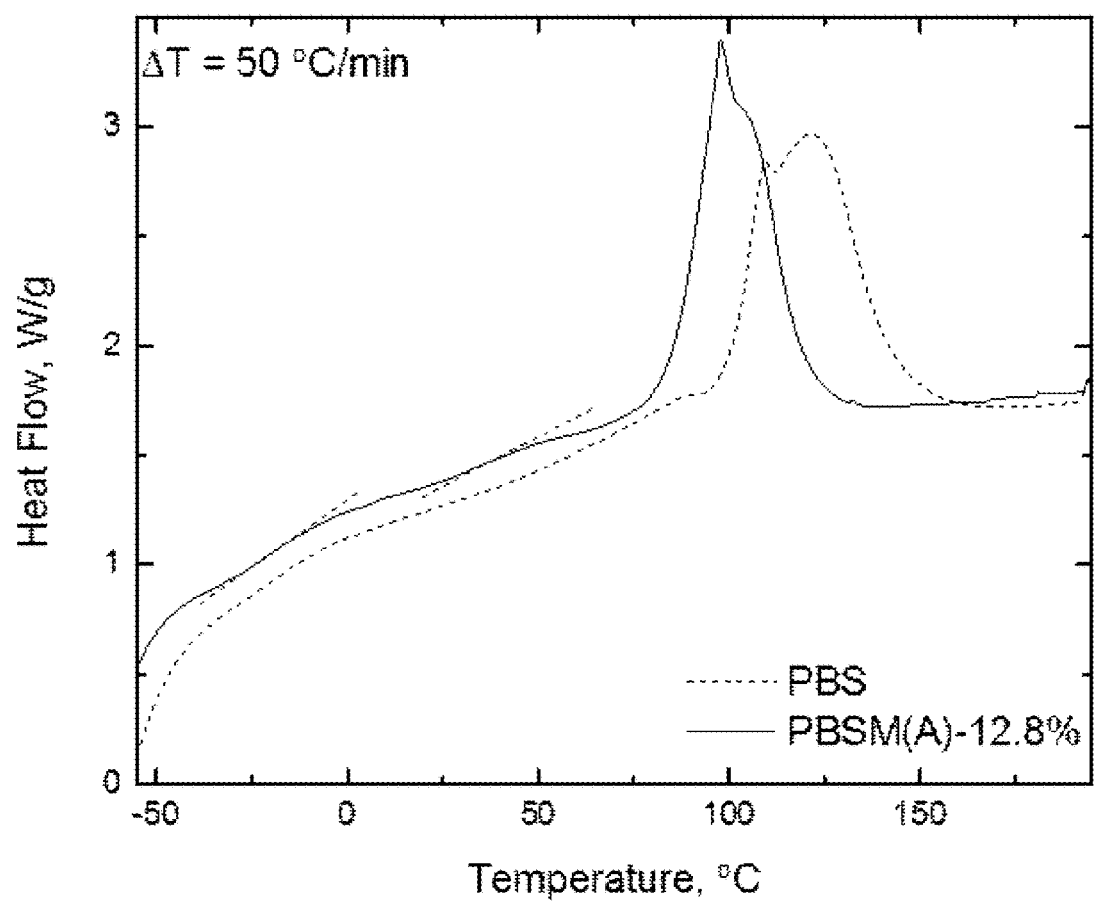
FIG. 8 illustrates TGA traces of the poly(butylene succinate-co-muconate) melts demonstrating a lowering of the degradation temperature with increasing incorporation of muconic acid into the copolymer, according to some embodiments of the present disclosure.

TGA results for the PBSM copolymers are presented in FIG. 8. As expected, incorporation of reactive double bonds leads to decreased thermal stability. Increasing the amount of unsaturation in the copolymer backbone led to lower $T_{D,50}$ values. Both thermal and molecular weight data for the copolymers are summarized in Table 2.

TABLE 2

Copolymer muconic incorporation as determined via NMR, thermal properties determined via DSC and TGA, and molecular weight with PDI as determined by GPC. Initially muconic acid is loaded as 10 mol % of the total acid, or 5 mol % of total monomer concentration. The muconic acid incorporation is reported as a function of total polymer concentration.

| Homopolymer | Muconic Acid Loading (mol % acid) | Muconic Acid Incorporation (mol % acid units) | $T_m$ (° C.) | $T_g$ (° C.) | $T_{g,2}$ (° C.) | $T_{D,50}$ (° C.) | $\Delta H_f$ (J/g) | $M_w$ | PDI |
|---|---|---|---|---|---|---|---|---|---|
| Poly(ethylene succinate) | 10 | 4.6 | 103 | −9 | — | 420 | 66.2 | $4.0*10^4$ | 1.9 +/− 0.1 |
| Poly(propylene succinate) | 10 | 6.4 | 46 | −31 | — | 410 | 47.3 | $5.7*10^4$ | 1.9 +/− 0.1 |
| Poly(butylene succinate) | 1 | — | 129 | −30 | — | 425 | 65.2 | $1.92*10^5$ | 2.0 +/− 0.1 |
|  | 5 | 2.2 | 125 | −29 | 45 | 410 | 69.7 | $1.21*10^5$ | 2.0 +/− 0.1 |
|  | 10 | 6.4 | 123 | −18 | 42 | 390 | 73.2 | $1.03*10^5$ | 1.9 +/− 0.1 |
|  | 25 | 12.8 | 105 | −13 | 39 | 380 | 74.7 | $9.7*10^4$ | 1.9 +/− 0.1 |
| Poly(hexylene succinate) | 10 | 5.6 | 46 | −31 | — | 415 | 58.4 | $7.3*10^4$ | 1.9 +/− 0.1 |

Figure 9:
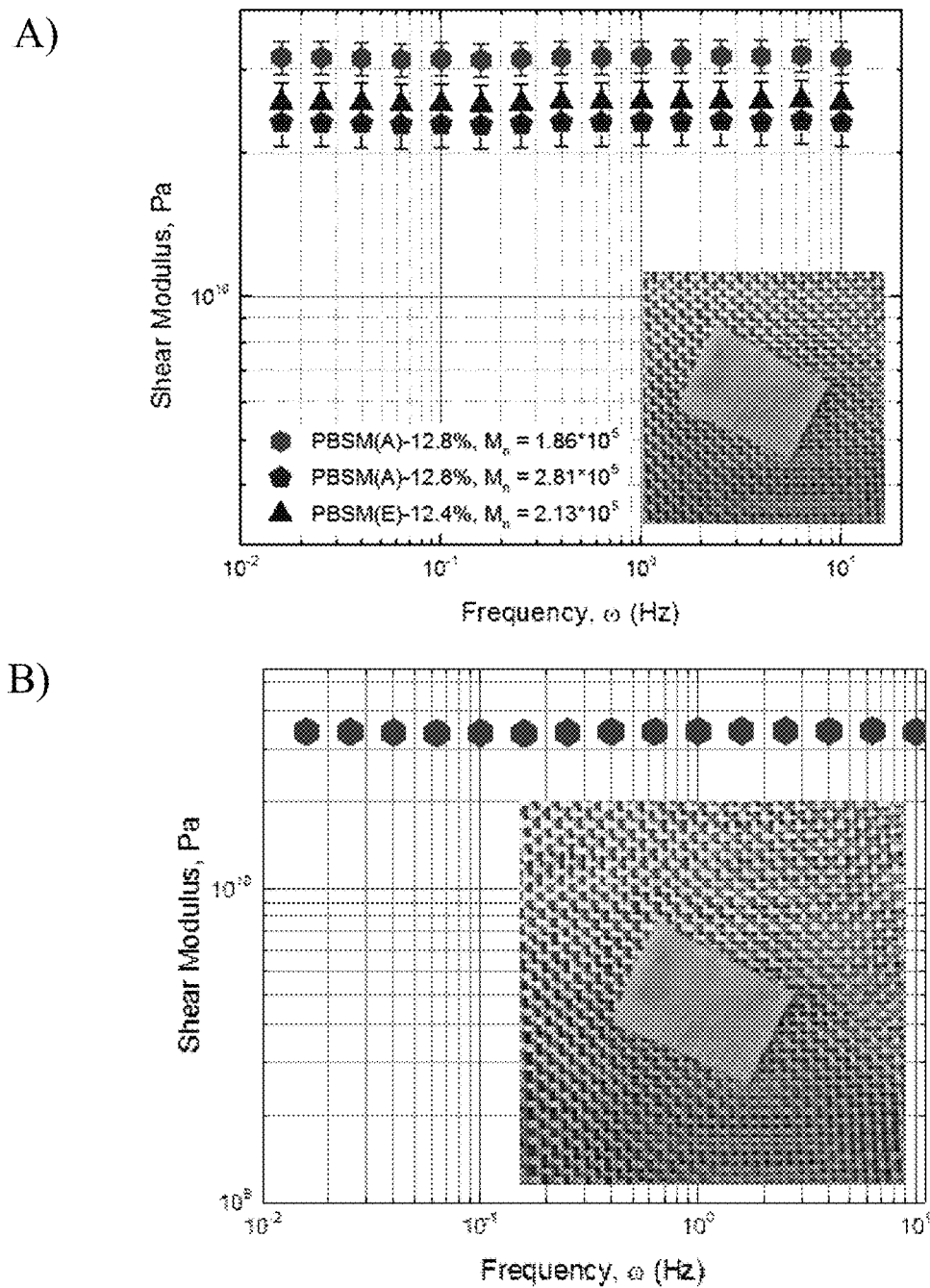
FIG. 9 illustrates shear modulus as a function of frequency for the synthesized composite, according to some embodiments of the present disclosure. Photo of the composites (insets) on top of a sheet of woven fiberglass.
Figure 10:
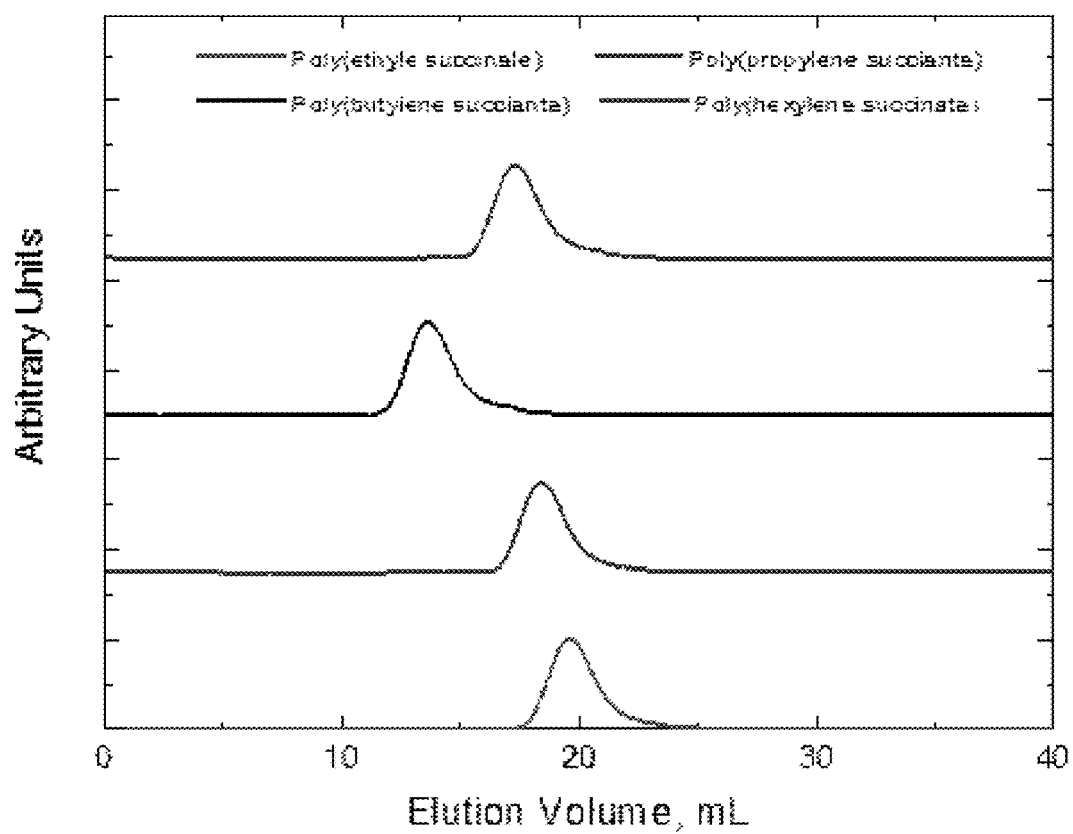
FIG. 10 illustrates GPC chromatographs for all synthesized homopolymers, according to some embodiments of the present disclosure. Poly(butylene succinate) possessed the highest molecular weight, as indicated by the lowest retention time.
Figure 11:
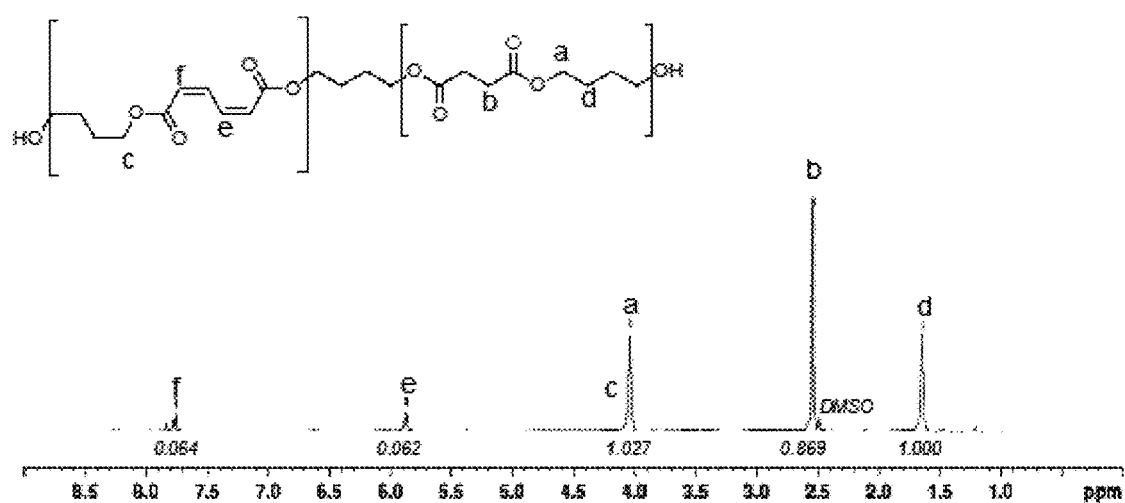
FIG. 11 illustrates Hydrogen-1 NMR for the poly(butylene succinate-co-muconate) 25% reactor charge, according to some embodiments of the present disclosure. The emergence of only two peaks between 5 and 7 ppm is indicative that the cis, cis conformation was maintained.
Figure 12:
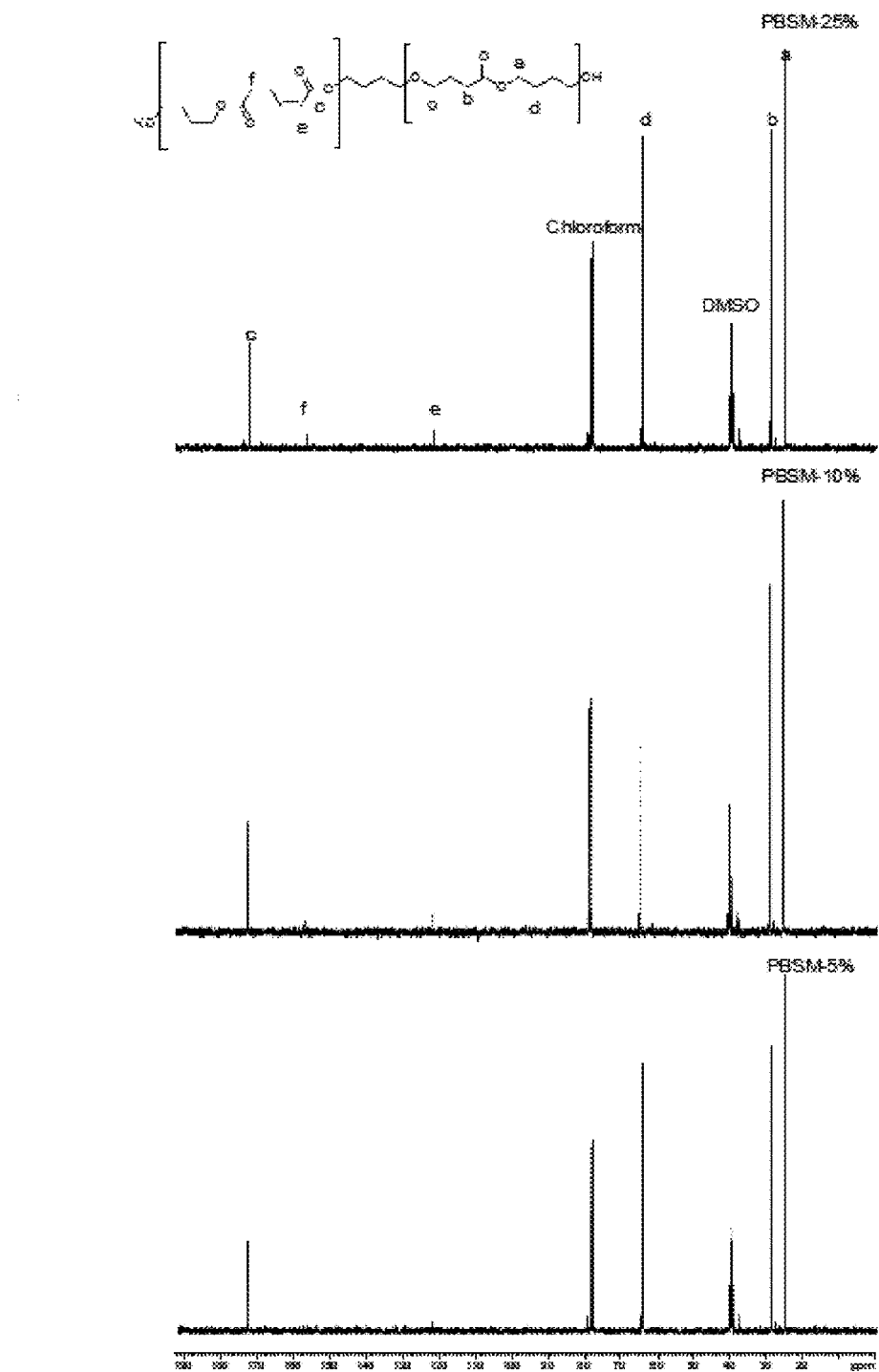
FIG. 12 illustrates Carbon-13 NMR for the three poly(butylene succinate-co-muconate) polymers in which the double bonds were detectable, according to some embodiments of the present disclosure. As the incorporation was increased the signal from the alkene carbons was increased.

In order to demonstrate the applicability of these new biobased polymers, a composite was made with the PBSM-25%, styrene, a diacrylate crosslinker (Sartomer 350), and AIBN (azobisisobutyronitrile) as an initiator. This resin mixture was applied to double ply fiberglass and pressed between two Teflon sheets at 80° C. The formulation is given in Table 3 and the reaction mechanism for cross-linking is depicted in Scheme 2, illustrating crosslinking poly(succinate-co-muconate) in which a crosslinker with a terminal vinyl group is reacted with the polymer to form a cross linked polymer network (resin). In this case R represents a benzene ring, making the crosslinker styrene. The mechanical properties of the composite were measured by dynamic mechanical analysis over a range of frequencies. FIG. 9 shows that the modulus is independent of frequency demonstrating that the composite behaves as an elastic solid rather than a viscoelastic polymer over the frequency range investigated. The measured shear modulus of 31.8 GPa is typical of fiberglass composites formed using copolymers. The composite exhibited a glass transition temperature of 90° C., a degradation temperature of 400° C., and no melting temperature.

Scheme 2

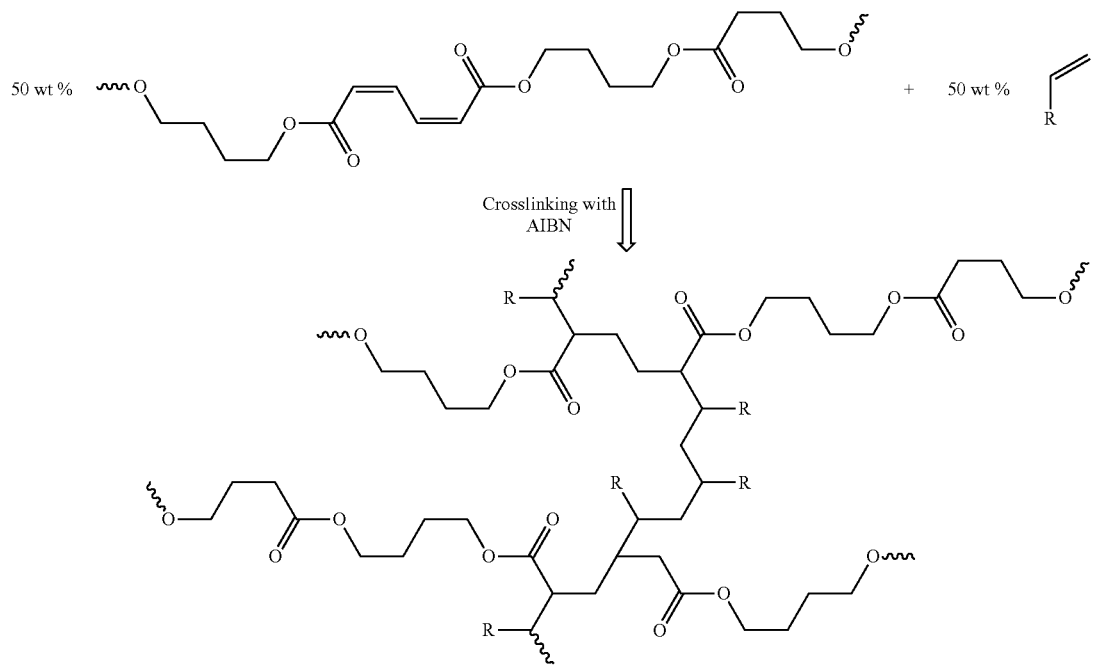

TABLE 3

Biobased copolymer fiberglass composite

| Property | Value |
| --- | --- |
| Fiberglass Loading | 68 wt. % |
| Resin | 32 wt. % |
| Biopolymer | 57.2 parts per hundred resin (pph) |
| Styrene | 41.0 pph |
| Diacrylate | 0.8 pph |
| AIBN | 1.0 pph |
| PBSM-25% Molecular Weight | $3.7*10^3$ |
| Shear Modulus | 31.8 GPa |
| Glass Transition, $T_g$ | 90° C. |
| Decomposition Temeprature, $T_{D, 50}$ | 400° C. |

Generally, the reaction conditions and assumption of equal reactivity of equivalent functional groups implies that all copolymers generated should be random copolymers. In fact, in the case of PES, PPS, and PHS there was no evidence of any non-random chain structure because only single $T_g$ are observed. However, in the case of the PBSM copolymers, two $T_g$ were observed and both exhibited compositional dependence. Without wishing to be bound be theory, the presence of two transition temperatures may be attributed to the muconic acid groups reacting, on average, later than the succinic acid thus leading to the muconic acid derived structural units being preferentially located nearer to the chain ends of the copolymer. It is postulated that the structure of the copolymer may be block-like, which could give rise to the second $T_g$. The block copolymer structure may result from the relative reactivity of succinic to muconic acid. PBS reacts readily and quickly attains high conversions. In contrast, due to resonance, steric hindrance, and poor solubility, muconic acid is likely less reactive. Due to these reactivity differences, the resulting block copolymer structure may contain PBS as the middle block and poly (butylene muconate) on the chain ends. However, the possibility of two separate molecular structures being present is discounted based on the GPC results (see FIG. 6, Panel A). Both indicate that only one molecular species was present in these examples. A separate elution peak or a broader molecular weight distribution (PDI>2) in the GPC trace could indicate separate polymer structures. In addition, when multiple species are present, a TGA typically shows step-wise degradation regions. FIG. 6, Panel B illustrates molecular weights for the homopolymers and copolymers as a function of muconic acid loading.

In creating the prototypical copolymer formulation and to ensure the solubility of the copolymer in styrene, a lower molecular weight PBSM copolymer was synthesized by limiting the reaction time. Table 3 details the formulation used to create the composite panel. The insets to FIG. 9 demonstrate that the resulting material has desirable aesthetic qualities while achieving a typical fiberglass modulus in excess of 30 GPa. This proof of concept testing conclusively demonstrates that muconic acid can be utilized in the development of sustainable, bio-renewable copolymers and/or resins.

In some embodiments of the present invention, a method is provided for incorporating muconic acid into homopolymers through the use of a "one pot" synthesis scheme for copolymerization that enables the solubility of muconic acid, while preventing its degradation during polymerization. It is difficult to react neat muconic acid directly with any diol. This is due to the high melting point of muconic acid (in its cis,cis form ~195° C. and in its trans,trans form 301° C.) and its poor solubility in a wide variety of solvent systems, including diols. Thus, it is difficult to polymerize muconic acid with butanediol across a range of temperatures (120° C. to 220° C.). At elevated temperatures (T>180° C.) the monomers degrade leaving the reaction mixture unrecoverable. At lower temperatures, the solubility of the muconic acid in the diol (presented in Table 4) is low such that, even after extended reaction times (>18 hours), negligible polymerization occurs.

TABLE 4 cis,cis Muconic Acid Solubility in various diols.
Overall, the solubility is poor is all diols.

| Diol | Solubility (mol ratio Muconic:Diol) |
|---|---|
| Ethylene Glycol | 0.258:1 |
| Propanediol | 0.103:1 |
| Butanediol | 0.0535:1 |
| Hexanediol* | — |

*Solid at room temperature, low solubility

Thus, the use of neat muconic acid does not readily allow for the polymerization of a polymer. In order to incorporate muconic acid into homopolymers, muconic acid may be reacted with another homopolymer system (e.g., PBS, PHS, PPS, PES) to create a copolymer. Initially, all the muconic acid is charged into the reactor and a small amount of muconic acid is solubilized in the homopolymer reaction mixture. As the reaction proceeds, muconic acid is consumed allowing for additional muconic acid to be consumed. Furthermore, muconic acid has a higher solubility in the preformed polymer. The consumption of muconic acid as the reaction progresses and the additional solubility provided by the preform polymer enables the muconic acid copolymers to be formed, up to 1-25% reactor charge loading as presented in Table 5.

TABLE 5

Synthesized poly(butylene succinate-co-muconate) copolymers,
the amount that was recovered from the polymerization
mixture, and their molecular weight. Mass recovery computed
via mol balance and absolute molecular weight determined
via GPC with light scattering detection.

| Reactor Charge (mol %) | | | | | |
|---|---|---|---|---|---|
| Butanediol | Succinic Acid | Muconic Acid | % Mass Recovery | $M_w$ | PDI |
| 50 | 50 | 0 | 99% | $1.95*10^5$ | 2.0 +/− 0.1 |
| 50 | 0 | 50 | 0.0 | — | — |
| 50 | 49.5 | 0.5 | 99% | $1.92*10^5$ | 2.0 +/− 0.1 |
| 50 | 47.5 | 2.5 | 95% | $1.21*10^5$ | 2.0 +/− 0.1 |
| 50 | 45 | 5 | 94% | $1.03*10^5$ | 1.9 +/− 0.1 |
| 50 | 37.5 | 12.5 | 92% | $9.7*10^4$ | 1.9 +/− 0.1 |
| 50 | 25 | 25 | 0.0 | — | — |

Poly(butylene succinate-co-muconate) copolymer was incorporated into a fiber glass resin. Selecting a suitable molecular weight for the unsaturated homopolymer assists incorporation of the copolymer into the fiberglass mat. A lower molecular weight homopolymer, synthesized by limiting the reaction time, enabled the copolymer to become the primary component in the mixture (presented in Table 6) and subsequently was largely incorporated into the fiberglass mat. Without muconic acid, or sufficient mat uptake, the composite could not be formed. Shorter reaction times (<1.5 hours) resulted in low molecular weight oligomers that were insufficiently recovered from the reaction mixture. The presented formulation optimizes molecular weight vs. styrene solubility to ensure ideal properties.

TABLE 6

Biobased copolymer fiberglass composite
uptake and styrene loading as a function

| Sample | PBSM-25% Molecular Weight | Styrene Loading | Fiber Glass Uptake |
|---|---|---|---|
| 3 Hour Reaction | $3.7*10^3$ | 41 wt. % | Yes |
| 5 Hour Reaction | $1.2*10^4$ | 73 wt. % | Poor |
| 12 Hour Reaction | $9.7*10^4$ | 89 wt. % | Poor |

First Materials and Methods

Materials: Succinic acid, butanediol, ethylene glycol, propanediol, hexanediol, chloroform, methanol, azobisisobutyronitrile and titanium (IV) butoxide were purchased from Sigma Aldrich. To ensure high purity, succinic acid was recrystallized from acetic acid. All diols were purified by vacuum distillation. Purity was confirmed by measuring melting points using DSC to be greater than 99.8% for all monomers.

Biological Production of Muconic Acid: cis,cis-muconic acid was produced biologically with an engineered strain of *Pseudomonas putida*, KT2440-CJ102, using benzoate as the precursor substrate. The cells produced muconic acid at titers of 34.5 g/L and approximately recover 28.1 g/L. Purity, as determined via DSC, was found to be greater than 99.5%.

Polymerizations: Polymerizations were conducted in three-necked round bottom flasks with an overhead Arrow 750 stirring motor. The three-necked round bottom flask was connected to a dean-stark trap connected to a water-cooled condenser and vacuum line. Initially the reactor was charged with the reactants at a molar ratio of 1.1 to 1 of dicarboxylic acid to diol. Temperature of the reaction vessel was raised to 150° C. for two hours under a purging nitrogen flow. Oligomers were formed during the first two hours of reaction. At the two hour mark, titanium (IV) butoxide catalyst was added to the reaction mixture at 0.1 wt % and vacuum was applied to bring the total pressure below 50 torr. The reactor temperature was then raised to 220° C. and the reaction was allowed to proceed for an additional ten hours. The catalyst encourages the condensation reaction of the monomers and transesterification between chains thus favoring the development of the most probable distribution. After ten hours the motor was stopped and the reaction was allowed to cool to room temperature while still under vacuum. The polymer was then dissolved in chloroform and subsequently precipitated by using a twofold volume of methanol. The precipitate was filtered out and dried in a vacuum oven for 48 hours.

Fiberglass Composite: The composite material was produced from the 25% loaded poly(butylene succinate-co-muconate) with styrene as the crosslinking component, Azobisisobutyronitrile (AIBN) was used as a photoinitiator. Aand woven fiberglass was obtained from Bondo. The resin mixture comprised of 50 wt. % unsaturated polyester, 48.5 wt % styrene, 1 wt % Sartomer 350, and 0.5 wt % AIBN. The resin mixture was purged with nitrogen for five minutes and subsequently applied to the two pieces of fiberglass. The resin soaked fiberglass sheets were placed between two Teflon sheets on a hot plate with a heated to 80 C and allowed to react for 4 hours. Subsequently the composite was removed from the mold and placed in a vacuum oven for 24 hours to remove any excess unreacted styrene.

Thermal Measurements: Thermal properties were ascertained using a TA Instruments Q-5000 Digital Scanning calorimeter (DSC) with aluminum hematic pans and using a TA Instruments Q-500 Thermal Gravimetric Analyzer (TGA) with platinum pans. All DSC and TGA scans were run at a heating rate of 10° C./min unless otherwise noted.

Molecular Weight Determination: Molecular weights and polydispersities were ascertained using a Wyatt Instruments gel permeation chromatography system with light scattering detection for absolute molecular weight measurement. A constant value of the specific refractive index increment of (dn/dc)=0.05 ml/g was adopted. HPLC grade chloroform was used as the carrier solvent.

NMR: Structure was determined via NMR using a JEOL ECA 500 MHz liquid-state NMR spectrometer. All $^{13}$C NMR spectra were recorded under proton decoupling with 2 s relaxation delay. For both homopolymers and copolymers, deuterated chloroform was mixed with deuterated dimethyl sulfoxide and used in a volume ratio of 2:1 for the solvent.

Mechanical Testing: Modulus values for the composite material were determined using a Rheometric ARES-LS Rheometer using torsional rectangular geometry fixtures. A rectangular sample having dimensions of 12.5×5.0×2.0 mm was cut from the sheet using an Isomet diamond saw.

The properties of poly(butylene succinate)-based copolymers incorporating maleic anhydride were used as a baseline for comparison against copolymers derived from fumaric acid, cis,cis-muconate, and trans,trans-muconate, all of which may be obtained biologically. The resulting biobased copolymers were combined with styrene, methacrylic acid, or a mixture of methacrylic acid and cinnaminic acid, infused into woven fiberglass and cross-linked with the addition of a free-radical initiator and heat. This process produced a series of partially or fully bio-derived composites. Overall, the muconate-containing copolymer systems exhibited a more favorable property suite than the maleic anhydride and fumaric acid counterparts. In all cases at the same olefinic monomer loading, the trans,trans-muconate polymers exhibited the highest shear modulus, storage modulus, and glass transition temperature indicating stronger and more thermally resistant materials. They also exhibited the lowest loss modulus indicating a greater adhesion to the glass fibers. The use of a mixture of methacrylic and cinnaminic acid as the reactive diluent results in a FRP composite with properties that can be matched to reinforced composites prepared with styrene. Significantly, at one-third the monomer loading (corresponding to two-thirds the number of double bonds), trans,trans-muconate produced approximately the same storage modulus and glass transition temperature as maleic anhydride, while exhibiting a superior loss modulus. Overall, this work demonstrates the novel synthesis of performance-differentiated FRP composites using renewably-sourced monomers and polymers. Combining a fully renewable copolymer with a bio-derived reactive diluent enables the production of a fully renewable resin system for the manufacturing of composites.

Figure 13:
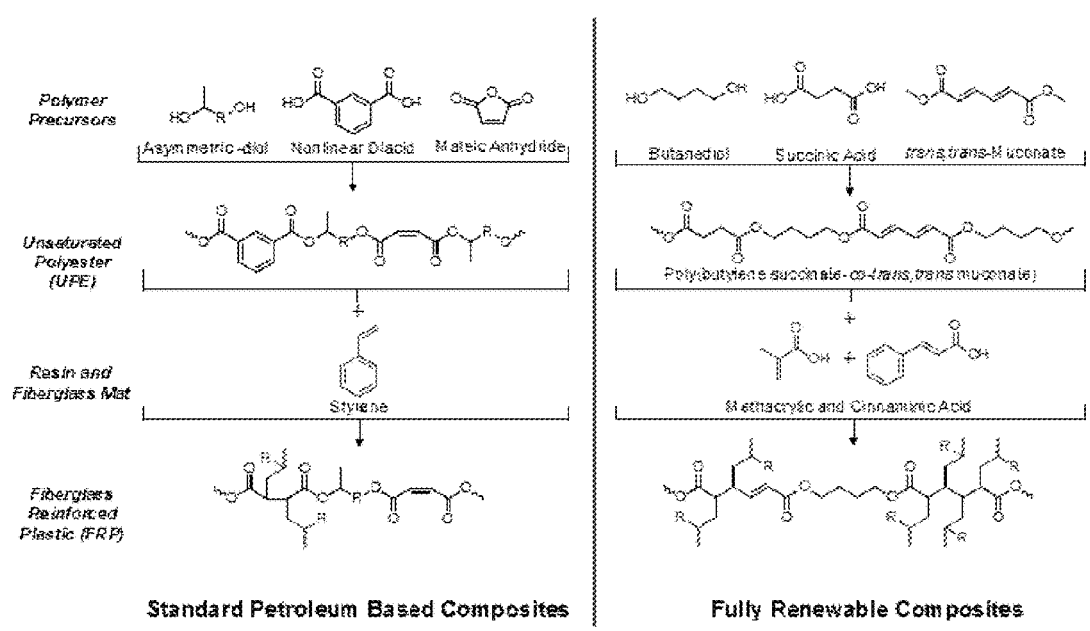
FIG. 13 illustrates the methodology used in this disclosure; (left) a typical industrial FRP fabrication method in which maleic anhydride is polymerized with asymmetric monomers to form a copolymer that is subsequently dissolved in styrene to produce a resin for infusion into a fiber mat and reacted to form a composite; (right) renewably-sourced resins are synthesized from butanediol, succinic acid, and an olefinic monomer (i.e. trans,trans-muconate, cis,cis-muconate, or fumarate) at various loadings combined with methacrylic and cinnaminic acid, according to some embodiments of the present disclosure; upon infusion and reaction, a robust composite was formed.

One metric ton of bio-based materials saves, relative to conventional materials, 55 gigajoules of primary energy and 3 tons of $CO_2$ equivalents. Given this expected benefit, the current study details the use of monomers obtainable from lignocellulose to realize the synthesis of a 100% renewably-sourced composite resin systems. FIG. 13 illustrates an approach wherein bio-derived diacids and diols are combined to synthesize bioderived polymers and subsequently combined with a bio-derivable reactive diluent. PBS was selected as the base renewably-sourced homopolymer into which the olefinic monomers were incorporated because it is commercially available, of relatively low cost, has a robust thermal profile, and exhibits compatibility with styrene. Initially, a family of copolymers produced from the incorporation of maleic anhydride, fumaric acid, cis,cis-muconate ester, and trans,trans-muconate ester into PBS at various loadings were synthesized and their properties are disclosed herein. Subsequently, this family of copolymers was cross-linked with styrene, methacrylic acid, and a blend of methacrylic and cinnaminic acid in the presence of woven fiberglass mats to produce a series of composites. The fiberglass-reinforced polymers (FRPs) were tested for thermal and mechanical properties to understand the effects of incorporating the different olefinic monomers. Overall, this work demonstrates the successful implementation of bio-derived monomers in performance-differentiated FRP composites.

Figure 14:
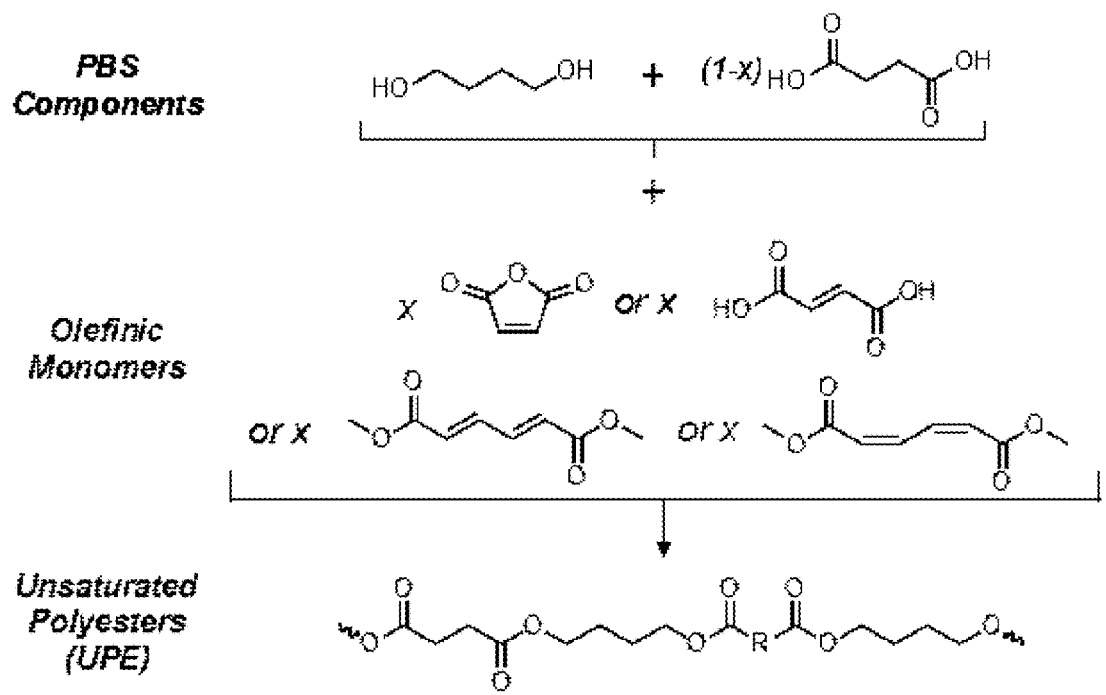
FIG. 14 illustrates initial copolymer synthesis in which the copolymer contained 1 molar equivalent of butanediol to 1 molar equivalent of total succinic acid and olefinic monomers, according to some embodiments of the present disclosure. The amount of olefinic monomer was varied from 0 to 1. The mole fraction of the olefinic monomer is the x-axis in the majority of the subsequent figures.

Results:

Initial Copolymer Synthesis:

As illustrated in FIG. 14, all copolymers were synthesized by loading a polymerization reactor with 1 molar equivalents of butanediol to 1 molar equivalent of succinic acid and olefinic monomer combined. PBS was selected as the homopolymer for muconate incorporation due to its ductility, toughness, and capability of being synthesized from monomers obtained from lignocellulose. The ratio of succinic acid to olefinic monomer was varied and olefinic incorporation into the final polymer was determined via $^1$H NMR. Table 7 below reports the initial reactor stoichiometry for each copolymer synthesized, the molecular weight of the final polymers, measured olefinic incorporation, and in the case of maleic anhydride and cis,cis-muconate, the degree of isomerization, and reaction yield. In all cases, the incorporation of the olefinic monomers in the final copolymer was near stoichiometric, all copolymers achieved high molecular weights near or above 100,000 Da, and there was no isomerization of the trans monomers (trans,trans-muconate and fumaric acid).

TABLE 7

Molecular properties of the synthesized FRPs. Isomerization is reported as the total of the diacid the isomerized.

| Olefinic Monomer | % of Diacid Loading | Incorporation | $M_w$ (×10$^{-6}$) | PDI | Isomerization (cis,cis to cis,trans) | Isomerization (All cis to all trans) | Yield (mass basis) |
|---|---|---|---|---|---|---|---|
| Maleic Anhydride | 10 | 9.8 | 1.95 | 2.0 ± 0.1 | — | 1 | 96% |
| | 25 | 25.6 | 1.89 | 2.0 ± 0.1 | — | 5 | 97% |
| | 50 | 49.7 | 1.70 | 2.0 ± 0.1 | — | 7 | 92% |
| | 75 | 74.3 | 1.61 | 2.0 ± 0.1 | — | 11 | 89% |
| | 100 | 100 | 1.54 | 2.0 ± 0.1 | — | 12 | 93% |
| Fumaric Acid | 10 | 10.2 | 1.97 | 2.0 ± 0.1 | — | — | 96% |
| | 25 | 24.2 | 1.82 | 2.0 ± 0.1 | — | — | 93% |
| | 50 | 47.1 | 1.57 | 2.0 ± 0.1 | — | — | 95% |
| | 75 | 77.2 | 1.42 | 2.0 ± 0.1 | — | — | 91% |
| | 100 | 100 | 1.31 | 2.0 ± 0.1 | — | — | 86% |

TABLE 7-continued

Molecular properties of the synthesized FRPs. Isomerization is reported as the total of the diacid the isomerized.

| Olefinic Monomer | % of Diacid Loading | Incorporation | $M_w$ ($\times 10^{-6}$) | PDI | Isomerization (cis,cis to cis,trans) | Isomerization (All cis to all trans) | Yield (mass basis) |
|---|---|---|---|---|---|---|---|
| cis,cis Dimethyl Muconate | 10 | 9.6 | 1.91 | 2.0 ± 0.1 | — | — | 95% |
| | 25 | 23.7 | 1.78 | 2.0 ± 0.1 | 5 | 1 | 93% |
| | 50 | 50.1 | 1.32 | 2.0 ± 0.1 | 10 | 3 | 90% |
| | 75 | 76.2 | 1.21 | 2.0 ± 0.1 | 19 | 6 | 85% |
| | 100 | 100 | 1.01 | 2.0 ± 0.1 | 21 | 4 | 87% |
| trans,trans Dimethyl Muconate | 10 | 9.8 | 1.95 | 2.0 ± 0.1 | — | — | 97% |
| | 25 | 24.1 | | 2.0 ± 0.1 | — | — | 96% |
| | 50 | 50.3 | | 2.0 ± 0.1 | — | — | 91% |
| | 75 | 76.2 | | 2.0 ± 0.1 | — | — | 89% |
| | 100 | 100 | 1.26 | 2.0 ± 0.1 | — | — | 90% |

Figure 15:
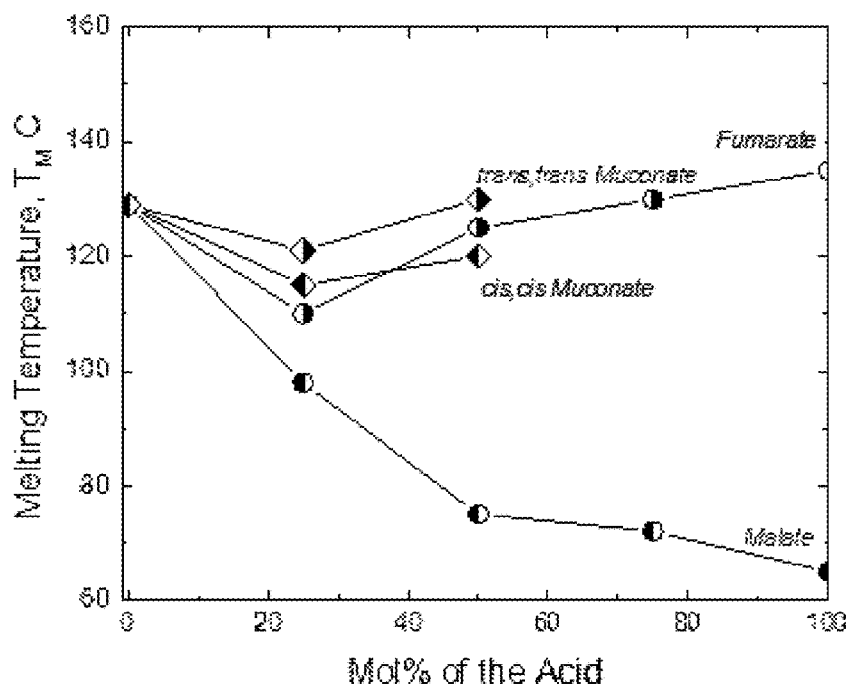
FIG. 15 illustrates (Panel A) melting temperature and (Panel B) glass transition temperature determined via DSC for the copolymers, according to some embodiments of the present disclosure, as a function of olefinic monomer loading. On the x-axis, 0% is homogeneous PBS and 100% is the olefinic homopolymer with butanediol. With the exception of the maleic anhydride copolymers, the copolymers exhibited eutectic melting behavior, and the muconate copolymers were amorphous as they approach the homopolymer composition. As the olefinic incorporation increased, the Tg is increased due to the presence of rigid groups in the backbone. At higher loadings, a second, higher Tg emerged in the cis,cis- and trans,trans-muconate polymers. In all cases, the malate copolymers exhibited the lowest Tg followed by fumarate, cis,cis-muconate and finally trans,trans-muconate with the highest Tg.
Figure 15:
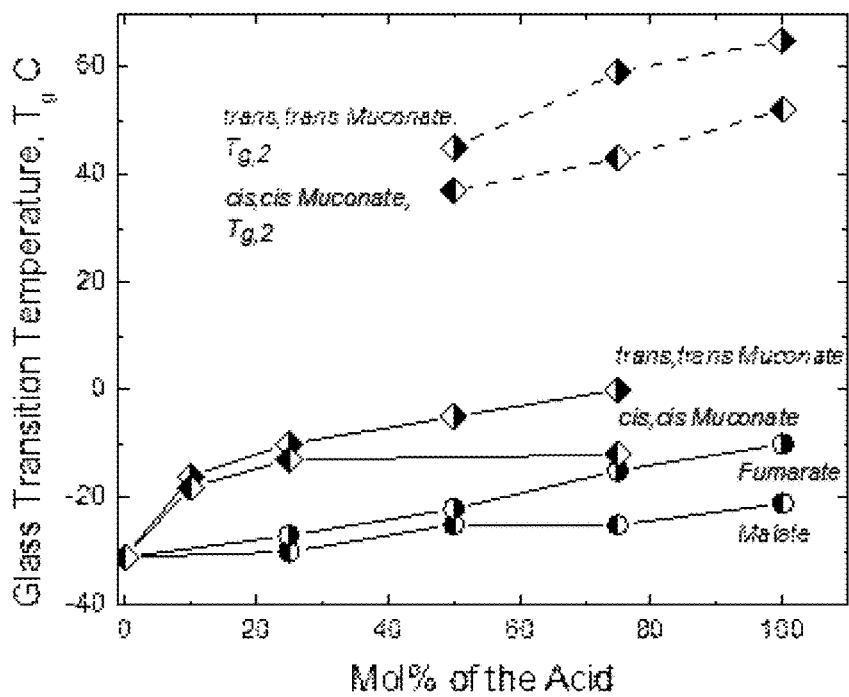
Figure 16:
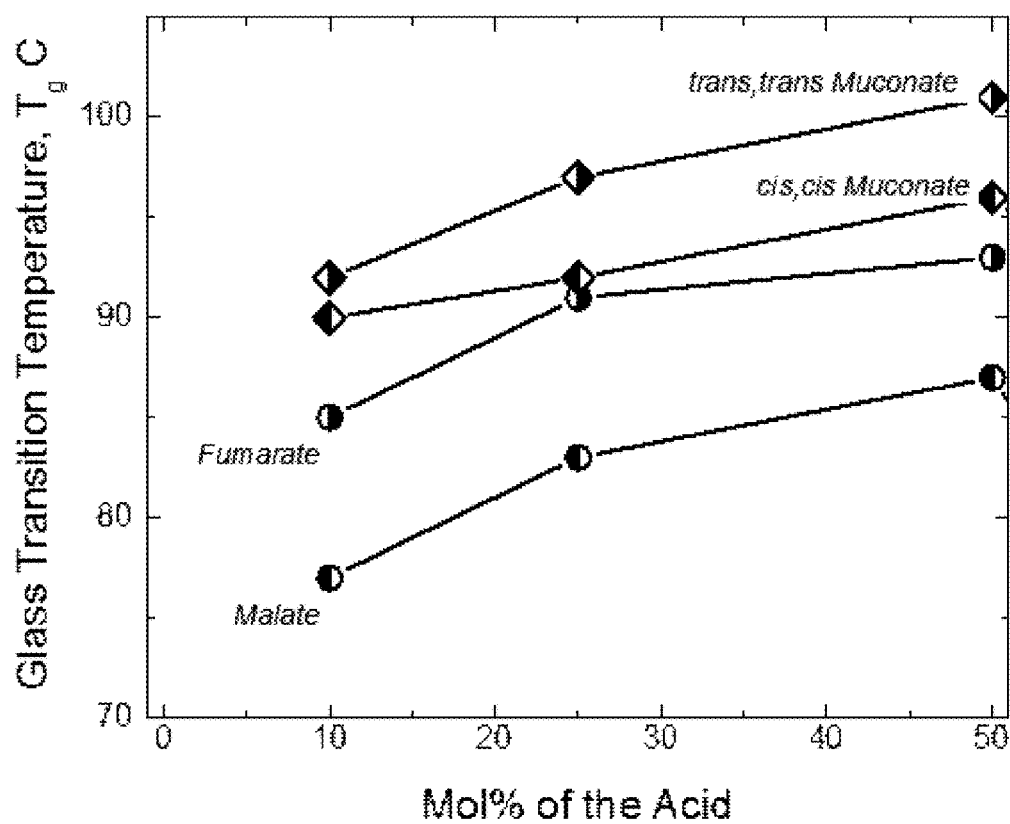
FIG. 16 illustrates glass transition temperature determined via DSC using a heating rate of 50° C./min as a function of olefinic monomer loading for the styrene-based composites. The same trends from the copolymer Tg measurements were observed in the FRPs. Above 50% olefinic diacid loading, the composite exhibited poor thermal performance and extreme plasticizing.

Thermal properties of the polymers were measured. FIG. 15 shows the melting point ($T_m$) of the copolymers. High molecular weight PBS exhibited a melting point between 120 and 130° C. At low olefinic loadings of muconate and fumarate, there was an initial decrease in the melting temperature associated with eutectic melting point depression followed by an increase in $T_m$ possibly due to the rigidity of muconate or pi stacking interactions. Maleic anhydride exhibited a continuous decrease in $T_m$, while fumaric acid and both isomers of muconate exhibited a $T_m$ increase. Above 50% loading, the isomers of muconate exhibited no melting temperature, indicating that they were amorphous polymers. Additionally, all the copolymers demonstrated an increasing glass transition temperature ($T_g$) with increasing olefinic monomer incorporation, also presented in FIG. 16. In general, the copolymers with muconate possess a higher $T_g$ than the other olefinic monomers due to the presence of two double bonds over one. Additionally, the trans-configuration resulted in a higher $T_g$ due to its likely more extended configuration and thus higher crystallinity. The muconate-incorporated copolymers also possessed a second $T_g$ at higher loadings, which has been observed for copolymers containing a butanediol-muconate subunit. In all cases, the muconate monomers were more favorable for composite implementation than fumaric acid and maleic anhydride given their higher $T_g$ and high melting points, indicating that they are well suited for applications that require ductility, toughness, and thermal resistance.

Figure 17:
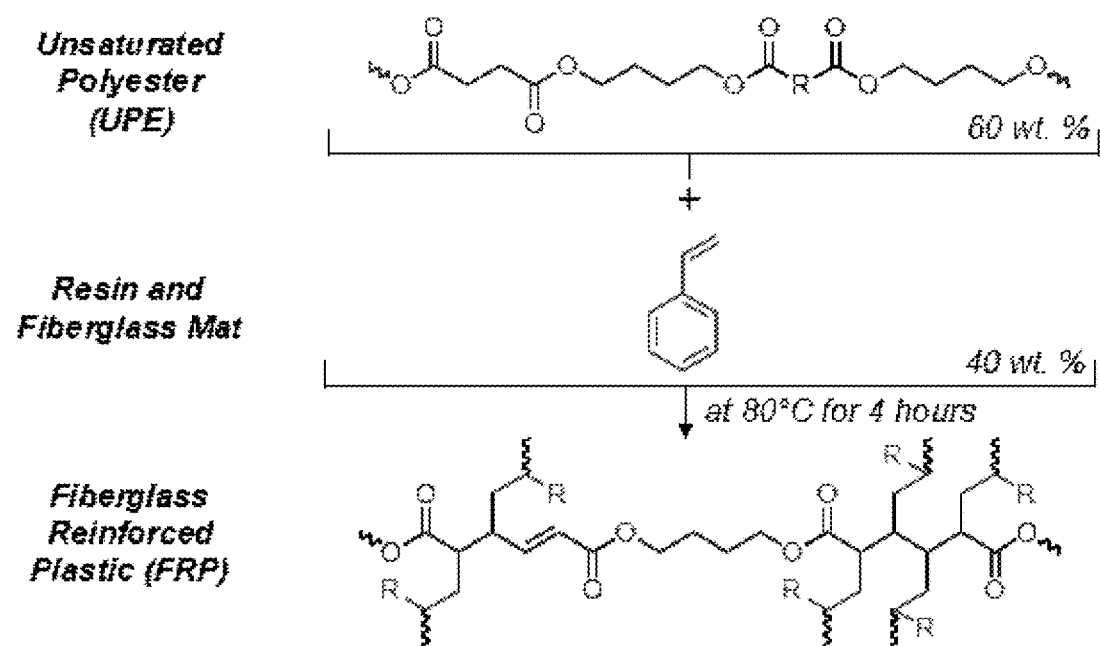
FIG. 17 illustrates initial FRP formation in which the bio-copolymer, according to some embodiments of the present disclosure, was dissolved in styrene, infused into a fiberglass mat, and cured to form an FRP, according to some embodiments of the present disclosure.

Styrene Composites:

To assess the performance of the synthesized copolymers as a drop-in replacement for commercial copolymers and evaluate the differentiating performance of muconate, the copolymers were initially synthesized at a lower molecular weight (<40,000 Da) and followed by dissolution in styrene and subsequent cross-linking around a 2-ply woven fiberglass mat, as illustrated in FIG. 17. The mechanical and thermal properties of the resulting FRPs were then evaluated. No composite exhibited a melting temperature, indicating that crystallization kinetics were inhibited as the thermosets were formed. Generally, the shear and dynamic storage modulus were measured of the stiffness of the composites, while the loss modulus was used to probe adhesion of the copolymer/resin mixture to the glass fiber surfaces within the fiberglass mat. In addition to exhibiting no $T_m$, all the FRPs exhibited an increased $T_g$ from their initial copolymer due to the formation of the thermoset (crosslinking restricts molecular motion). In all cases, as the loading of the olefinic monomer was increased, the $T_g$ increased, as presented in FIG. 16. The increase in the FRP $T_g$ is associated with the increasing $T_g$ of the starting copolymer, the high crosslink density in the thermoset, and any additional restrictions on molecular motion associated with the fiber presence. As in the case of the pure copolymers, the trans,trans-muconate FRPs exhibited the highest $T_g$s, followed by cis,cis-muconate, fumaric acid, and maleic anhydride. A higher $T_g$ is desirable as it results in FRPs that can be used across a wider range of temperatures and in general, materials with a higher $T_g$ should exhibit higher shear and storage moduli at a given service temperature.

Figure 18:
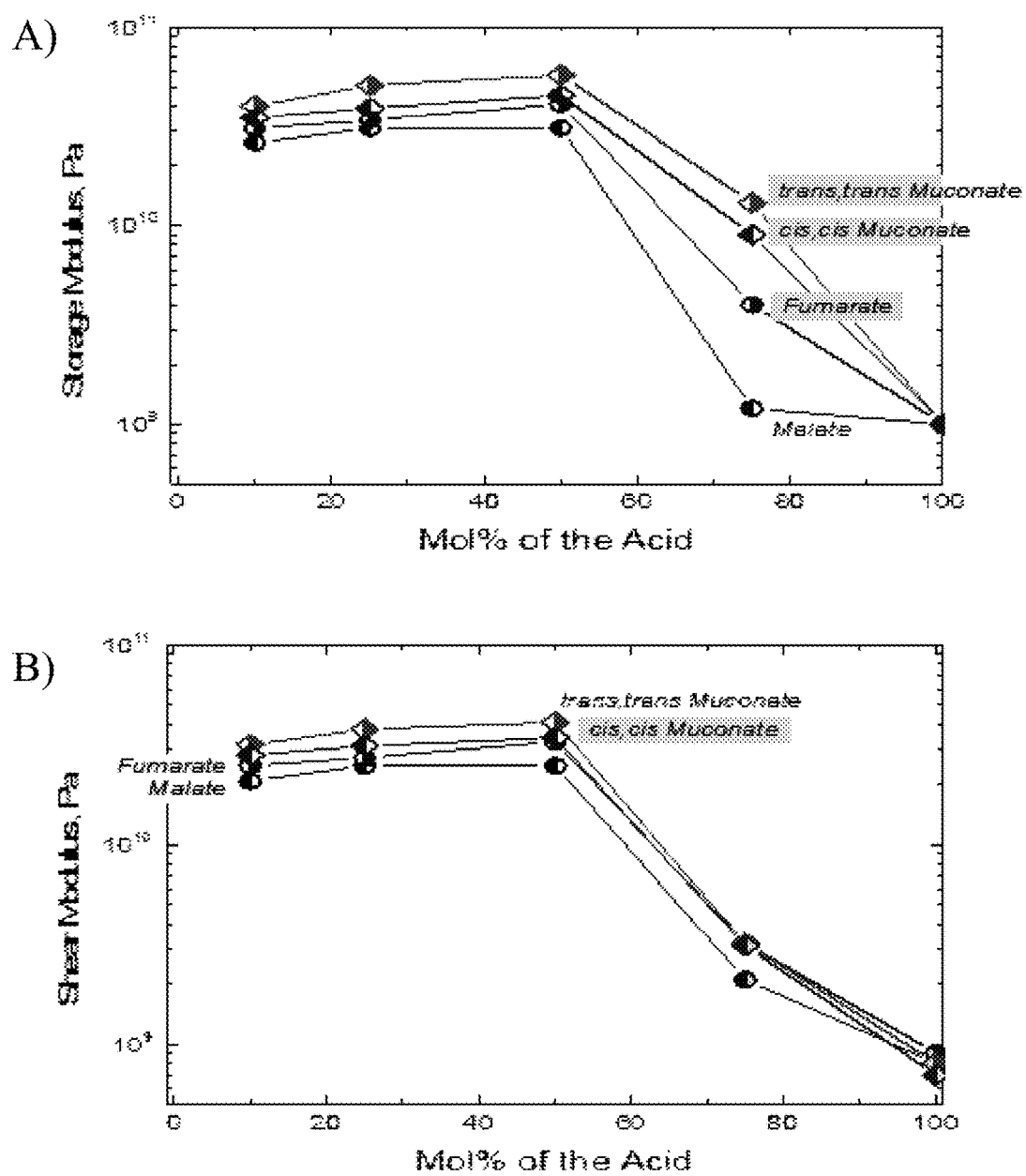
FIG. 18 illustrates the dynamic storage (Panel A) and complex shear moduli (Panel B) of various styrene FRPs, according to some embodiments of the present disclosure, at 1 Hz and 30° C. as a function of olefinic loading. As the loading of the olefinic diacid increased up to 50%, the storage and shear moduli increased for all copolymers. Above 50%, all of the copolymers in exhibited incompatibility with styrene (indicated in red shading). The trans, trans-muconate polymers exhibited the highest storage and shear moduli followed by the cis,cis-muconate, fumarate, and malate copolymers.

The FRPs exhibited mechanical behavior that depends on the olefinic monomer loading; in most cases, the FRPs demonstrated frequency/shear independent behavior. In the case of the storage and shear moduli, as presented in FIG. 18, the FRPs exhibited an increase in their moduli up to ~50% olefinic monomer loading. Below 50%, all FRPs exhibited high moduli (on the order of 30-50 GPa) that are typical of commercials FRPs. However, above 50% loading, the copolymer lost compatibility with the reactive diluent and low-quality FRPs were formed. This lack of compatibility may be attributed to the high crystallinity of the olefinic units, compared to the asymmetric/non-linear units that are implemented in industrial practice. In all cases, the trans,trans-muconate copolymers exhibited the best performance in the FRP followed by the cis,cis-muconate, fumaric acid, and maleic anhydride copolymers. The differences between the composite formulations were less pronounced in the complex shear modulus, which is equal to the square root of the sum of the squares of the dynamic storage and loss moduli. Without wishing to be bound by theory, the improved performance of the trans,trans-muconate FRP may be attributed to the high $T_g$ of the starting copolymer (see FIG. 15), to its olefinic bonds in the trans-configuration, and to the potentially higher degree of cross-linking provided by two olefinic bonds per monomer unit. In the styrene composites, there was no instance in which a maleic anhydride-FRP, nor the fumaric acid and cis,cis-muconate FRPs, exhibited storage or shear modulus that matched or exceeded that of the trans,trans-muconate FRPs.

Figure 19:
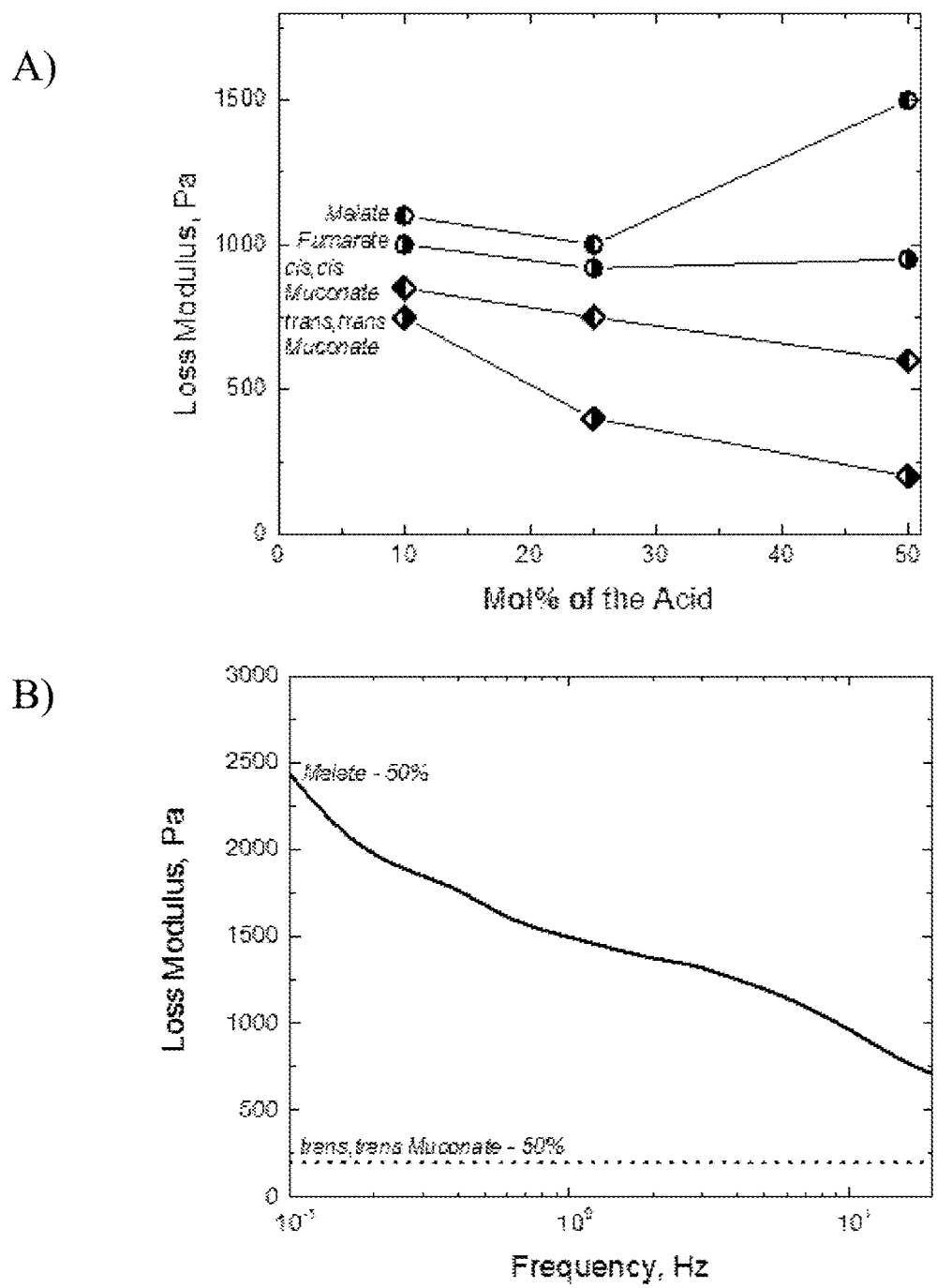
FIG. 19 illustrates the loss modulus of the styrene FRPs, according to some embodiments of the present disclosure, at 1 Hz as a function of olefinic loading. As the loading of the olefinic diacid increased up to 50%, the loss modulus decreased for all copolymers except the malate copolymers. Above 50% (not shown), all of the copolymers exhibited incompatibility with styrene and the loss modulus increased and exhibits shear-dependent behavior (Panel A). The trans, trans-muconate copolymers exhibited the lowest loss modulus followed by the cis,cis-muconate, fumarate, and malate copolymers (Panel B).

While the storage and shear moduli demonstrate the stiffness of the final copolymer, the loss modulus probes the adhesion of the resin mixture to the fiberglass mat. The loss modulus is an indication of how much energy is dissipated in the material upon deformation, in which higher loss moduli indicate a greater dissipation of energy due to poor adhesion. FIG. 19 presents the loss moduli for the series of FRPs as well as the frequency-dependent behavior for two of the FRPs.

At the same diacid loadings, the trans,trans-muconate FRP consistently possessed the lowest loss modulus followed by cis,cis-muconate, fumaric acid, and maleic anhydride. As the limits of styrene compatibility were approached, the maleic anhydride-FRPs began to exhibit frequency dependent behavior in the loss modulus, which along with higher loss modulus is indicative of poor adhesion. Thus, in the case of the styrene-based FRPs, trans,trans-muconate exhibited the best performance, and all the FRPs exhibited poor performance with styrene at high olefinic loadings. The poor performance is attributed to styrene being incompatible with the copolymer and thus not full solubilizing or reacting with the copolymer. The lack of crosslinking subsequently leads to a low glass transitions temperature in the resulting composite.

Figure 20:
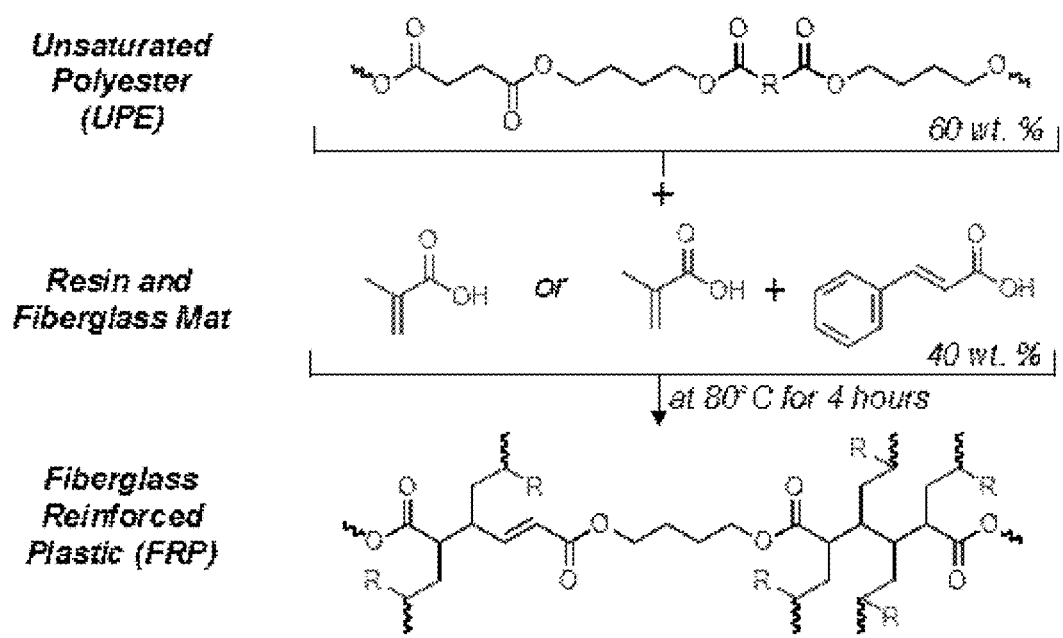
FIG. 20 illustrates reaction chemistry for incorporating bio-copolymer resins into FRP fabrication, according to some embodiments of the present disclosure. The bio-copolymer was dissolved in methacrylic acid or a mixture of methacrylic and cinnaminic acid, infused into a fiberglass mat, and cured.
Figure 21:
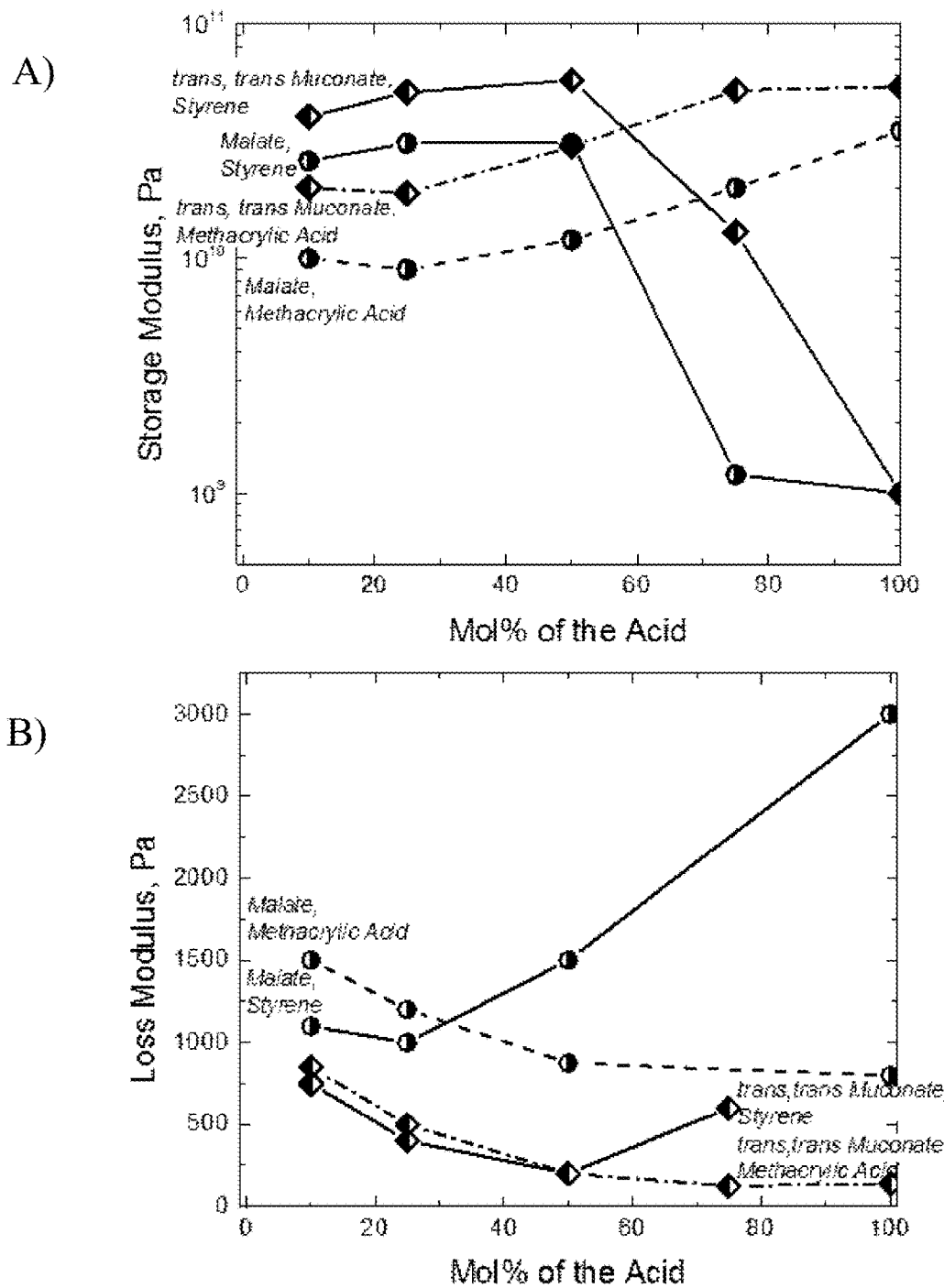
FIG. 21 illustrates the storage (Panel A) and loss moduli (Panel B) of various neat methacrylic acid (MA) FRPs compared to the styrene FRPs at 1 Hz as a function of olefinic loading, according to some embodiments of the present disclosure. As the loading of olefinic diacid increased, the storage modulus increased while the loss modulus decreased for all copolymers, and there was no observed incompatibility with the methacrylic acid resin. As is the case with the styrene-based composites, the trans, trans-muconate copolymers exhibited the highest storage modulus and the lowest loss modulus followed by the cis,cis-muconate, fumarate, and malate copolymers.

Bio-Derivable Resins and FRPs:

The styrene-based FRPs are robust materials at low olefinic loadings, but styrene toxicity is a controversial issue in composite manufacturing. As such, methacrylic acid was investigated as an alternative resin to improve copolymer compatibility and enable a completely renewable polymer/resin system that poses less health risks than styrene. Copolymers were dissolved in neat methacrylic acid infused into a 2-ply fiberglass mat and crosslinked to form an FRP, as shown in FIG. 20. All of the copolymers demonstrated greater compatibility with methacrylic acid relative to styrene and, as such, enabled higher loadings of the olefinic monomer into the polymer backbone. In the region where both styrene and methacrylic acid are compatible with the copolymer, the methacrylic acid possessed a lower storage modulus; this result is shown in FIG. 21. Similar to the styrene-based FRPs, the resins comprised of trans,trans-muconate copolymers dissolved in methacrylic exhibited the highest storage moduli. At higher olefinic monomer loadings in the copolymers, the storage modulus of the methacrylic resin FRPs matched the best performance of the styrene-resin FRPs.

While the differences are apparent in storage modulus, they are less pronounced in the loss modulus, as shown in FIG. 21. The trans,trans-muconate FRPs possessed the lowest loss moduli at the same acid loading. At higher olefinic loadings, the methacrylic-trans,trans-muconate FRPs possessed a lower loss moduli than all other synthesized FRPs. Additionally, the methacrylic-maleic anhydride-FRPs possessed lower loss moduli at the higher loadings due to the high compatibility with the methacrylic acid compared to styrene. Overall, the methacrylic acid resins enabled higher olefin loadings and greater copolymer/resin/fiberglass compatibility; however, when compared to styrene, methacrylic acid does not possess any side groups that may impart rigidity to the final FRP and thus the shear and storage moduli of the methacrylic acid-FRPs were lower than the styrene-FRPs.

Figure 22:
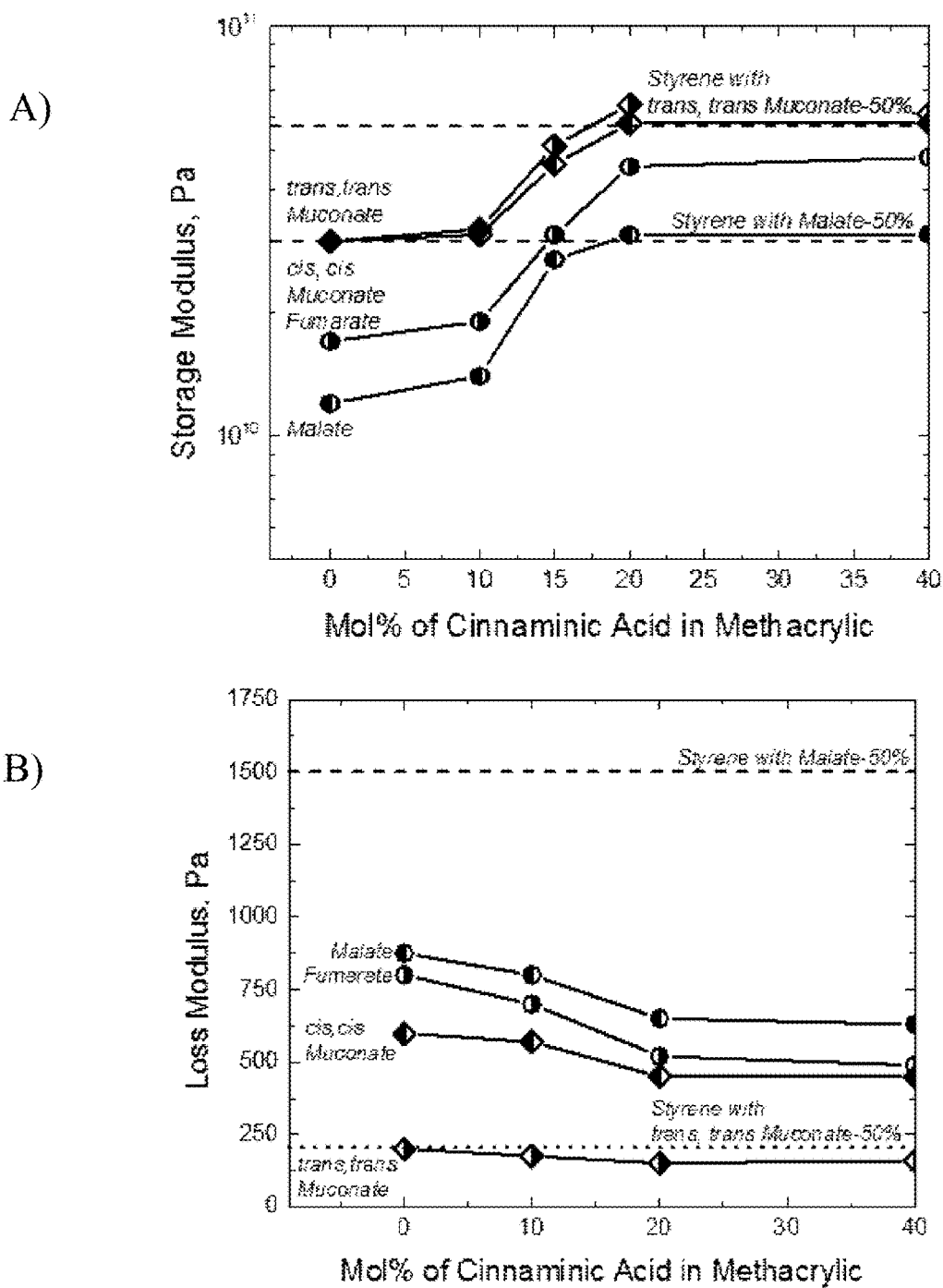
FIG. 22 illustrates the storage (Panel A) and loss moduli (Panel B) of the composites synthesized with the copolymer at 50% loading at 1 Hz synthesized with neat methacrylic acid with various loadings of cinnaminic acid with dashed lines indicating the storage and loss moduli of the styrene composites, according to some embodiments of the present disclosure. The upper limit of cinnaminic acid is 40 mol % in methacrylic acid. As the loading of cinnaminic acid was increased, the storage modulus also increased, and matches/exceeded the modulus of styrene composites at higher loadings, while the loss modulus was favorable in all cases due to the higher compatibility of the copolymers with methacrylic acid.
Figure 23:
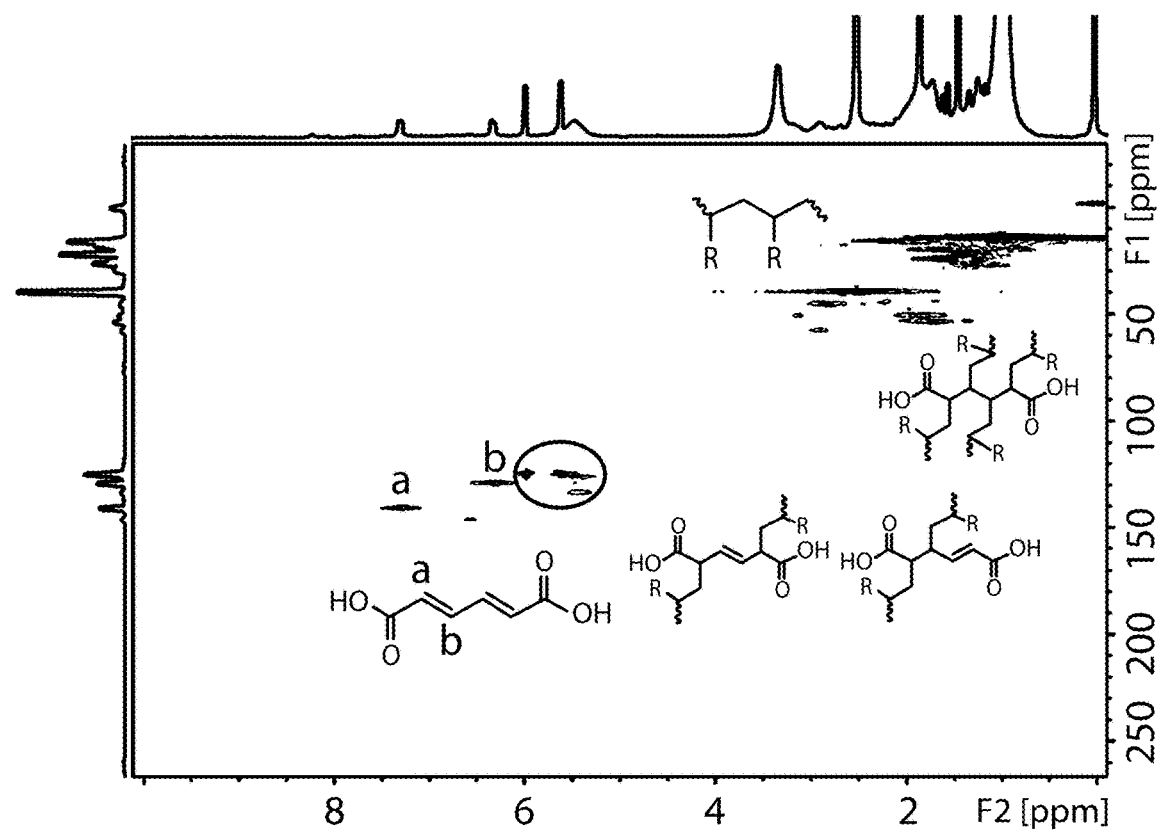
FIG. 23 illustrates 2D NMR of the trans,trans-muconic acid/methacrylic acid polymer in d6-DMSO, according to some embodiments of the present disclosure.
Figure 24:
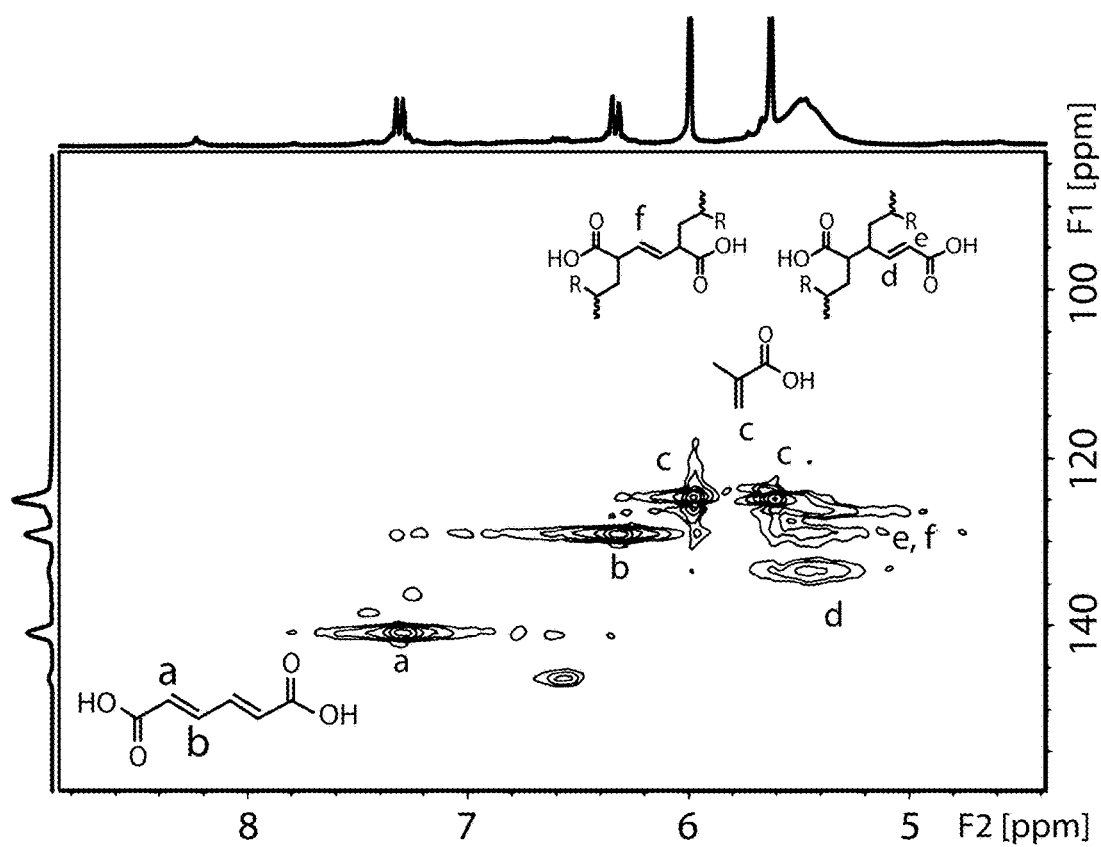
FIG. 24 illustrates 2D NMR of the trans,trans-muconic acid/methacrylic acid polymer in d6-DMSO zoomed in on the olefinic polymer region with peaks labeled, according to some embodiments of the present disclosure.
Figure 25:
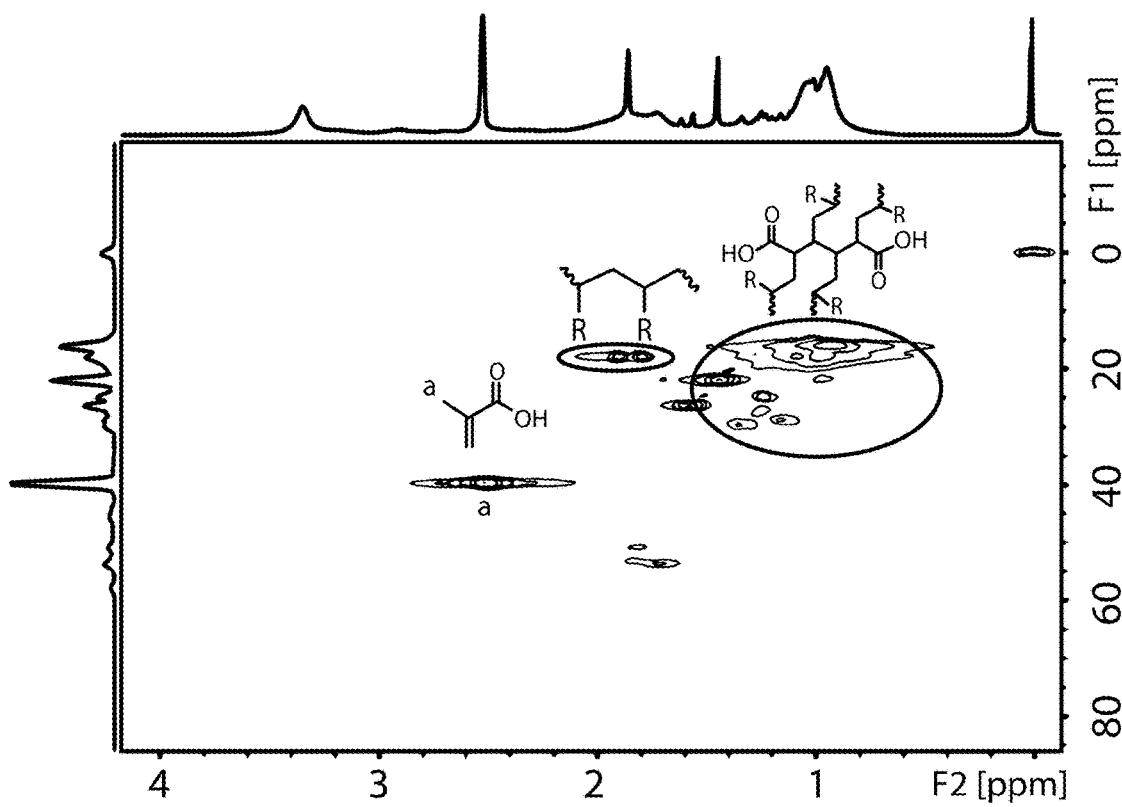
FIG. 25 illustrates 2D NMR of the trans,trans-muconic acid/methacrylic acid polymer in d6-DMSO zoomed in on the olefatic polymer region with peak regions labeled as to what structure they correspond to, according to some embodiments of the present disclosure.
Figure 26:
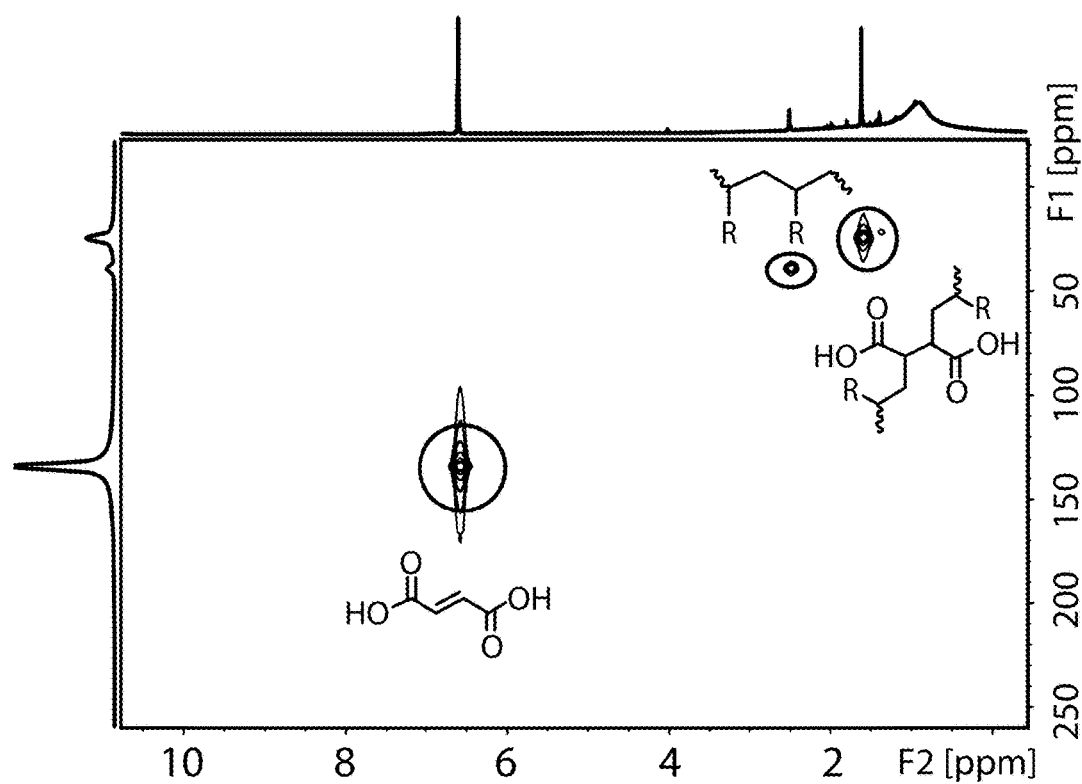
FIG. 26 illustrates 2D NMR of the fumaric acid/methacrylic acid polymer in d6-DMSO, according to some embodiments of the present disclosure. There was little methacrylic acid left over and the corresponding polymer regions are circled.

To try to overcome the disadvantages of the neat methacrylic resin, other diluents, specifically cinnaminic acid, were incorporated into the resin formulation. Cinnaminic acid is soluble in methacrylic acid up to 40 mol %, is a model lignin-derived monomer, and was hypothesized to be able to impart greater rigidity into the final FRP. FIG. 22 shows the storage and loss moduli of the FRPs synthesized with trans,trans-muconate-50% and PBS-maleic anhydride-50% copolymers and methacrylic acid at various loadings. At low loadings of cinnaminic acid, there was little change in the moduli; however, around 15 mol % there was a significant increase in properties and at 20 mol % loading the properties of the methacrylic-cinnaminic resin match that of the styrene resin. Below 15 mol %, there was less than one cinnaminic acid unit per cross-link on average, but at higher loadings, there was on average at least one cinnaminic acid unit per crosslink resulting in the steep change in storage moduli. These effects were less apparent in the loss moduli due to the higher compatibility of methacrylic acid with the copolymers.

Figure 27:
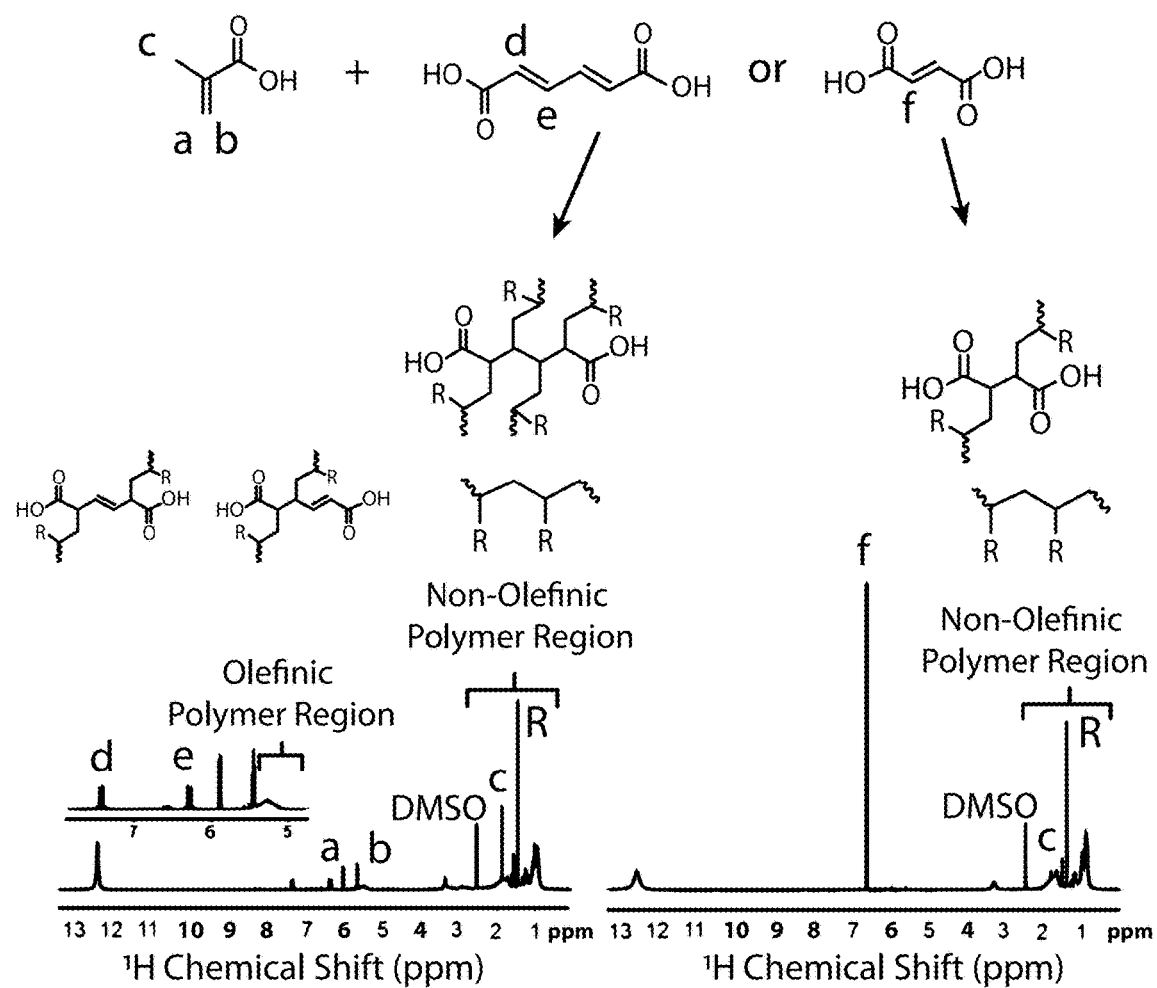
FIG. 27 illustrates NMR Spectra of the reaction of trans, trans-muconate (left) and fumaric acid (right) with methacrylic acid at t=6 hours, according to some embodiments of the present disclosure.
Figure 28:
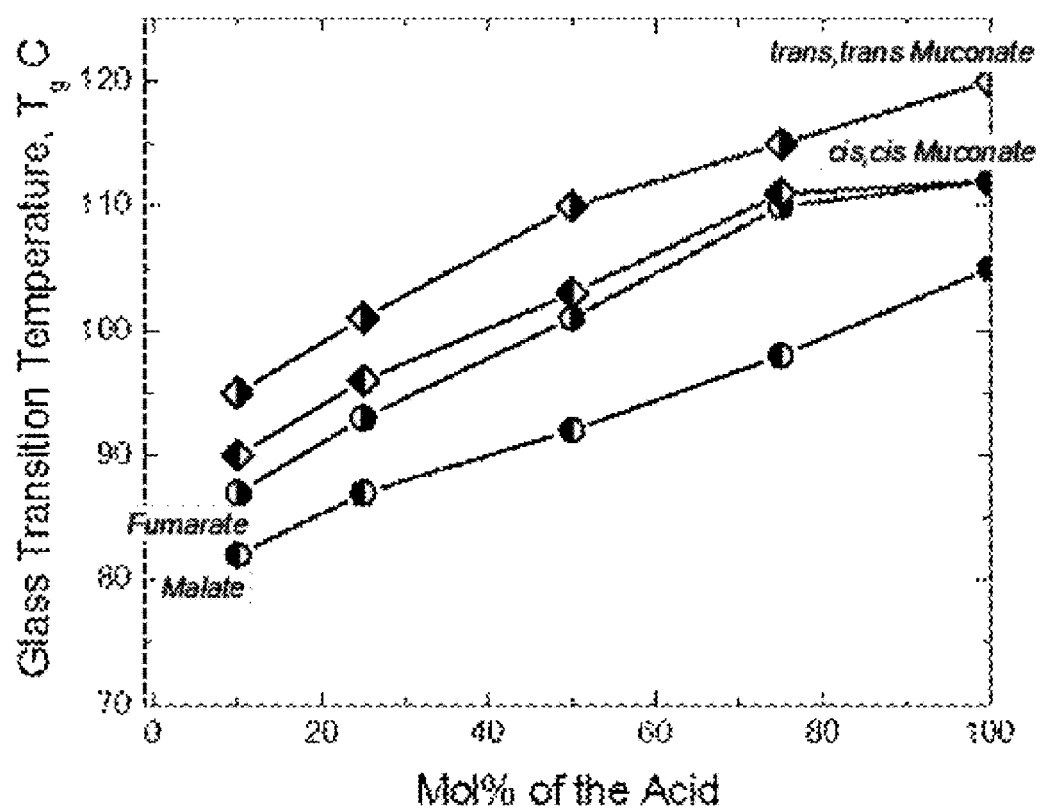
FIG. 28 illustrates glass transition temperatures of the methacrylic acid synthesized FRPs, according to some embodiments of the present disclosure.

Crosslink Formation:

To ascertain the mechanism by which the muconate-based composites derive their favorable properties (e.g. higher shear and storage modulus, higher $T_g$), the structural features of the final composite and the rate at which the crosslinks form must be determined. The structure of the crosslinks was determined by dissolving the olefinic monomers in $d_6$-DMSO with 2.5 molar equivalents of methacrylic acid and subjecting the mixture to free-radical polymerization. Monomers were used in place of the polymers and methacrylic acid was used as the reactive diluent instead of styrene to ensure no interference between the NMR peaks of the reactants and NMR peaks of the cross-linked network. Both fumarate and muconate reacted with methacrylic acid, as indicated by the diminishing double bond peaks between 6.0 and 8.0 ppm and formation of a polymeric region between 1.0 and 2.5 ppm. In this polymeric region, fumarate participates in one cross linking reaction per olefinic monomer unit while the muconate participates in two cross linking reactions per olefinic monomer. The greatest difference between muconate and fumarate/malate is the formation of an olefinic/aromatic polymer region, as indicated by the signal between 5.0 and 5.5 ppm. This region indicates that only one of the muconate double bonds reacted to form a cross-link and, due to the lack of discernable peaks in this region, the polymer order is assumed to be random and lack crystallinity. Two-dimensional $(2D)^1H/^{13}C$ HSQC NMR, FIGS. 23-26, confirms the structures presented in FIG. 27. 2D NMR also indicates that the olefinic polymer region from 5.0 ppm to 6.0 ppm and the shifts around 1 ppm form C3 carbons in muconate are more prevalent in cross-linking formations than the C2 carbons.

Methacrylic acid also reacted differently with muconate relative to fumaric acid. In the case of fumaric acid, all of the methacrylic acid was consumed during the reaction period (6 hours), while in the case of trans,trans-muconate, the muconate and methacrylic acid were consumed in equal proportions. The equal consumption of both monomers indicates that the trans,trans-muconate is more likely to form an alternating copolymer structure with muconate compared to fumarate. Taken together, the olefinic polymer region in the muconate FRPs, the demonstrated ability to possess two crosslinks per muconate molecule, and the possibility of an alternating copolymer structure contributes to the higher $T_g$ and storage moduli observed in the muconate copolymers. It can be surmised that the unreacted double bond of the muconate facilitates adhesion of the glass fibers.

In addition to the differences between the monoene and diene monomers, differences arose due to the isomeric configuration of the monomers. In general, the cis-isomers possessed lower extents of reaction and lower reaction rates than their trans-counterparts, as presented in Table 8. Additionally, the cis-isomers were capable of undergoing isomerization, with cis,cis-muconate isomerizing to cis,trans-muconate and trans,trans-muconate. When comparing the suite of olefinic monomers, the difference in reaction rate indicates that the trans-materials derive their favorable properties by possessing a higher crosslink density that is the result of the higher reaction rate afforded by the accessibility of the trans-double bond.

TABLE 8

Summary of NMR data used to track the extent and rate of reaction. The reaction was conducted in 49.9 mol % DMSO, 0.1 mol % AIBN, 15 mol % olefinic monomer, and 35 mol % methacrylic acid at 60° C. The extent of reaction is relative to the amount of methacrylic acid consumed in 6 hours and the reaction rate is based of the first 30 minutes of polymerization measured by methacrylic acid consumption.

| Olefinic Monomer | Extent of Reaction | Reaction Rate |
| --- | --- | --- |
| maleic anhydride | 85% | $0.7*10^{-4}$ |
| fumaric acid | 99% | $1.6*10^{-4}$ |
| trans,trans-muconate | 92% | $1.4*10^{-4}$ |
| cis,cis-muconate | 87% | $0.9*10^{-4}$ |

Discussion:

Monomers from biologically derived feedstocks can enable the synthesis of performance-differentiated materials to serve as functional replacements for current petroleum derived materials. Many molecules can be produced from lignocellulose-derived building blocks that not only possess the ability to undergo polymerization, but also have functionalities that can impart favorable properties to the final material. Biocompatibility and biodegradation are just two examples of common functionality afforded to bio-derived materials; however, there is a need to develop materials that can exploit the additional functionality present in bio-derivable chemical building blocks (e.g. higher presence of olefinic bonds) that enable performance differentiated materials. As demonstrated herein, the presence of double bonds in the backbones of multifunctional acids can also enable additional chemistry and subsequent performance differentiation in material properties.

Muconic acid is not currently produced at an industrial scale, but it is a promising platform chemical due to its diacid functionality, facile conversion to adipic acid, and potential to be upgraded to other chemicals (e.g. 3-hexenedioc acid and terephthalic acid). Muconic acid can be biologically produced from sugars and from lignin-derived aromatic compounds. Due to its diacid and diene functionality, muconic acid is a promising monomer for direct polyester synthesis, specifically copolymers for composite applications. This current work improves on previous studies by exploring the effect of the isomers of muconate, the loading of muconate, and the effects of varying diluents on final material properties.

cis,cis-muconic acid has been copolymerized with butanediol and succinic acid to produce a copolymer that was subsequently cross-linked with styrene around a woven fiberglass mat. Neat cis,cis-muconic acid was found to demonstrate sub-stoichiometric incorporation into the copolymer, while dimethyl cis,cis-muconate was found to demonstrate stoichiometric incorporation. The loading of muconate into all the copolymers was less than 12.5%, and no isomerization was observed. Additionally, the copolymers prepared with cis,cis-muconic acid exhibited a higher $T_g$, which is associated with large regions of the butanediol-muconate in the polymer backbone, similar to what is observed for the butanediol-muconate homopolymer and the copolymers at high muconate loading. In the present work, however, there is isomerization of the cis,cis-muconate present in the polymer backbone at higher loadings. This work also demonstrates that the trans,trans-muconate results in polymers with a higher $T_g$ than cis,cis-muconate, which is attributed to the presumed restricted molecular motion associated with the extended-linear confirmation of trans,trans-muconate. The FRPs synthesized in our previous work demonstrate slight differences depending on whether or not the copolymer was synthesized with the neat cis,cis-muconic acid or dimethyl cis,cis-muconate, and were only synthesized at the low loadings in styrene, thus they did not implement a bio-derivable resin nor did they find the limit of styrene compatibility with muconate.

Despite the robust performance of the styrene-based FRPs at low olefinic loadings, methacrylic acid was investigated as an alternative diluent to overcome some of styrene's disadvantages. Producing styrene biologically is challenging due to its high cell toxicity and styrene is carcinogenic. Methacrylic acid can be obtained from the decarboxylation of itaconic acid, which can be obtained biologically. Methacrylic acid is a liquid at room temperature, enabling it to be used as a diluent in forming biobased resins. While caustic, methacrylic acid has a lower volatility than styrene and has not been shown to be carcinogenic. Overall, methacrylic acid results in a higher compatibility with the more crystalline polymers than styrene and can be blended with cinnaminic acid to obtain FRPs with performance-differentiated properties.

Methacrylic acid is just one potential monomer for use in bio-based composites. To be considered for a styrene replacement in FRPs, the monomer should be a liquid at room temperature and possess the ability to dissolve the copolymers. Additionally, it is desirable to have monomers that are less volatile and less carcinogenic than styrene, while possessing the potential to be derived from biological sources. Examples of other monomers with styrene replacement potential come from lignin depolymerization, such as isoeugenol or trans-methyl phenol (from the dehydrogenation of propyl phenol).

The PBS-muconate copolymers with the methacrylic acid reactive diluent enabled a fully renewable composite. However, to produce a fully renewably-derived reinforced composite, a bio-derivable support should be implemented in place of the fiberglass mat. Bamboo, various types of lignin, and cellulosic materials may be used as reinforcement replacements in thermoplastic and thermoset composites. In general, the properties of the composite can vary widely depending on the reinforcement that is used and the processing technique that is implemented, with most lignin-based systems demonstrating lower shear and storage moduli than typical fiberglass and carbon fiber-reinforced composites. However, some reinforcements such as bamboo enable lightweight composites with high strength to weight ratios. Additionally, to enable these reinforcements to be used, it is important to ensure proper adhesion between the reinforcement and the plastic/resin system.

The performance differentiation in the synthesized reinforced composites may be attributed to the diene functionality in muconate. As demonstrated herein, both bonds can react to form a highly branched unit in the backbone of the copolymer. When only one double bond reacts, a rigid subunit is left behind. For the same FRP formulation, these effects may result in an FRP with a higher crosslink density (lower molecular weight between crosslinks) and a more rigid backbone than fumaric acid and maleic anhydride. Thus, the two double bonds also make muconate a better candidate for a copolymer and FRP use than itaconic and other single olefinic diacids. Furthermore, the trans configuration of the double bond is more reactive than the cis configuration. Maleic anhydride/acid possesses a lower reaction rate because the cis bond appear not to be favorable to cross-linking, with some industrial synthetic routes varying the reaction conditions to encourage isomerization of the cis-maleic form to the trans-fumaric form. The higher reactivity of the trans bonds leads to a higher crosslink density and higher shear and storage moduli. It is important to note that the trans,trans-muconate is also preferable to use over cis,cis-muconate as the trans, trans dimethyl ester can be produced a higher yields than the cis,cis dimethyl ester and does not undergo isomerization during the polymerization reactions. Overall, trans,trans-muconate is demonstrated to possess the best performance compared to cis,cis-muconate, fumaric acid, and maleic anhydride. Due to these effects, one trans,trans-muconate in a copolymer backbone is equivalent to approximately three maleic units in terms of the storage moduli, and four maleic units in terms of loss moduli. Furthermore, the methacrylic-based resins are demonstrated to possess greater compatibility with a wider range of copolymers compared to the styrene resins. Such resins also enable the fabrication of fully renewable composites with a different reinforcement selection.

Esterification of Muconic Acid for Polymerization:

Esterification of the diacid monomer is not typically required for catalyzed polymerization reactions with saturated monomers. However, diester monomers are commonly used in the commercial production of PET to circumvent the poor solubility and high melting temperature of terephthalic acid. To explore the utility of using the diester, cis,cis-muconic acid was esterified under basic conditions to produce dimethyl cis,cis-muconate. The muconate ester is more soluble in the diol (and subsequently the reaction mixture) than the neat muconic acid and has a lower melting point; these attributes are summarized in Table 9. Initially, dimethyl cis,cis-muconate comprising 12.5% of the total non-diol concentration was charged to the reactor and subsequently polymerized in the previously described manner. Importantly, utilization of the diester yields a polymer with near stoichiometric incorporation of muconate and a slightly higher molecular weight.

TABLE 9

Properties of cis,cis-muconic acid, dimethyl cis,cis-muconate, and the copolymer synthesized with dimethyl cis,cis-muconate.

| Property | Value |
| --- | --- |
| cis,cis-Muconic Acid | |
| Melting Point | 197° C. |
| Purity | 99.2 mol. % |
| Solubility in Butanediol (mol:mol) | 0.05:1 |
| Dimethyl cis,cis-Muconate | |
| Melting Point | 78° C. |
| Purity | 99.1% |
| Solubility in Butanediol (mol:mol) | 1:1 |
| PBSM(E)-12.5% Ester Incorporation | |
| Muconate Incorporation (mol % acid units) | 12.4% |
| Molecular Weight | $1.86 \times 10^5$ g/mol |
| Đ | 2.0 +/− 0.1 |
| Melting Temperature, $T_M$ | 115° C. |
| Glass Transition, $T_g$ | −15° C. |
| Decomposition Temperature, $T_{D, 50}$ | 385° C. |

Figure 29:
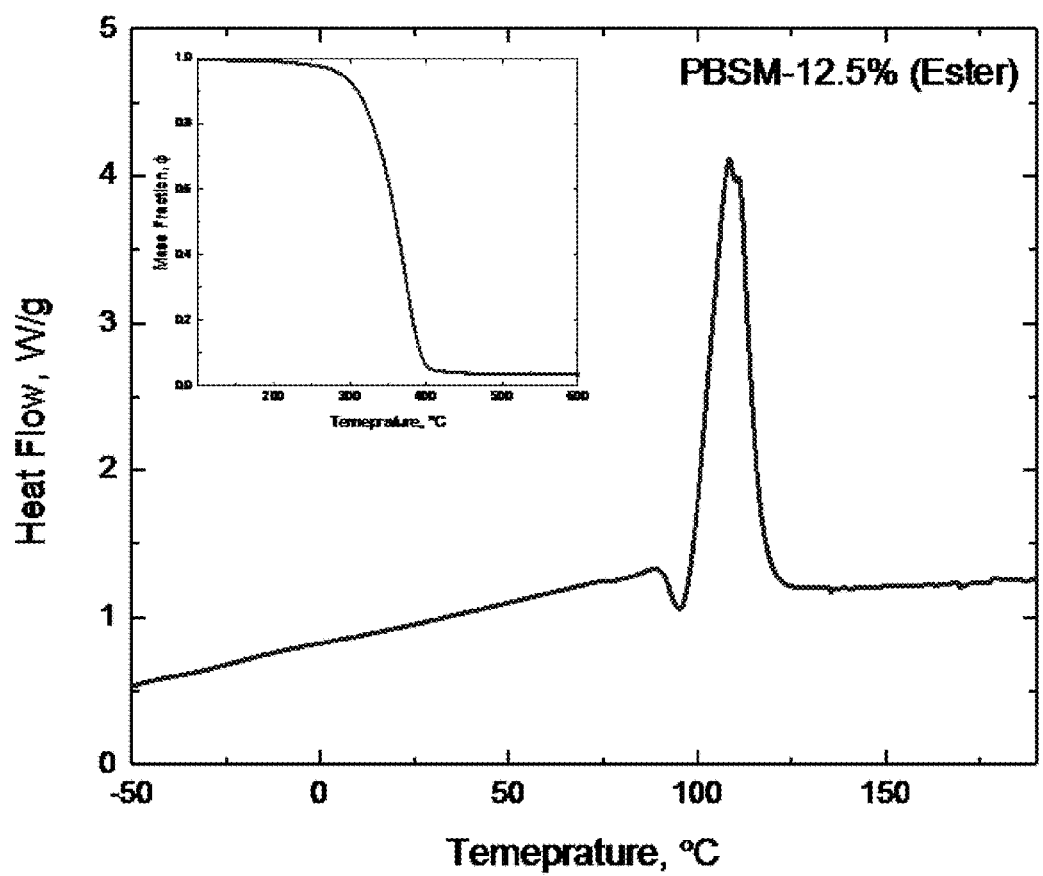
FIG. 29 illustrates thermal data for the PBSM(E)-12.5% polymer synthesized using dimethyl cis,cis-muconate ester, according to some embodiments of the present disclosure. In the DSC scan, there was no evidence of a second glass transition.

FIG. 29 provides thermal data for the PBSM(E)-12.5% synthesized with the dimethyl ester as the starting material. As before, the melting temperature is depressed, the glass transition temperature is elevated, and the decomposition temperature is lowered. This is consistent with previous experiments: muconic acid is incorporated into the backbone of the polymer, resulting in retarded segmental motion and disruption of crystalline packing. However, unlike previous experiments with the PBSM copolymers, there is no second $T_g$. This lack of the second $T_g$ combined with an increase in the $T_g$ and stoichiometric incorporation of the muconate indicates that the structure of PBSM synthesized with the ester is that of a random copolymer.

Figure 30:
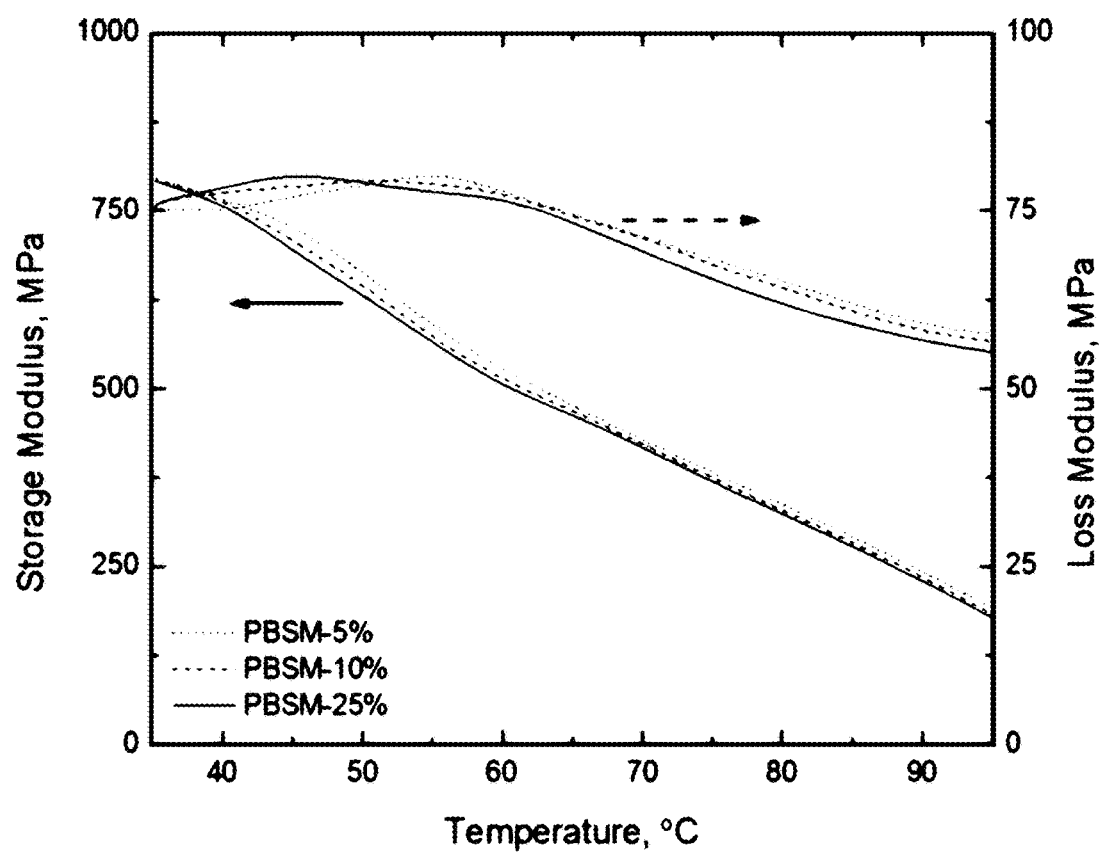
FIG. 30 illustrates storage and loss modulus for the PBSM copolymer as a function of temperature, according to some embodiments of the present disclosure. The inflection in the storage modulus and local maximum in the loss modulus is indicative of a glass transition temperature. The second glass transition temperature decreased with increasing muconic incorporation, in agreement with the observation from DSC. For comparison, the PBSM(E) did not show an inflection or local maximum.

Mechanical Properties of Poly(Butylene Succinate-Co-Muconate) from cis,cis-Muconic Acid and Dimethyl cis,cis-Muconate:

To evaluate polymer performance and to confirm the presence of a second $T_g$ in the PBSM(A) copolymers, dynamic mechanical analysis (DMA) was performed on injection-molded pieces of the copolymer. FIG. 30 provides the storage and loss modulus for the PBSM copolymers. Overall, the copolymers exhibit a higher modulus than that of PBS (E'~300 MPa at 35° C.) and demonstrate behavior that is expected of polyesters above their first glass transition temperature. The second $T_g$ in the samples synthesized with neat cis,cis-muconic acid is indicated by an inflection in the storage modulus followed by a local maximum in the loss modulus. The location of the moduli is higher than the $T_g$ reported via DSC, which is consistent with theory and other experimental observations.

In the case of the copolymer synthesized from the ester (PBSM(E)-12.4%), there is no inflection in the storage modulus, nor is there a local maximum in the loss modulus, indicating that there is no second $T_g$, indicating that the copolymer is random when synthesized with the ester. The copolymer still possesses a higher modulus than PBS, however, the PBSM(E)-12.4% possesses a slightly lower modulus than the polymer synthesized with neat acid. This is consistent with the aforementioned hypothesis that when PBSM is synthesized with the acid it possesses a tapered structure, while in the case of the ester the structure, it forms a random copolymer.

Figure 31:
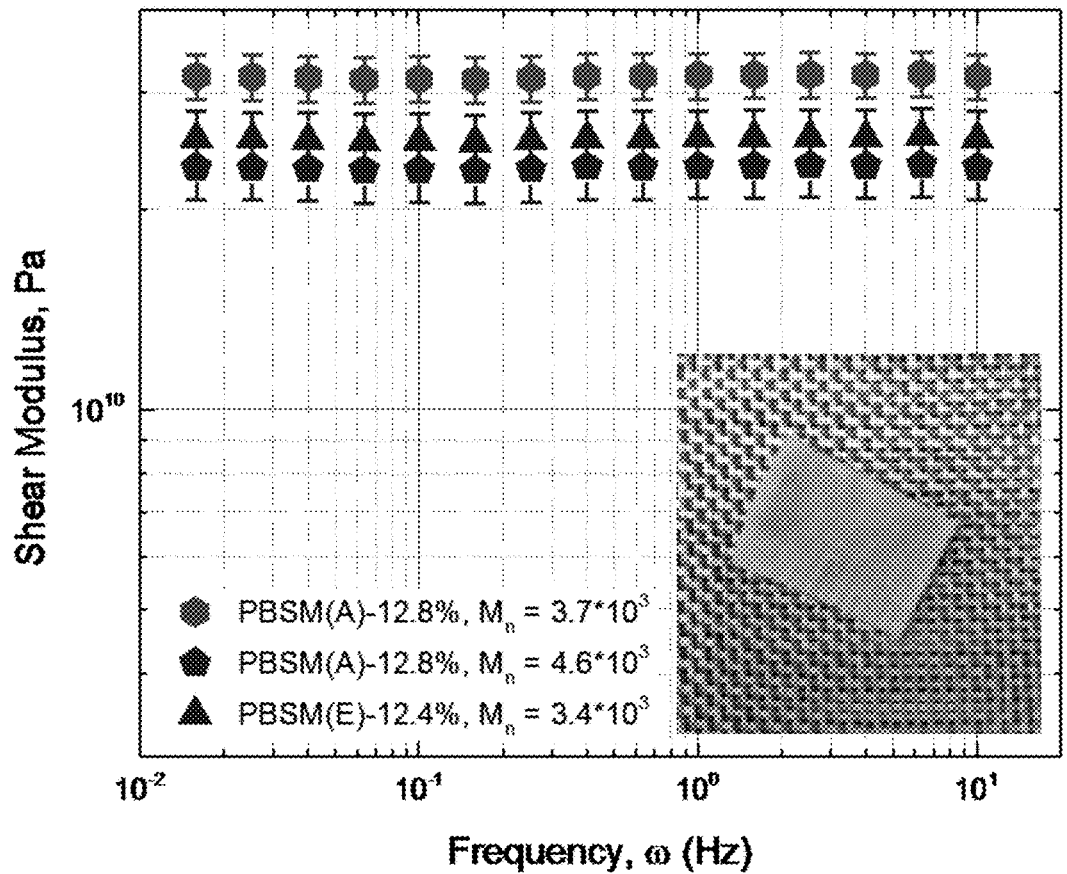
FIG. 31 illustrates shear modulus as a function of frequency for the synthesized composite, according to some embodiments of the present disclosure. Photo of the composite (lower right) on top of a sheet of woven fiberglass. Standard deviations were calculated from multiple composites synthesized at different times with the same formulation. Fiber content within a data set and across all data sets is found to be ±1.3 wt. %.

FIG. 31 shows that the modulus is independent of frequency for all of the composites, demonstrating that the composites behave as elastic solids rather than a viscoelastic polymer over the frequency range investigated. In the studied cases, the composites that were synthesized with the acid had higher moduli than the composites synthesized with the ester. Furthermore, in the case of the acid-synthesized material, the modulus of the final composite is found to decrease with increasing molecular weight of the precursor polymer. This indicates that the PBSM(A) copolymers provide tunability due to their unique structure. The highest measured shear modulus in this study was 31.8 GPa, which is typical of fiberglass composites formed using copolymers. This composite exhibited a glass transition temperature of 90° C., a degradation temperature of 400° C., and no $T_m$.

In all the polymers synthesized with neat cis,cis-muconic acid, denoted PBSM(A), the resultant incorporation of muconic acid is lower than the initial stoichiometry, and the PBSM(A) copolymers possess a lower molecular weight and modified thermal degradation profiles. The sub-stoichiometric incorporation and the likely tapered molecular architecture can be attributed to the low reactivity of the muconic acid monomer. Namely, we hypothesize that the conjugated nature of muconate results in a greater distribution of electron density over the whole molecule, making it relatively less electrophilic at the carbonyl carbon compared with succinic acid (Scheme 3). This implies the carbon is less susceptible to nucleophilic attack by butanediol when complexed with the catalyst.

Scheme 3.

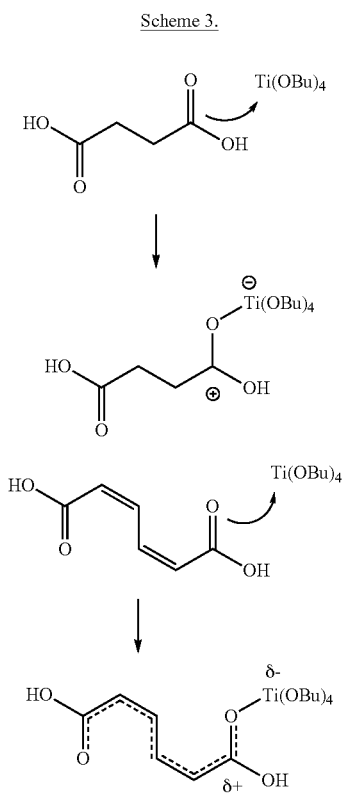

(A) Activation of succinic acid carbonyl carbon by Ti(OBu)4 catalyst (B) Corresponding activation of muconic acid, where charge is delocalized by the pi electron system.

In the case of the PBSM(A) copolymers, two $T_g$ are observed and both exhibit compositional dependence. The possibility of two separate molecular structures being present is discounted based on the GPC results and the TGA results (presented in FIG. 7 (4)). Both indicate that only one molecular species is present. A separate elution peak or a broader molecular weight distribution (Đ>2) in the GPC trace would indicate separate polymer structures. In addition, when multiple species are present, a TGA typically shows step-wise degradation regions. While speculative, the presence of two glass transitions might be attributed to the muconic acid groups reacting, on average, at a later stage of the polymerization reaction than the succinic acid; this would lead to the muconic acid-derived structural units being preferentially located nearer to the chain ends. Based on the relative, hypothesized reactivities of succinic and muconic acids, it is likely that the structure of the polymer would be block-like, which would give rise to a second $T_g$.

The dimethyl ester offers several advantages to neat muconic acid. Specifically, the insensitivity of transesterification to the presence of double bonds combined with increased solubility in the diol and the lower melting point of the ester enables stoichiometric incorporation of muconate into the final polymer. This full incorporation enables more easily targeted polymer compositions. However, because the yield on the esterification reaction is 52%, overall utilization of the muconic acid substrate is equal. In addition, an increased molecular weight is obtained with the same reaction time if the muconate ester is compared to the neat muconic acid. The dimethyl cis,cis-muconate possess the lowest melting temperature (all other forms of muconic acid and muconate possessing $T_m$ in excess of 170° C.) making it the ideal candidate for polymerization. While the ester does offer the benefit of stoichiometric incorporation, there is an apparent benefit in the tapered structure of the acid-derived polymers. Specifically, the tapered copolymer structure leads to a higher modulus in both the injection-molded polymers and composites. In the case of the PBSM (A) copolymer, there is a dependence of the modulus on molecular weight. As the molecular weight is increased, the modulus decreases, which implies an increase in the molecular weight between crosslinks for the composite. This effect could arise because the muconic acid units likely exist near the chain ends of the PBSM(A) copolymer. This control of the polymer molecular architecture enables tailoring of composite properties. In the case of the PBSM(E), however, the muconic units are likely randomly distributed through the polymer. Additionally, these changes in composite properties can be attributed to the unreacted muconic blocks stiffening the composite matrix. Due to the uniformity in crosslink site density, there is no inherent tunability present with the PBSM(E) copolymer and a lower modulus is obtained at the same muconic acid loading. It is important to note that the changes in modulus do not arise due to the change in fiber content (±1.3 wt %), nor from the reactions yield (between 87% to 93%), as both variations are found to be non-correlative. Overall, the composites exhibit both a robust mechanical and thermal profile. The shear modulus of all synthesized composites is suitable for typical fiberglass composite, while the high glass transition temperature of 90° C. and lack of melting temperature enables continual use up to the decomposition temperature. This proof-of-concept testing conclusively demonstrates that muconic acid can be utilized in the development of sustainable, tunable, bio-renewable copolymers.

Conclusions:

This work demonstrates the utility of implementing muconate derivatives into the backbone of polyesters for composite applications and the advantages of using different reactive diluents than styrene for FRP synthesis. In all cases at comparable olefinic monomer loadings, and regardless of reactive diluent, the trans,trans-muconate based copolymers resulted in composites with the best property suite, specifically high strength and favorable adhesion to the fiberglass mat. Additionally, the use of methacrylic acid enables a wide range of copolymers to be used in FRP synthesis and demonstrates the ability to synthesize renewable FRPs. Performance-differentiated FRPs in which the copolymer and reactive diluent can both be 100% renewably sourced hold significant environmental and economic promise and can enable new industrial applications.

Second Materials and Methods:

Monomer Preparation:

All monomers used in this study were repurified to reach a high purity. Purity of the monomers is determined via melting point depression using a TA instruments Q-5000 Digital Scanning calorimeter (DSC) using the TA Instruments Universal Analysis Software. The purity of all compounds is found to be greater than 99.9%.

Succinic acid and butanediol are purified for implementation in all the copolymer backbones. Succinic acid is dissolved into acetic acid at 60° C. and subsequently slowly cooled to 20° C. The acetic is subsequently filtered off and the succinic acid is placed in a vacuum oven to dry for 48 hours. 1,4-Butanediol was purified via vacuum distillation in which the bottoms of the distillation and first fraction from the separation are discarded. Maleic anhydride and fumaric acid, which are used as olefinic monomers in the copolymer backbone, are purified via the same method used for succinic acid.

In order to polymerize muconate into copolymer backbones at high loading, the biologically obtained cis,cis-muconic acid must be converted to a diester. cis,cis-dimethyl muconate is prepared via a previously published method of Frost et. al. 39 in which cis,cis-muconic acid was reacted with dimethyl sulfate (1:2 molar ratio) for 6 h in an aqueous solution of sodium hydroxide. The reaction mixture was extracted with ethyl acetate to recover the product. Subsequently, the ethyl acetate was extracted with aqueous sodium hydroxide and sodium chloride to purify the product before the ethyl acetate was evaporated. The overall yield for cis,cis-muconate preparation is 52%. trans,trans dimethyl muconate is produced via the reflux of cis,cis-muconic acid in methanol with catalytic iodide for 24 hours. Following reflux, the reaction mixture was extracted with ethyl acetate, which was subsequently blown down and the yield of the final product is 95%.

Finally, in order to synthesize the composite as reactive diluent must be used, and in the present work the reactive diluent is styrene, methacrylic acid, or a mixture of methacrylic and cinnaminic acid. Any inhibitors present in styrene and methacrylic acid are removed via the use of inhibitor remover columns from Sigma Aldrich. Cinnaminic acid is purified via the same method used for succinic acid.

Polymer Synthesis:

For the polymer screening, the copolymers are synthesized via transesterification reactions. All polymerizations were conducted in a three-necked round bottom flask with a mechanical motor in the central neck, nitrogen purge in another neck, and a Dean-Stark/Condenser Trap on the final neck. The reaction mixture is heated to 180° C. under nitrogen. After the reaction mixture had melted the mechanical stirrer was turned on and the reaction proceeded for two (2) hours. After this initial period, vacuum is applied to the system, 0.1 wt % titanium butoxide is added to the reactor and the reaction is allowed to proceed for six (6) more hours. After six hours the stirring is stopped and the heat is turned off. The solid polymer is subsequently dissolved in chloroform and precipitated out in a four times (4×) excess of methanol. In order to attain a lower molecular weight for the polymers used as the copolymer in the composite synthesis, no catalyst is used and polymerization is only conducted for the initial period of two hours.

Structure Determination:

Polymer structure and olefinic incorporation were determined via the use of a Bruker Avance III HD 400 MHz NMR Spectrometer with a 5 mm BBO probe. Quantitative 1H spectra were acquired with a 90° pulse of 14.5 µs and a 30 s recycle delay at room temperature. Two Dimensional (2D) NMR was conducted with 1024 points and a sweep width of 16 ppm in F2 for 1H and 256 points with a sweep width of 300 ppm in F1 for 13C with a relaxation delay of 1.5 seconds and 64 total scans. Deuterated chloroform (99.9% Sigma Aldrich), Deuterated Dimethyl Sulfoxide, and a mixture of the two solvents at a 2:1 volume ratio with 1% w/w TMS are used as the solvent.

Thermal Measurements:

Thermal properties were acquired using a TA Instruments Q-500 thermal gravimetric analysis (TGA) instrument and a TA Instruments Q-5000 digital scanning calorimeter (DSC) with aluminum hematic pans. Unless otherwise noted, all DSC scans were conducted at heating and cooling rate of 10° C./min while all TGA scans were conducted at a ramp rate 20° C./min.

Composite Synthesis:

Composites are prepared by combining 60 wt. % copolymer with 40 wt. % reactive diluent. The mixture was stirred for up to 12 hours before 0.3 wt % AIBN was added. The mixture, with initiator, was subsequently loaded onto double-ply woven fiberglass matt. The matt was placed between two Teflon sheets and heated to 80° C. for four (4) hours. The composite was subsequently placed in a vacuum oven for 48 hours to allow excess unreacted reactive diluent to evaporate.

Mechanical Measurements:

Storage and loss modulus of the composites were determined using a TA Instruments Q5000 Dynamic Mechanical Analyzer. All tests are conducted at 35° C. using the three point bend geometry fixture and samples were prepared by cutting a rectangular sample with dimensions of 35×5×2 mm. Shear moduli were determined with a Rheometric ARES-LS rheometer using torsional rectangular geometry fixtures with the same sample piece.

Crosslinking Studies:

To study the mechanism of crosslinking, methacrylic acid and an olefinic diacid are dissolved in DMSO at variable loadings. AIBN is used as an initiator at a loading 1 wt. % of the total methacrylic acid/olefinic diacid weight. The reaction mixture is heated to 70° C. and aliquots are taken every 15 minutes and studied via NMR.

EXAMPLES

Example 1

A polymer comprising:

a first repeat unit comprising

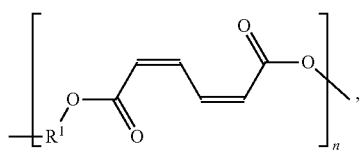

wherein: n is an integer between 1 and 1000, and $R^1$ is a first hydrocarbon group.

Example 2

The polymer of Example 1, wherein the first hydrocarbon group comprises at least one of a first linear alkane or a first branched alkane.

Example 3

The polymer of Example 2, wherein the first hydrocarbon group comprises the first linear alkane having a length between a C1 alkane and a C10 alkane inclusively.

Example 4

The polymer of Example 3, wherein the first linear alkane is a first C4 alkane.

Example 5

The polymer of Example 1, further comprising: a second repeat unit comprising

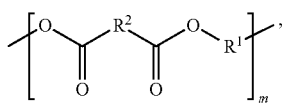

wherein: m is an integer between 1 and 100, and $R^2$ is a second hydrocarbon group.

Example 6

The polymer of Example 5, wherein the second hydrocarbon group comprises at least one of a second linear alkane or a second branched alkane.

Example 7

The polymer of Example 6, wherein the second hydrocarbon group comprises the second linear alkane having a length between a C1 alkane and a C10 alkane inclusively.

Example 8

The polymer of Example 7, wherein the second linear alkane is a C4 alkane.

Example 9

The polymer of Example 5, wherein at least a portion of the first repeat unit and at least a portion of the second repeat unit form a structure comprising

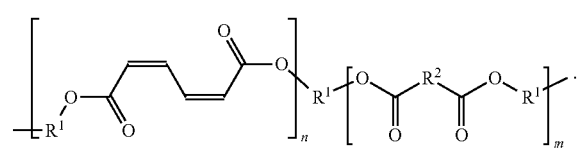

Example 10

The polymer of Example 9, further comprising a first terminal end and a second terminal end, wherein: the first terminal end is a hydroxyl group or a carboxylic acid group, the second terminal end is a hydroxyl group or a carboxylic acid group, and the structure is positioned between the first terminal end and the second terminal end.

Example 11

The polymer of Example 9, wherein a molar amount of the second repeat unit incorporated into the polymer is between 2.0 mol % and 100 mol %.

Example 12

The polymer of Example 9, wherein the polymer has a melting point between 30° C. and 260° C.

Example 13

The polymer of Example 9, wherein the polymer has no melting point.

Example 14

The polymer of Example 9, wherein the polymer has a glass transition temperature between −100° C. and 75° C.

Example 15

The polymer of Example 9, wherein the polymer has a weight average molecular weight between $1 \times 10^3$ and $1 \times 10^6$.

Example 16

The polymer of Example 1, wherein at least a portion of the carbon of the first repeat unit is bioderived.

Example 17

The polymer of Example 16, wherein the bioderived portion of the carbon is determined to be bioderived according to ASTM D866.

Example 18

The polymer of Example 5, wherein at least a portion of the carbon of the second repeat unit is bioderived.

Example 19

The polymer of Example 18, wherein the bioderived portion of the carbon is determined to be bioderived according to ASTM D866.

Example 20

A resin comprising:

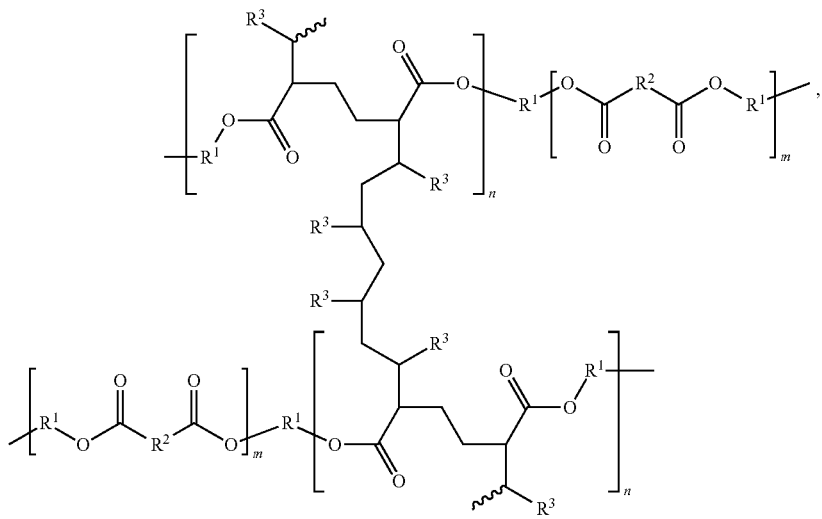

wherein: n is an integer between 1 and 1000, $R^1$ is a first hydrocarbon group, m is an integer between 1 and 100, $R^2$ is a second hydrocarbon group, and $R^3$ is a third hydrocarbon group.

Example 21

The resin of Example 20, wherein the first hydrocarbon group comprises at least one of a first linear alkane or a first branched alkane.

Example 22

The resin of Example 21, wherein the first hydrocarbon group comprises the first linear alkane having a length between a C1 alkane and a C10 alkane inclusively.

Example 23

The resin of Example 22, wherein the linear alkane is a C4 alkane.

Example 24

The resin of Example 20, wherein the second hydrocarbon group comprises at least one of a second linear alkane or a second branched alkane.

Example 25

The resin of Example 24, wherein the second hydrocarbon group comprises the second linear alkane having a length between a C1 alkane and a C10 alkane inclusively.

Example 26

The resin of Example 25, wherein the second linear alkane is a C4 alkane.

Example 27

The resin of Example 20, wherein the third hydrocarbon group comprises an aromatic group.

Example 28

The resin of Example 20, wherein the third hydrocarbon group is a benzene ring.

Example 29

The resin of claim 20, wherein at least a portion of the carbon of the resin is bioderived.

Example 30

The polymer of claim 29, wherein the bioderived portion of the carbon is determined to be bioderived according to ASTM D866.

Example 31

A method comprising a first reacting of a first polymer comprising

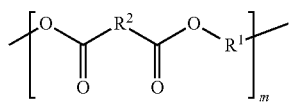

with muconic acid to form a second polymer comprising

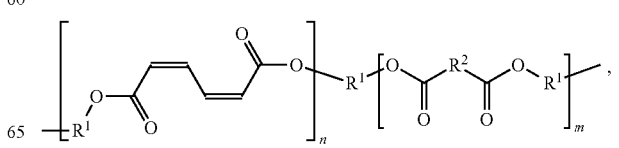

wherein: m is an integer between 1 and 100, n is an integer between 1 and 1000, $R^1$ is a first hydrocarbon group, and $R^2$ is a second hydrocarbon group.

Example 32

The method of Example 31, wherein both terminal ends of the second polymer are terminated with a hydroxyl group.

Example 33

The method of Example 32, wherein a molar amount of the muconic acid incorporated into the second polymer is between 2.0 mol % and 100 mol %.

Example 34

The method of Example 32, wherein the second polymer has a melting point between 30° C. and 260° C.

Example 35

The method of Example 32, wherein the second polymer has a glass transition temperature between −100° C. and 75° C.

Example 36

The method of Example 32, wherein the second polymer has a weight average molecular weight between $1\times10^3$ and $1\times10^6$.

Example 37

The method of Example 31, wherein the muconic acid is bioderived.

Example 38

The method of Example 31, further comprising mixing benzoate with a strain of *Pseudomonas Putida*, wherein the *Pseudomonas Putida* metabolizes the benzoate to produce the muconic acid.

Example 39

The method of Example 31, wherein: the first polymer comprises

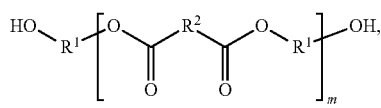

and the first reacting comprises transesterification of the first polymer with the muconic acid to further produce $R^1OH$.

Example 40

The method of Example 39, wherein the first polymer has a melting point between 40° C. and 260° C.

Example 41

The method of Example 39, wherein the first polymer has a glass transition temperature between −100° C. and 75° C.

Example 42

The method of Example 39, wherein the first polymer has a weight average molecular weight between $1\times10^3$ and $1\times10^6$.

Example 43

The method of Example 31, wherein: the first reacting further comprises a starting polymer comprising

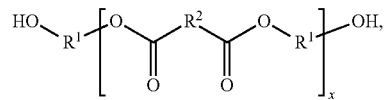

x is an integer between 1 and 1000 and x is less than m, and the starting polymer reacts by condensation to produce the first polymer and water.

Example 44

The method of Example 43, wherein: the first reacting further comprises a diol and dicarboxylic acid, and the diol and the dicarboxylic acid react by condensation to produce the starting polymer.

Example 45

The method of Example 43, further comprising an initial reacting, prior to the first reacting, wherein the starting polymer is formed in the initial reacting by the condensation of at least one diol and at least one dicarboxylic acid.

Example 46

The method of Example 44, wherein at least one of the diol or the dicarboxylic acid is bioderived.

Example 47

The method of Example 44, wherein the dicarboxylic acid comprises succinic acid.

Example 48

The method of Example 31, further comprising a second reacting of the second polymer with a crosslinker comprising a vinyl-terminated hydrocarbon to form a resin.

Example 49

The method of Example 48, wherein the crosslinker is styrene.

Example 50

The method of Example 48, wherein the resin comprises

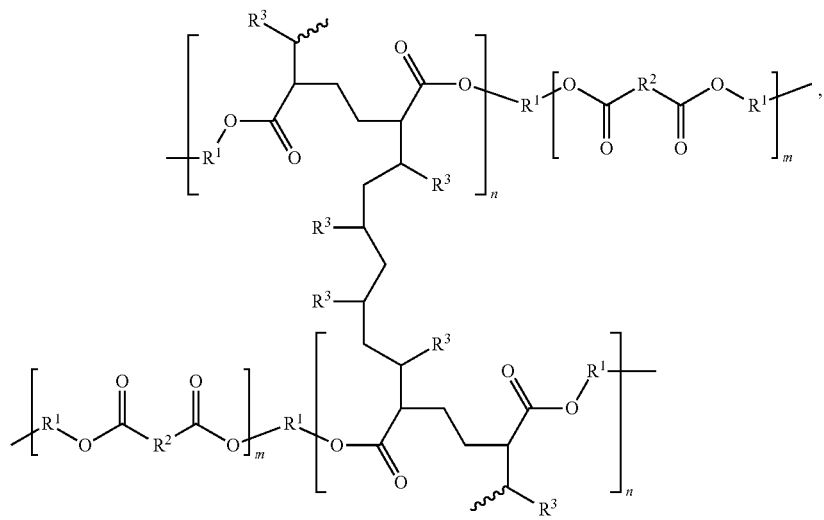

wherein $R^3$ is a benzene ring.

Example 51

The method of Example 44, wherein the diol comprises at least one of 1,2-ethanediol, 1,3-propanediol, 1,4-butanediol, or 1,5-pentanediol.

Example 52

The method of Example 44, wherein the dicarboxylic acid comprises at least one of oxalic acid, malonic acid, succinic acid, glutaric acid, or adipic acid.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A polymer comprising:

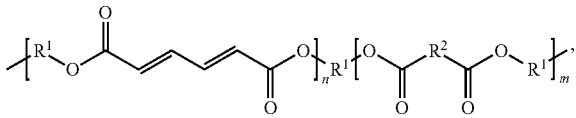

wherein:
the polymer includes a first amount (n) of a first repeat unit where n is an integer between 1 and 1000,
the polymer includes a second amount (m) of a second repeat unit where m is an integer between 1 and 100,
$R^1$ is a first hydrocarbon group, and
$R^2$ is a second hydrocarbon group.

2. The polymer of claim 1, wherein the first hydrocarbon group comprises at least one of a first linear alkane or a first branched alkane.

3. The polymer of claim 2, wherein the first linear alkane has a length between a C1 alkane and a C10 alkane, inclusively.

4. The polymer of claim 3, wherein the first linear alkane is a C4 alkane.

5. The polymer of claim 1, wherein the second hydrocarbon group comprises a second linear alkane having a length between a C1 alkane and a C10 alkane, inclusively.

6. The polymer of claim 5, wherein the second linear alkane is a C4 alkane.

7. The polymer of claim 1, further comprising:
a first terminal end and a second terminal end, wherein:
both the first terminal end and the second terminal end are selected from the group consisting of a hydroxyl group and a carboxylic acid group.

8. The polymer of claim 1, wherein a molar amount of the first repeat unit incorporated into the polymer is between 2.0 mol % and 100 mol %.

9. The polymer of claim 1, wherein the polymer has a melting point between 30° C. and 260° C.

10. The polymer of claim 1, wherein the polymer has no melting point.

11. The polymer of claim 1, wherein the polymer has a glass transition temperature between −100° C. and 75° C.

12. The polymer of claim 1, wherein the polymer has a weight average molecular weight between $1 \times 10^3$ and $1 \times 10^6$.

13. The polymer of claim 1, wherein at least a portion of the carbon of the first repeat unit is bioderived.

14. The polymer of claim 13, wherein the bioderived portion of the carbon is determined to be bioderived according to ASTM D866.

15. A resin comprising:

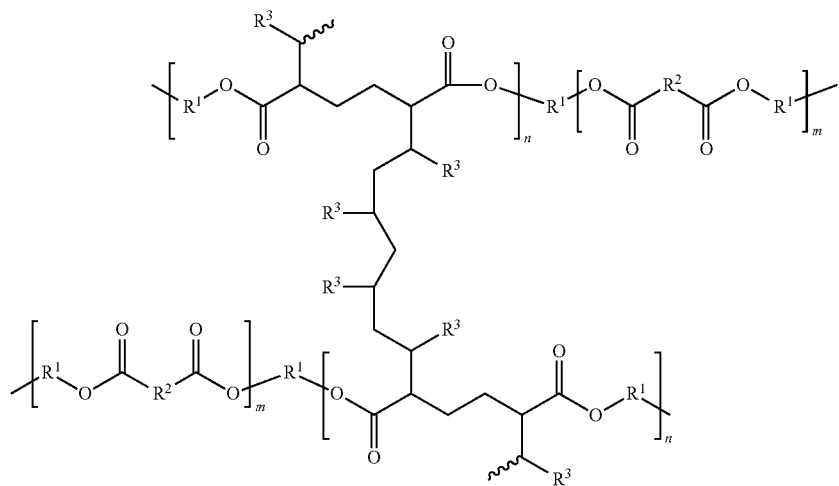

wherein:
n is an integer between 1 and 1000,
$R^1$ is a first hydrocarbon group,
m is an integer between 1 and 100,
$R^2$ is a second hydrocarbon group, and
$R^3$ is a third hydrocarbon group.

16. A method comprising a first reacting of a first polymer comprising

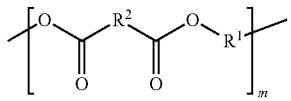

with muconic acid to form a second polymer comprising

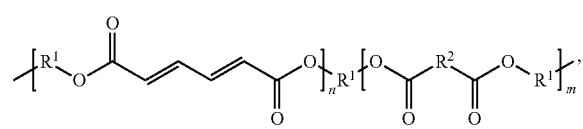

wherein:
in is an integer between 1 and 100,
n is an integer between 1 and 1000,
$R^1$ is a first hydrocarbon group, and
$R^2$ is a second hydrocarbon group.

17. The method of claim 16, wherein the muconic acid is bioderived.

18. The method of claim 16, further comprising mixing benzoate with a strain of *Pseudomonas Putida*, wherein the *Pseudomonas Putida* metabolizes the benzoate to produce the muconic acid.

19. The method of claim 16, wherein:
the first polymer comprises

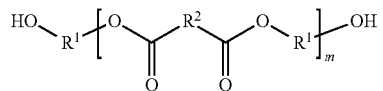

and
the first reacting comprises transesterification of the first polymer with the muconic acid to further produce $R^1OH$.

20. The method of claim 19, wherein:
the first reacting further comprises a starting polymer comprising

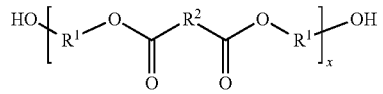

x is an integer between 1 and 100 and x is less than m, and
the starting polymer reacts by condensation to produce the first polymer and water.

21. The method of claim 20, wherein:
the first reacting further comprises a diol and dicarboxylic acid, and
the diol and the dicarboxylic acid react by condensation to produce the starting polymer.

22. The method of claim 21, wherein at least one of the diol or the dicarboxylic acid is bioderived.

23. The method of claim 16, further comprising a second reacting of the second polymer with a crosslinker comprising a vinyl-terminated hydrocarbon to form a resin.

24. The method of claim 23, wherein the resin comprises
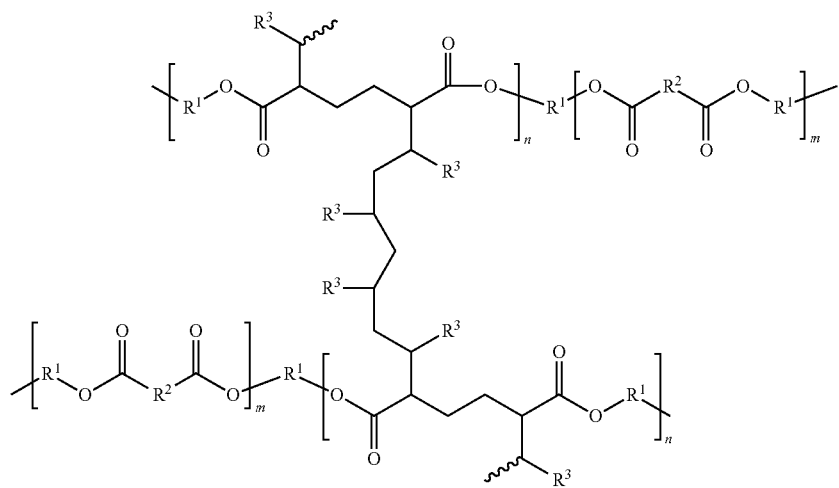
wherein
R³ is a benzene ring.
* * * * *